12) United States Patent
Scherz et al.

(10) Patent No.: US 8,207,154 B2
(45) Date of Patent: Jun. 26, 2012

(54) CATATONIC BACTERIOCHLOROPHYLL DERIVATIVES

(75) Inventors: Avigdor Scherz, Rehovot (IL); Alexander Brandis, Rehovot (IL); Yoram Salomon, Rehovot (IL); Doron Eren, Netaim (IL); Avraham Cohen, Tel Aviv (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 1131 days.

(21) Appl. No.: 11/628,719

(22) PCT Filed: Jun. 7, 2005

(86) PCT No.: PCT/IL2005/000602
§ 371 (c)(1),
(2), (4) Date: Sep. 5, 2007

(87) PCT Pub. No.: WO2005/120573
PCT Pub. Date: Dec. 22, 2005

(65) Prior Publication Data
US 2008/0076748 A1    Mar. 27, 2008

(51) Int. Cl.
*A01N 55/02*   (2006.01)
*C07B 47/00*   (2006.01)
(52) U.S. Cl. ............... 514/185; 514/410; 540/145
(58) Field of Classification Search .............. 540/145; 514/145, 185
See application file for complete search history.

(56) References Cited

U.S. PATENT DOCUMENTS

| | | | |
|---|---|---|---|
| 5,726,169 | A | 3/1998 | Scherz et al. |
| 5,744,598 | A | 4/1998 | Skalkos et al. |
| 5,864,035 | A | 1/1999 | Pandey et al. |
| 5,955,585 | A | 9/1999 | Scherz et al. |
| 6,147,195 | A | 11/2000 | Scherz et al. |
| 6,569,846 | B1 | 5/2003 | Scherz et al. |
| 2003/0050296 | A1 | 3/2003 | Bommer et al. |
| 2003/0203888 | A1 | 10/2003 | Boyle et al. |

FOREIGN PATENT DOCUMENTS

| | | |
|---|---|---|
| DE | 10154436 | 5/2003 |
| WO | WO 00/33833 | 6/2000 |
| WO | WO 01/40232 | 6/2001 |
| WO | WO 03/028628 | 1/2002 |
| WO | WO 03/028629 | 4/2003 |
| WO | WO 03/055887 | 7/2003 |
| WO | WO 03/094695 | 11/2003 |
| WO | WO 2004/045492 | 6/2004 |

OTHER PUBLICATIONS

Eva M. Beems et al., "Photsensitizing Properties . . . ", Photochemistry and Photobiology, vol. 46, No. 5, pp. 639-643, 1987.*
Borle et al; Evaluation of the Photosensitizer Tookad® for Photodynamic Therapy on the Syrian Golden Hamster Cheek Pouch Model: Light Dose, Drug Dose and Drug-light Interval Effects; Photochem Photobiol; 2003; 377-383; 78 (4).
Chen et al; Preclinical Studies in Normal Canine Prostate of a Novel Palladium_Bacteriopheophorbide (WST09) Photosebsitizer for Photodynamic Therapy of Prostate Cancer; Photochem Photobiol; 2002; 438-445; 76.
Dellian et al; Vascular permeability in a human tumor xenograft: molecular charge dependence; Br J Cancer; 2000; 1513-1518; 82.
Dougherty, T. J. and J. G. Levy; Photodynamic Therapy (PDT) and Clinical Applications; Biochemical Phototonics Handbook. V. Tuan. Boca Raton, CRC Pressl LLC; 2003; 1-38; 38.
Elhilali; Initial Results of a Phase I/II Trial of WST09-Mediated Photodynamic Therapy (WST09-PDT) for Recurrent Prostate Cancer Following Failed External Beam Radiation Therapy (EBRT); XIXth EAU Congress, Workshop 1 "Vascular targeted photodynamic therapy for the treatment of prostate cancer: first clinical results with palladium bacteriopheophorbide (WST09)", Vienna; 2004.
Gross; Monitoring photodynamic therapy of solid tumors online by BOLD-contrast MRI; Nat Med; 2003; 1327-1331; 9.
Kelleher et al; Combined hyperthermia and chlorophyll-based photodynamic therapy: tumor growth and metabolic microenvironment; British Journal of Cancer; 2003; 2333-2339; 89.
Koudinova et al; Photodynamic Therapy With Pd-Bacteriopheophorbide (TOOKAD): Successful in Vivo Treatment of Human Prostatic Small Cell Carcinoma Xenografts; Int J Cancer; 2003; 782-789; 104.
Krammer B; Vascular effects of photodynamic therapy; Anticancer Res. 2001; 4271-7; 21(6B).
Mazor et al; Selective tumor vascular destruction of colon carcinoma xenografts by the hydrophilic Pd-bacteriochlorophyll derivative, WST11; 9th International Photodynamic Association; May 2003; Miyazaki, Japan, Book of Abstracts, p. 19.
Plaks et al; Photodynamic Therapy of Established Prostatic Adenocarcinoma with TOOKAD: A Biphasic Apparent Diffusion Coefficient Change as Potential Early MRI Response Marker; Neoplasia in Press; 2004.
Preise et al; Bypass of Tumor Drug Resistance by Antivascular Therapy; Neoplasia; 2003; 475-480; 5(6).
Rans et al: Increased Exposure of Anionic Phospholipids on the Surface of Tumor Blood Vessels; Cancer Research; 2002; 6132-6140; 62.
Rosenbach-Belkin et al; Serine Conjugations of Chlorophyll and Bacteriochlorophyll: Photocytotoxicity in vitro and Tissue Distribution on Mice Bearing Melanoma Tumors; Photochem Photobiol; 1996; 174-181; 64.

(Continued)

*Primary Examiner* — Paul V. Ward
(74) *Attorney, Agent, or Firm* — Browdy and Neimark, PLLC

(57) ABSTRACT

The invention provides cationic tetracyclic and pentacyclic bacteriochlorophyll derivatives (Bchls) containing at least one positively charged group and/or at least one basic group that is converted to a positively charged group under physiological conditions, preferably Bchls having an onium group derived from a N-containing aliphatic or heterocyclic radical such as ammonium, guanidinium, imidazolium, pyridinium, and the like or a phosphonium, arsonium, oxonium, sulfonium, selenonium, telluronium, stibonium, or bismuthonium group, or a basic group that is converted to such onium groups under physiological conditions, said groups being bound to one or more of the positions 17<3>, 13<3> and 3<2> of the Bchl molecule by ester or amide bond. The Bchls are useful for photodynamic therapy and diagnosis.

54 Claims, 10 Drawing Sheets

OTHER PUBLICATIONS

Schreiber S. et al; Local Photodynamic Therapy (PDT) of Rat C6 Glioma Xenografts with Pd-Bacteriopheophorbide Leads to decreased Metastases and increase of Animal Cure Compared with Surgery; International Journal of Cancer; 2002; 279-285; 99.

Zilberstein et al; Light-dependent Oxygen Consumption in Bacteriochlorophyll-Serine-treated Melanoma Tumors: On-line Determination Using a Tissue-inserted Oxygen Microsensor; Photochem Photobiol; 1997; 1012-1019; 65(6).

Zilberstein et al; Antivascular Treatment of Solid Melanoma Tumors with Bacteriochlorophyll-serine-based Photodynamic Therapy; Photochem Photobiol; 2001; 257-266; 73(3).

Brandis et al., "Novel Water-soluble Bacteriochlorophyll Derivatives for Vascular-targeted Photodynamic Therapy: Synthesis, Solubility, Phototoxicity and the Effect of Serum Proteins", Photochemistry and Photobiology, 81: 983-993 (2005).

Hargus et al., "Mono-(L)-aspartylchlorin-e6" Photochemistry and Photobiology, 83: 1006-1015 (2007).

Mazor et al., "WST11, A Novel Water-soluble Bacteriochlorophyll Derivative; Cellular Uptake, Pharmacokinetics, Biodistribution and Vascular-targeted Photodynamic Activity Using Melanoma Tumors as a Model" Photochemistry and Photobiology, 81: 342-351 (2005).

\* cited by examiner

PDT

Dark Control

Light Control

CATATONIC BACTERIOCHLOROPHYLL DERIVATIVES

FIELD OF THE INVENTION

The present invention relates to novel water-soluble cationic derivatives of bacteriochlorophyll, to their preparation and their use in methods of in vivo photodynamnic therapy and diagnosis of tumors and different vascular diseases such as age-related macular degeneration, as well as in in-vivo and ex-vivo methods of killing viruses and microorganisms.

Definitions and abbreviations: AMD: age-related macular degeneration; Bchl: bacteriochlorophyll a (pentacyclic 7,8,17,18-tetrahydroporphyrin with a $5^{th}$ isocyclic ring, a central Mg atom, a phytyl or geranylgeranyl group at position $17^3$, a $COOCH_3$ group at position $13^2$, an H atom at position $13^2$, methyl groups at positions 2, 7, 12, 18, an acetyl group at position 3, and an ethyl group at position 8); Bchlorin: bacteriochlorin (7,8,17,18-tetrahydroporphyrin); Bphe: bacteriopheophytin a (Bchl in which the central Mg atom is replaced by two H atoms); Bpheid: bacteriopheophorbide a (the $C-17^2$-free carboxylic acid derived from Bphe); Pd-Bpheid: Pd-bacteriopheophorbide a (the $C-17^2$-free carboxylic acid derived from Bphe with a central Pd atom); PDT: photodynamnic therapy; Rhodobacteriochlorin: Bchlorin having a —$CH_2CH_2COOH$ group at position 17, a COOH at position 13, methyl groups at positions 2, 7, 12, 18, and ethyl groups at positions 3 and 8.

IUPAC numbering of the Bchl derivatives is used throughout the specification. Using this nomenclature, the natural Bchls carry two carboxylic acid esters at positions $13^2$ and $17^2$, however they are esterified at positions $13^3$ and $17^3$.

BACKGROUND OF THE INVENTION

Photodynamic therapy (PDT) is a non-surgical technique for treatment of cancers and other diseases in which administration of a non-toxic photosensitizing agent (a drug that is activated by light), that is uptaken by and retained in a tumor or another tissue to be treated, is followed by non-hazardous irradiation with light of a particular wavelength that generates cytotoxic reactive oxygen species (singlet oxygen) in situ. This technique is more selective than conventional chemotherapy and radiotherapy because of preferential accumulation of photoactivatable compounds to tumor tissue and due to controlled light delivery directed toward the tumor that leads to spatially confined photodynamic effects.

Porphyrins have been employed as the primary photosensitizing agents in clinics. Optimal tissue penetration by light apparently occurs between 650-800 nm, but porfimer sodium (Photofrin®t, a trademark of Axcan Pharma Inc.), the world's first approved photodynamic therapy agent which is obtained from hematoporphyrin-IX by treatment with acids, and has received FDA approval for treatment of esophageal and endobronchial non-small cell lung cancers, absorbs only weakly at about 620 nm, and is a complex and inseparable mixture of monomers, dimers, and higher oligomers. In addition, Photofrin®g and other tested photosensitizing agents suffer from several deficiencies that limit their application, including mainly: (1) relatively weak absorption in the visible spectral range which limits the treatment to shallow tumors; (2) accumulation and long retention of the sensitizer in the patient's skin, leading to prolonged (days to months) skin phototoxicity; and (3) small or even no differentiation between the PDT effect on illuminated tumor and non-tumor tissues. These drawbacks and inherent problems have resulted in large amounts of work devoted to the synthesis of single pure compounds—so-called "second generation" sensitizers—which absorb at long wavelength, have well established structures and exhibit better differentiation between their retention in tumor cells and their retention in skin or other normal tissues.

In the search for appropriate light-sensitive molecules, or photosensitizers, bacteriochlorophyll appears to have some advantages over Photofrin®, the most common photosensitizer for PDT therapy. Bacteriochlorophyll, when illuminated, can cause the light to reach deeper into tissue, thereby being more effective for larger tumors. The spectra, photophysics, and photochemistry of native Bchls have thus made them optimal light-harvesting molecules with clear advantages over other photosensitizing agents presently used or tested in PDT treatment. In particular, these molecules have a very high extinction coefficient at long wavelengths ($\lambda_{max}$=760-780 nm, $\epsilon$=(4-10)×$10^4$ $M^{-1}$ $cm^{-1}$), where light penetrates deeply into tissues. They also generate reactive oxygen species (ROS) at a high quantum yield (depending on the central metal).

The biological uptake and PDT efficacy of metal-free derivatives of Bchl have been studied with the objective to manipulate the affinity of the sensitizers to the tumor cellular compartment. Cardinal to this approach is the use of highly lipophilic substituents that, on one hand, may increase the accumulation of the drug in the tumor cells but, on the other hand, may difficult its delivery to the tumor cells. In addition, one should avoid accumulation of significant phototoxic drug levels in non-tumor tissues over prolonged periods after administering the drug.

In applicant's previous U.S. Pat. No. 5,726,169, U.S. Pat. No. 5,955,585 and U.S. Pat. No. 6,147,195, a different approach was taken by the inventors. Highly efficient antivascular sensitizers, that do not extravasate from the circulation after administration and have short lifetime in the blood, were synthesized. It was expected that the inherent difference between vessels of normal and abnormal tissues such as tumors or other tissues that rely on neovessels, would enable relatively selective destruction of the abnormal tissue. Thus, it was aimed to synthesize Bchl derivatives that are more polar and hence have better chance to stay in the vascular compartment, where they convey the primary photodynamic effect. Manipulation at the 17-propionic acid residue site of the native Bchl provided conjugates with various residues such as amino acids, peptides or proteins, which enhance the sensitizer hydrophilicity. The vascular targeting activity of one of these derivatives, bacteriochlorophyll-serine, was studied as well as its fast clearance from the circulation and the entire animal body, lack of skin phototoxicity and high curative potential (Rosenbach-Belkin et al, 1996; Zilberstein et al., 1997; Zilberstein et al., 2001). Yet, these Mg-containing compounds were found unsuitable for pharmaceutical use due to their low stability on prolonged storage.

To increase the stability of the Bchl derivatives, the central Mg atom was replaced by Pd in the later applicant's PCT Publication WO 00/33833 and corresponding U.S. Pat. No. 6,569,846. This heavy atom was previously shown to markedly increase the oxidation potential of the Bchl macrocycle and, at the same time, to greatly enhance the intersystem-crossing (ISC) rate of the molecule to its triplet state. The metal replacement was performed by direct incorporation of $Pd^{2+}$ ion into a Bpheid molecule, as described in WO 00/33833. The first Pd-substituted Bchl derivative, palladium-bacteriopheophorbide or Pd-Bpheid (Tookad®, a trademark of Steba Biotech), was found highly effective against various solid tumors in pre-clinical studies (Schreiber et al., 2002; Gross et al., 2003; Koudinova et al., 2003; WO 03/094695) even against tumors comprising resistant tumor cells (Preise et al., 2003). The antivascular activity of Pd-Bpheid enabled destruction of the prostetic glandular tissue in dog models without compromising their continence (Chen et al., 2002). Phase I/II clinical trials proved that Pd-Bpheid is safe for use in the photodynamic therapy of prostate cancer in patients that failed radiation therapy (Elhilali, 2004) and induces necrosis and PSA (prostate specific antigen) reduction of vascularized glandular tissue in prostate patients treated with therapeutic light and drug doses (Trachtenberg, 2003).

Because of its low solubility in aqueous solutions, the clinical use of Pd-Bpheid requires the use of solubilizing agents such as Cremophor that may cause side effects at high doses. This lead the inventors to conceive a new family of Bchl derivatives, described in PCT/IL03/00973 (WO 2004/045492), consisting of the Bchlorin macrocycle containing a di- or trivalent central metal atom and at least two anionic residues. These anionic Bchl compounds can be administered intravenously after solubilization in aqueous solutions with no added excipients. Their short life-time in the circulation, combined with their relatively fast action and highly efficient anti-vascular activity, show their potential as antivascular PDT agents. In fact, one of these anionic Bchl derivatives is presently in preclinical studies for PDT of age-related macular degeneration (AMD) and liver tumors, e.g. hepatoma.

DE 10154436 describes pyrobacteriopheophorbide compounds for use in photodynamic therapy, in which at least one of the keto groups at position 3a or $13^1$ of the porphyrin system is derivatized to a corresponding imine.

WO 03/028629 describes chlorophyll derivatives that may contain positively charged ammonium or iminium groups for photodynamic therapy or diagnosis.

WO 03/028628 describes tetrapyrrolic macrocycles that are substituted by at least one functional group that comprises a carbamate group of the formula —OCON< or —OCON=C< and optionally contain positively charged ammonium or iminium groups, for photodynamic therapy or diagnosis. Although the general formulas disclosed in said publication include bacteriochlorophyll derivatives, it is to be noted that specific bacteriochlorophyll derivatives have not been disclosed nor does the specification teaches the preparation of bacteriochlorophyll derivatives.

It would be highly desirable to provide new bacteriochlorophyll derivatives that would be stable and would have enhanced affinity to endothelial cells for use in photodynamic therapy and, particularly, in vascular targeted phototherapy (VTP).

SUMMARY OF THE INVENTION

The present invention relates, in one aspect, to a bacteriochlorophyll derivative containing at least one positively charged group and/or at least one basic group that is converted to a positively charged group under physiological conditions, provided that said bacteriochlorophyll derivative has not a functional group that comprises a carbamate group and, when the bacteriochlorophyll derivative is a pyrobacteriopheophorbide, the at least one basic group that is converted to a positively charged group under physiological conditions is not an imine group at position 3a or $13^1$ of the bacteriochlorophyll molecule.

In another aspect, the present invention further relates to pharmaceutical compositions comprising a Bchl derivative as defined above and a pharmaceutically acceptable carrier, these compositions being useful for photodynamic therapy (PDT), particularly for vascular-targeting PDT, for example for PDT of tumors as well as for non-oncologic uses in the treatment of age-related macular degeneration (AMD), cardiovascular diseases and skin diseases such as acne and psoriasis. In addition, the compositions can be used for killing infectious agents comprising gram-negative or gram-positive bacteria and viruses in vivo or in vitro, as well as for diagnostic purposes.

The present invention still further relates to an improved method for photodynamic therapy using a photosensitizer, wherein the improvement consists of using as a photosensitizer a Bchl derivative of the invention. According to this aspect, the invention relates to a method for treatment by PDT, which comprises administering to an individual in need an effective amount of a Bchl derivative of the invention, followed by local irradiation.

In one embodiment, the method for treatment by PDT comprises administering to an individual suffering from a tumor an effective amount of a Bchl derivative of the invention, followed by local irradiation.

In another embodiment, the method for treatment by PDT comprises administering to an individual suffering from age-related macular degeneration an effective amount of a Bchl derivative of the invention, followed by local irradiation.

In a further embodiment, the present invention provides a method for preventing or reducing in-stent restenosis comprising administering to an individual suffering from a cardiovascular disease that underwent coronary angiography an effective amount of a Bchl derivative of the invention, followed by local irradiation.

The invention still further provides an improved method for diagnosis of tumors using a photosensitizer, wherein the improvement consists of using as a photosensitizer a Bchl derivative of the invention. According to this aspect, the invention relates to a method for diagnosis of tumors which comprises administering to an individual suspected of having a tumor an effective amount of a Bchl derivative of the invention, followed by local irradiation, e.g. perturbation with electromagnetic radiation of different wavelengths including short (e.g., X-rays), middle (e.g., UV/VIS/near-IR) to allow for optical frequency radiation, and long (e.g., radio frequency radiation) to enable, e.g., nuclear or electron paramagnetic resonance signals.

The invention yet still further provides an improved method for killing cells or infectious agents comprising bacteria and viruses, using a photosensitizer, wherein the improvement consists of using as a photosensitizer a Bchl derivative of the invention. According to this aspect, the invention relates to a method for sterilization of biological products, e.g. blood, which comprises adding to said biological product, e.g. blood, an effective amount of a Bchl derivative of the invention, followed by irradiation.

BRIEF DESCRIPTION OF THE FIGURES

The different compounds tested are represented in the following description of the drawings by a bold and underlined numeral. Their full identification is found in the List of Compounds at the beginning of the Chemical Section, in the Examples and in the Appendix hereinafter.

FIG. 3A: phototoxicity after 90 min incubation of the cells with increasing concentrations of compounds 5 and 11. FIG. 3B: phototoxicity after 2-hour incubation with increasing concentrations of compounds 5, 7 and 2. FIG. 3C: phototoxicity after 1-10 min incubation with compound 5 (50 µM). Cells were incubated in the dark with the indicated concentrations of the compounds, washed and illuminated for 10 min (open shapes in FIGS. 3A-B, closed shape in FIG. 3C) or kept in the dark (dark control, closed shapes in FIGS. 3A-B). Triplicate determinations were conducted and representative experiments are shown.

FIG. 6A: photographs of the tumor site in a PDT-treated animal at days 0, 4, 14, 21 and 32. FIG. 6B: photographs of the tumor site of dark control mice (injected with 5 but not illuminated) (n=3) at days 0 and 10; FIG. 6C: photographs of the tumor site of light control mice (injected with saline of a volume equivalent to the 5 solution and illuminated) (n=2) at days 0 and 10.

DETAILED DESCRIPTION OF THE INVENTION

Figure 1:
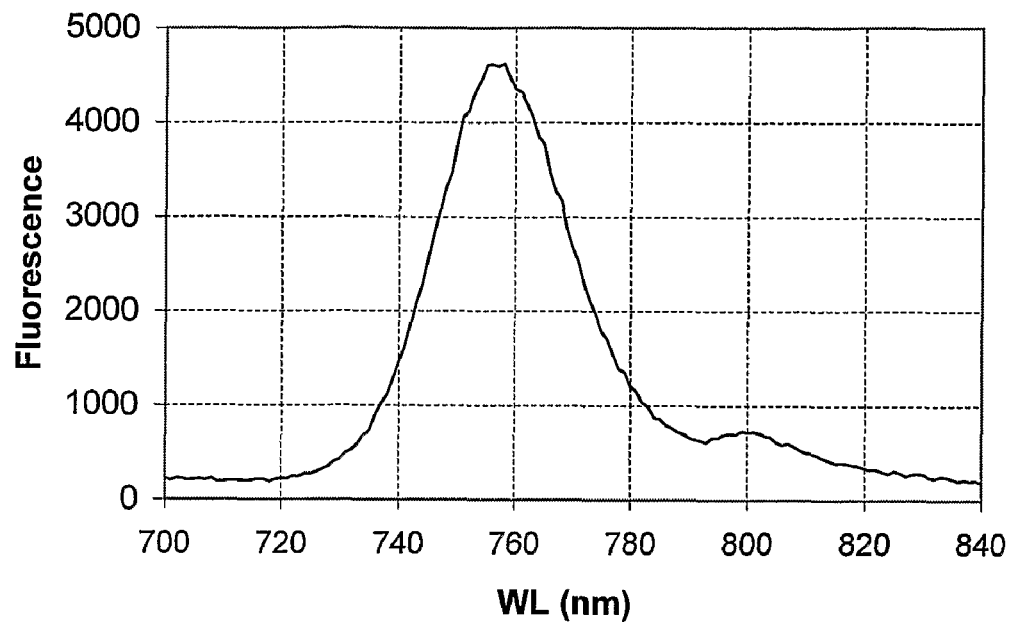
FIG. 1 shows the fluorescence emission spectrum of compound 5 in methanol.

The present invention derives from the observation by the present inventors that preclinical studies with Tookad® (Pd-Bpheid) and with a water-soluble anionic Bchl derivative (described in WO 2004/045492) demonstrated high efficacy in PDT of several solid tumors like melanoma, glioma, human prostate xenografts, normal canine prostate and DS Sarcoma in animal models (Chen et al., 2002; Schreiber et al., 2002; Gross et al., 2003; Kelleher et al., 2003; Koudinova et al., 2003; Mazor et al., 2003; Plaks et al, 2004) and indicated that the endothelial cells, the extracellular matrix and possibly platelets are probable candidates for the primary photodynamic action.

With the aforementioned Bchl derivatives, no evidence could be found for a direct action of the reactive oxygen species (ROS) formed during illumination on the tumor cells (Gross et al., 2003). Thus, the observed high cure rate seemed to indicate that photodynamic insult of the tumor endothelium could be sufficient to impose a complete tumor response. Following this observation, the inventors searched how to enhance the photosensitizer's affinity to endothelial cells and, particularly, to neoendothelial cells, which are characteristic to tumor and other vascular-dependent diseases. The suitable targets were identified as highly dense negative charges on the endothelium, including on the endothelial fenestrae, coated pits, plasmalemma proper and vesicles (Simionescu et al., 1981; Ghinea and Simionescu, 1985; Hamblin et al., 1999), fibroblast growth factor receptors (Segev et al., 2002), the endothelial glycocalyx (a highly hydrated mesh of membrane-bound negatively charged proteoglycans, glycosaminoglycans, glycoproteins, and glycolipids, some containing sulphonic groups), and angiogenic endothelial cells (Thurston et al., 1998; Dellian et al., 2000). In addition, recent publications pointed out to the increased exposure of anionic phospholipids on the surface of tumor endothelium, e.g., Hodgkins limphoma, human non-small cell lung carcinoma, mouse fibrosarcoma, human breast carcinoma and melanoma (Ran et al., 2002). The increased number of anionic sites in tumor endothelium provides an attractive target for tumor therapy.

The present invention relates, in a broad aspect, to a bacteriochlorophyll derivative containing at least one positively charged group and/or at least one basic group that is converted to a positively charged group under physiological conditions, provided that the bacteriochlorophyll derivative does not contain a functional group that comprises a carbamate group and, when the bacteriochlorophyll derivative is a pyrobacteriopheophorbide, the at least one basic group that is converted to a positively charged group under physiological conditions is not an imine group at position 3a or 13$^1$ of the bacteriochlorophyll molecule.

In one embodiment, the bacteriochlorophyll derivative of the invention contains at least one positively charged group, more preferably a cation derived from a N-containing group.

In a preferred embodiment, the at least one positively charged group is a cation derived from a N-containing group such as, but not limited to, an ammonium —N$^+$(R'R''), hydrazinium —(R)N—N$^+$(R'R''), ammoniumoxy O←N$^+$(RR')—, iminium>C═N$^+$(RR'), amidinium —C(—RN)—N$^+$R'R'' or guanidinium —(R)N—C(═NR)—N$^+$R'R'' group, wherein R, R' and R'' each independently is H, hydrocarbyl, or heterocyclyl, or two of R, R' and R'' together with the N atom to which they are attached form a 3-7 membered saturated ring, optionally containing one or more heteroatoms selected from the group consisting of O, S or N, and optionally further substituted at the additional N atom. It is to be understood that the positively charged N-containing group may be an end group, a group within a hydrocarbyl chain of the Bchl molecule or part of a saturated ring in which the N is protonated, as defined hereinafter. In addition, the at least one positively charged group may also be a cation derived from a N-containing heteroaromatic radical, as defined hereinafter.

In one preferred embodiment, the bacteriochlorophyll derivative contains an ammonium group of the formula —N$^+$(RR'R''), wherein each of R, R' and R'' independently is H, hydrocarbyl, preferably $C_1$-$C_{25}$ alkyl, more preferably $C_1$-$C_{10}$ or $C_1$-$C_6$ alkyl, or heterocyclyl. The —N$^+$(RR'R'') ammonium group may be a secondary ammonium group, wherein any two of the radicals R, R' or R" are H, a tertiary ammonium group, wherein only one of R, R' or R" is H, or a quaternary ammonium, wherein none of R, R' or R" is H. The ammonium group may be an end group or a group within a hydrocarbyl, preferably alkyl, chain. Preferably, the ammonium group is a quaternary ammonium group wherein R, R' and R" each independently is $C_1$-$C_6$ alkyl.

In another preferred embodiment, the bacteriochlorophyll derivative contains a cyclic ammonium group of the formula —$N^+$(RR'R"), wherein two of R, R' and R" together with the N atom form a 3-7 membered saturated ring, optionally containing a further heteroatom selected from the group consisting of O, S and N atom, and optionally further substituted at the additional N atom, as defined hereinafter. Examples of such cyclic ammonium groups include aziridinium, pyrrolidinium, piperidinium, piperazinium, morpholinium, thiomorpholinium, azepinium, and the like.

In a further embodiment, the bacteriochlorophyll derivative of the invention contains a cation derived from a N-heteroaromatic compound that may be a mono- or polycyclic compound that may further contain O, S or additional N atoms, as defined hereinafter.

In yet another embodiment, the bacteriochlorophyll derivative of the invention contains an onium group not containing N such as, but not limited to, a phosphonium [—P+(RR'R")], arsonium [—$As^+$(RR'R")], oxonium [—$O^+$(RR')], sulfonium [—$S^+$(RR')], selenonium [—$Se^+$(RR')], telluronium [—$Te^+$(RR')], stibonium [—$Sb^+$(RR'R")], or bismuthonium [—$Bi^+$(RR'R")] group, wherein each of R, R' and R", independently, is H, hydrocarbyl, or heterocyclyl. In preferred embodiments, R, R' and R" are H, $C_1$-$C_6$ alkyl such as methyl, ethyl, propyl, isopropyl, n-butyl, isobutyl, sec-butyl, pentyl or hexyl, an aryl group, preferably, phenyl, or an aralkyl group, such as benzyl and phenethyl.

In another embodiment, the bacteriochlorophyll derivative of the invention contains at least one basic group that is converted to a positively charged group under physiological conditions. As used herein, "physiological conditions" refer to the conditions in different tissues and cell compartments of the body.

In one embodiment, the basic group is an amino group of the formula —N(RR'), wherein each of R and R' independently is H, hydrocarbyl or heterocyclyl. The —N(RR') amino group may be a secondary amino, wherein only one of R and R' is H, or a tertiary amino wherein none of R and R' is H, or it is a cyclic amino wherein R and R' together with the N atom form a 3-7 membered saturated ring, optionally containing a further heteroatom selected from the group consisting of O, S and N atom, and optionally further substituted at the additional N atom, as defined hereinafter. It is to be understood that the basic amino group may be an end group, a group within a hydrocarbyl chain of the molecule or part of a N-containing 3-7 membered saturated ring such as aziridine, pyrrolidine, piperidine, piperazine, morpholine, thiomorpholine, azepine, and the like.

Further basic groups that are converted to a positively charged group under physiological conditions and can be used according to the invention will be defined hereinafter in the specification.

In still another embodiment, the bacteriochlorophyll derivative of the invention contains both at least one positively charged group and at least one basic group that is converted to a positively charged group under physiological conditions.

The bacteriochlorophyll derivative of the invention may be derived from a natural bacteriochlorophyll such as bacteriochlorophyll a or b, or from a synthetic non-natural derivative of bacteriochlorophyll, including compounds in which modifications have been made in the macrocycle, the central metal atom and/or in the periphery. The central Mg atom may be absent or replaced by other metal atom such as divalent Pd, Pt, Co, Sn, Ni, Cu, Zn or Mn, or trivalent Fe, Mn, Co, Au, Al, Gd, Er, Yb or Cr. In accordance with the present invention, the central metal atom is preferably absent or it is Pd.

In one preferred embodiment, the present invention provides a bacteriochlorophyll derivative of the formula I, II or III:

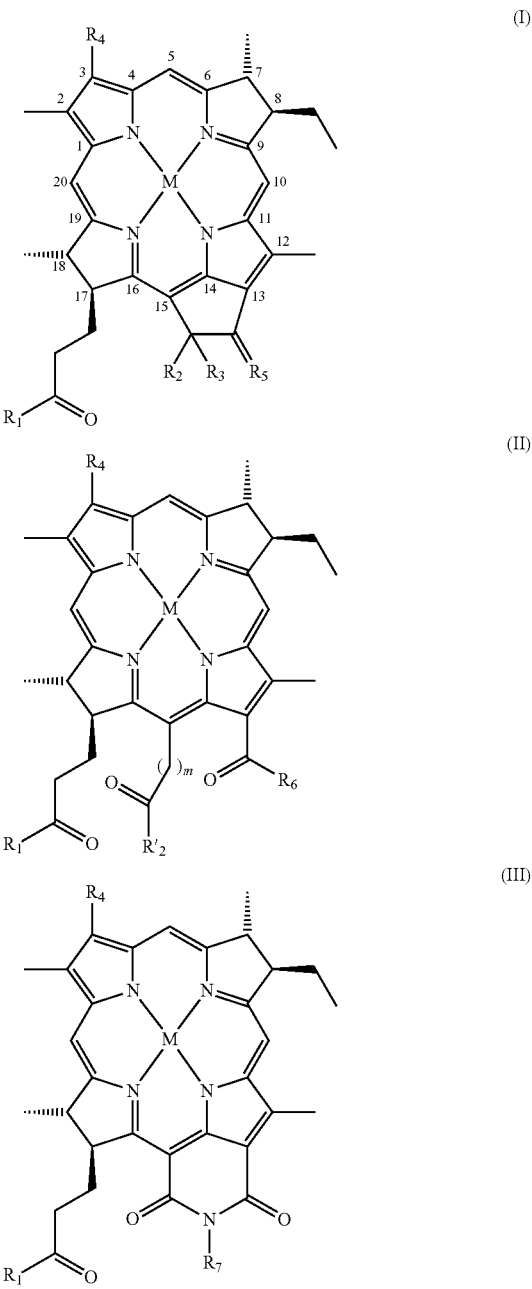

wherein
M represents 2H, a divalent metal atom selected from the group consisting of Pd, Pt, Co, Sn, Ni, Cu, Zn and Mn, or a trivalent metal atom selected from the group consisting of Fe, Mn, Co, Au, Al, Gd, Er, Yb and Cr;

$R_1$, $R'_2$ and $R_6$ each independently is Y—$R_8$, —$NR'_9R'_9$ or —$N^+R_9R'_9R''_9 A^-$;

Y is O or S;

$R_2$ is H, OH or $COOR_9$;

$R_3$ is H, OH, $C_1$-$C_{12}$ alkyl or $C_1$-$C_{12}$ alkoxy;

$R_4$ is —CH=$CR_9R'_9$, —CH=$CR_9$Hal, —CH=CH—$CH_2$—$NR_9R'_9$, —CH=CH—$CH_2$—$N^+R_9R'_9R'_9A^-$, —CHO, —CH=$NR_9$, —CH=$N^+R_9R'_9A^-$, —$CH_2$—$OR_9$, —$CH_2$—$SR_9$, —$CH_2$—Hal, —$CH_2$—$R_9$, —$CH_2$—$NR_9R'_9$, —$CH_2$—$N^+R_9R'_9R'_9A^-$, —$CH_2$—$CH_2R_9$, —$CH_2$—$CH_2$Hal, —$CH_2$—$CH_2OR_9$, —$CH_2$—$CH_2SR_9$, —$CH_2$—$CH_2$—$NR_9R'_9$, —$CH_2$—$CH_2$—$N^+R_9R'_9R'_9A^-$, —$COCH_3$, $C(CH_3)$=$CR_9R'_9$, —$C(CH_3)$=$CR_9$Hal, —$C(CH_3)$=$NR_9$, —$CH(CH_3)$=$N^+R_9R'_9A^-$, —$CH(CH_3)$—Hal, —CH$(CH_3)$—$OR_9$, —$CH(CH_3)$—$SR_9$, —$CH(CH_3)$—$NR_9R'_9$, —$CH(CH_3)$—$N^+R_9R'_9R'_9A^-$, or —C≡$CR_9$;

$R_5$ is =O, =S, =N—$R_9$, =$N^+R_9R'_9A^-$, =$CR_9R'_9$, or =$CR_9$—Hal;

$R_7$, $R_8$, $R_9$, $R'_9$ and $R'_9$ each independently is:

(a) H;

(b) $C_1$-$C_{25}$ hydrocarbyl;

(c) $C_1$-$C_{25}$ hydrocarbyl, preferably $C_1$-$C_{25}$ alkyl, more preferably $C_1$-$C_{10}$ or $C_1$-$C_6$ alkyl, substituted by one or more functional groups selected from the group consisting of halogen, nitro, oxo, OR, SR, epoxy, epithio, —CONRR', —COR, COOR'', —$OSO_3R$, —$SO_3R''$, —$SO_2R$, —$NHSO_2R$, —$SO_2NRR'$, =N—OR, —$(CH_2)_n$—CO—NRR', —O—$(CH_2)_n$—OR, —O—$(CH_2)_n$—O—$(CH_2)_n$—R, —$OPO_3RR'$, —$PO_2HR$, and —$PO_3R''R''$, wherein R and R' each independently is H, hydrocarbyl or heterocyclyl and R'' is hydrocarbyl or heterocyclyl;

(d) $C_1$-$C_{25}$ hydrocarbyl, preferably $C_1$-$C_{25}$ alkyl, more preferably $C_1$-$C_{10}$ or $C_1$-$C_6$— alkyl, substituted by one or more functional groups selected from the group consisting of positively charged groups, negatively charged groups, basic groups that are converted to positively charged groups under physiological conditions, and acidic groups that are converted to negatively charged groups under physiological conditions;

(e) $C_1$-$C_{25}$ hydrocarbyl, preferably $C_1$-$C_{25}$ alkyl, more preferably $C_1$-$C_{10}$ or $C_1$-$C_6$ alkyl, containing one or more heteroatoms and/or one or more carbocyclic or heterocyclic moieties;

(f) $C_1$-$C_{25}$ hydrocarbyl, preferably $C_1$-$C_{25}$ alkyl, more preferably $C_1$-$C_{10}$ or $C_1$-$C_6$ alkyl, containing one or more heteroatoms and/or one or more carbocyclic or heterocyclic moieties and substituted by one or more functional groups as defined in (c) and (d) above;

(g) $C_1$-$C_{25}$ hydrocarbyl, preferably $C_1$-$C_{25}$ alkyl, more preferably $C_1$-$C_{10}$ or $C_1$-$C_6$ alkyl, substituted by a residue of an amino acid, a peptide, a protein, a monosaccharide, an oligosaccharide, or a polysaccharide; or (h) a residue of an amino acid, a peptide, a protein, a monosaccharide, an oligosaccharide, or a polysaccharide;

$R_8$ may further be $H^+$ or a cation $R^+_{10}$ when $R_1$, $R'_2$ and $R_6$ each independently is Y—$R_8$;

$R^+_{10}$ is a metal, an ammonium group or an organic cation;

$A^-$ is a physiologically acceptable anion;

m is 0 or 1; and pharmaceutically acceptable salts and optical isomers thereof;

provided that, when in formula I $R_2$ and $R_3$ are both H, $R_5$ is not =N—$R_9$ and/or $R_4$ is not —$C(CH_3)$=$NR_9$; and further provided that the bacteriochlorophyll derivative of formula I, II or III has at least one positively charged group and/or at least one basic group that is converted to a positively charged group under physiological conditions.

As defined herein, $A^-$ is a physiologically acceptable anion such as chloride, bromide, iodide, perchlorate, sulfate, phosphate or an organic anion such as acetate, benzoate, caprylate, citrate, lactate, malonate, mandelate, mesylate, oxalate, propionate, succinate, tosylate, and the like.

The term "halogen" refers to fluoro, chloro, bromo or iodo.

The term "$C_1$-$C_{25}$ hydrocarbyl", as defined for $R_7$, $R_8$, $R_9$, $R'_9$, and $R'_9$, represents a straight or branched, saturated or unsaturated, acyclic or cyclic, including aromatic, hydrocarbyl radical of 1-25 carbon atoms, preferably of 1 to 20, more preferably of 1 to 6, carbon atoms.

In one preferred embodiment, the $C_1$-$C_{25}$ hydrocarbyl is a straight or branched $C_1$-$C_{25}$ alkyl radical, preferably $C_1$-$C_{10}$, and more preferably $C_1$-$C_6$ alkyl, e.g. methyl, ethyl, n-propyl, isopropyl, butyl, isobutyl, tert-butyl, pentyl, and hexyl. In another embodiment, the alkyl group has 10 carbon atoms or more, e.g. —$C_{10}H_{21}$, —$C_{15}H_{31}$, —$C_{16}H_{33}$, —$C_{17}H_{35}$, —$C_{18}H_{37}$, —$C_{20}H_{41}$, and the like. When $R_1$ is —$OR_8$, then $R_8$ may also be the geranylgeranyl (2,6-dimethyl-2,6-octadienyl) or phytyl (2,6,10,14-tetramethyl-hexadec-14-en-16-yl) radical, alkenyl groups that are present at the position $17^3$ of a natural chlorophyll or bacteriochlorophyll compound.

In another embodiment, the $C_1$-$C_{25}$ hydrocarbyl is a straight or branched $C_2$-$C_{25}$ alkenyl or alkynyl radical, preferably of 2-6 carbon atoms, e.g. vinyl, prop-2-en-1-yl, but-3-en-1-yl, pent-4-en-1-yl, hex-5-en-1-yl, ethynyl, propargyl, and the like.

In yet another embodiment, the $C_1$-$C_{25}$ hydrocarbyl is a $C_3$-$C_{25}$ monocyclic or polycyclic cycloalkyl, preferably $C_3$-$C_{14}$, more preferably $C_3$-$C_7$ cycloalkyl, such as cyclopropyl, cyclobutyl, cyclopentyl, cyclohexyl and cycloheptyl.

In a further embodiment, the $C_1$-$C_{25}$ hydrocarbyl is a monocyclic or polycyclic aryl radical, preferably a $C_6$-$C_{18}$, more preferably a $C_6$-$C_{14}$ aryl, such as phenyl, naphthyl, carbazolyl, anthryl, fluorenyl, indanyl, and phenanthryl.

In still a further embodiment, the $C_1$-$C_{25}$ hydrocarbyl is an aralkyl radical, wherein the aryl radical is preferably a $C_6$-$C_{18}$, more preferably a $C_6$-$C_{14}$ aryl, such as phenyl or naphthyl, and is more preferably benzyl or phenethyl.

As used herein, the term "carbocyclic moiety" refers to a monocyclic or polycyclic compound containing only carbon atoms in the ring(s). The carbocyclic moiety may be saturated, i.e. a cycloalkyl as defined above, or unsaturated, i.e. cycloalkenyl, or aromatic, i.e. an aryl as defined above.

The term "alkoxy" as used herein refers to a group ($C_1$-$C_{25}$)alkyl-O—, wherein $C_1$-$C_{25}$ alkyl is as defined above. Examples of alkoxy are methoxy, ethoxy, n-propoxy, isopropoxy, butoxy, isobutoxy, tert-butoxy, pentoxy, hexoxy, —$OC_{15}H_{31}$, —$OC_{16}H_{33}$, —$OC_{17}H_{35}$, —$OC_{18}H_{37}$, and the like. The term "aryloxy" as used herein refers to a group ($C_6$-$C_{18}$)aryl-O—, wherein $C_6$-$C_{18}$ aryl is as defined above, for example, phenoxy and naphthoxy.

The terms "heteroaryl" or "heterocyclic moiety" or "heteroaromatic" or "heterocyclyl", as used herein, mean a radical derived from a mono- or poly-cyclic heteroaromatic ring containing one to three heteroatoms selected from the group consisting of O, S and N. Particular examples are pyrrolyl, furyl, thienyl, pyrazolyl, imidazolyl, oxazolyl, thiazolyl, pyridyl, quinolinyl, pyrimidinyl, 1,3,4-triazinyl, 1,2,3-triazinyl, 1,3,5-triazinyl, benzofuryl, isobenzofuryl, indolyl, imidazo[1,2-a]pyridyl, benzimidazolyl, benzthiazolyl and benzoxazolyl.

Any "carbocyclic", "aryl" or "heteroaryl" may be substituted by one or more radicals such as halogen, $C_6$-$C_{14}$ aryl, $C_1$-$C_{25}$ alkyl, nitro, OR, SR, —COR, —COOR, —$SO_3R$, —$SO_2R$, —$NHSO_2R$, —NRR', —$(CH_2)_n$—NR—COR', and —$(CH_2)_n$—CO—NRR'. It is to be understood that when a polycyclic heteroaromatic ring is substituted, the substitutions may be in any of the carbocyclic and/or heterocyclic rings.

A "positively charged group" as used herein denotes a cation derived from a N-containing group or from an onium group not containing N.

A "cation derived from a N-containing group" as used herein denotes, for example, but is not limited to, an ammonium —$N^+(RR'R'')$, hydrazinium —$(R)N$—$N^+(R'R'')$, ammoniumoxy $O\leftarrow N^+(RR')$—, iminium>$C$=$N^+(RR')$, amidinium —$C(=RN)$—$N^+R'R''$ or guanidinium —$(R)N$—$C(=NR)$—$N^+R'R''$ group, wherein R, R' and R'' each independently is H, hydrocarbyl, preferably $C_1$-$C_6$ alkyl as defined herein, phenyl or benzyl, or heterocyclyl, or in the ammonium group one of R, R' and R'' may be OH, or two of R, R' and R'' in the ammonium group or R and R' in the hydrazinium, ammoniumoxy, iminium, amidinium or guanidinium groups, together with the N atom to which they are attached, form a 3-7 membered saturated ring, optionally containing one or more heteroatoms selected from the group consisting of O, S or N and optionally further substituted at the additional N atom, or said cation is derived from a compound containing one or more N atoms in a heteroaromatic ring.

In one more preferred embodiment, the bacteriochlorophyll derivative contains an ammonium group of the formula —$N^+(RR'R'')$, wherein each of R, R' and R'' independently is H or optionally substituted hydrocarbyl or heterocyclyl, as defined herein, or one of them may be OH. The —$N^+(RR'R'')$, ammonium group may be a secondary ammonium, wherein any two of the radicals R, R' or R'' are H; a tertiary ammonium, wherein only one of R, R' or R'' is H; or a quaternary ammonium, wherein each of R, R' or R'' is an optionally substituted hydrocarbyl or heterocyclyl group as defined herein. When one of R, R' or R'' is OH, the group is a hydroxylammonium group. Preferably, the ammonium group is a quaternary ammonium group wherein R, R' and R'' each is $C_1$-$C_6$ alkyl such as methyl, ethyl, propyl, butyl, hexyl. As mentioned hereinabove, the ammonium group may be an end group in the molecule or it may be found within an alkyl chain in the molecule.

In the hydrazinium —$(R)N$—$N^+(R'R'')$, amidinium —$C(=NR)$—$N^+R'R''$ and guanidinium —$(R)N$—$C(=NR)$—$N^+R'R''$ groups, R, R' and R'' may each independently be H or hydrocarbyl or heterocyclyl, or R' and R'' together with the N atom to which they are attached form a 3-7 membered saturated ring, as defined herein. Examples of such groups include those wherein R is H, and R' and R'' each is $C_1$-$C_6$ alkyl such as methyl, ethyl, propyl, butyl, hexyl.

In the ammoniumoxy $O\leftarrow N^+(RR')$— and iminium>$C$=$N^+(RR')$ groups, R and R' may each independently be H or hydrocarbyl, preferably $C_1$-$C_6$ alkyl, or heterocyclyl, or R and R' together with the N atom to which they are attached form a 3-7 membered saturated ring, as defined herein.

In another preferred embodiment, the bacteriochlorophyll derivative contains a cyclic ammonium group of the formula —$N^+(RR'R'')$, wherein two of R, R' and R'' together with the N atom form a 3-7 membered saturated ring defined hereinbelow.

As defined herein, "a 3-7 membered saturated ring" formed by two of R, R' and R'' together with the N atom to which they are attached may be a ring containing only N such as aziridine, pyrrolidine, piperidine, piperazine or azepine, or it may contain a further heteroatom selected from O and S such as morpholine or thiomorpholine. The further N atom in the piperazine ring may be optionally substituted by alkyl, e.g. $C_1$-$C_6$ alkyl, that may be substituted by halo, OH or amino. The onium groups derived from said saturated rings include aziridinium, pyrrolidinium, piperidinium, piperazinium, morpholinium, thiomorpholinium and azepinium.

As defined herein "a cation derived from a N-containing heteroaromatic radical" denotes a cation derived from a N-heteroaromatic compound that may be a mono- or polycyclic compound optionally containing O, S or additional N atoms. The ring from which the cation is derived should contain at least one N atom and be aromatic, but the other ring(s), if any, can be partially saturated. Examples of N-heteroaromatic cations include pyrazolium, imidazolium, oxazolium, thiazolium, pyridinium, pyrimidinium, quinolinium, isoquinolinium, 1,2,4-triazinium, 1,3,5-triazinium and purinium.

The at least one positively charged group may also be an onium group not containing nitrogen such as but not limited to, phosphonium [—$P^+(RR'R'')$], arsonium [—$As^+(RR'R'')$], oxonium [—$O^+(RR')$], sulfonium [—$S^+(RR')$], selenonium [—$Se^+(RR')$], telluronium [—$Te^+(RR')$], stibonium [—$Sb^+(RR'R'')$], or bismuthonium [—$Bi^+(RR'R'')$] group, wherein each of R, R' and R'', independently, is H, hydrocarbyl or heterocyclyl, preferably $C_1$-$C_6$ alkyl such as methyl, ethyl, propyl, butyl, pentyl or hexyl, or aryl, preferably, phenyl.

Examples of phosphonium groups of the formula —$P^+(RR'R'')$ include groups wherein R, R' and R'' each is methyl, ethyl, propyl, butyl or phenyl, or R is methyl, ethyl, propyl, butyl or hexyl and R' and R'' both are phenyl. Examples of arsonium groups of the formula —$As^+(RR'R'')$ include groups wherein R, R' and R'' each is methyl, ethyl, propyl, butyl or phenyl. Examples of sulfonium groups of the formula —$S^+(RR')$ include groups wherein R and R' each is methyl, ethyl, propyl, butyl, phenyl, benzyl, phenethyl, or a substituted hydrocarbyl group.

As defined herein, "a basic group that is converted to a positively charged group under physiological conditions" is, at least theoretically, any basic group that will generate under physiological conditions a positively charged group as defined herein. It is to be noted that the physiological conditions, as used herein, do not refer solely to the serum, but to different tissues and cell compartments in the body.

Examples of such N-containing basic groups include, without being limited to, any amino group that will generate an ammonium group, any imine group that will generate an iminium group, any hydrazine group that will generate a hydrazinium group, any aminooxy group that will generate an ammoniumoxy group, any amidine group that will generate an amidinium group, any guanidine group that will generate a guanidinium group, all as defined herein. Other examples include phosphino and mercapto groups.

Thus, the bacteriochlorophyll derivative of the invention may contain at least one basic group that is converted to a positively charged group under physiological conditions such as —NRR', —$C(=NR)$—NR'R'', —NR—NR'R'', —$(R)N$—$C(=NR)$—NR'R'', $O\leftarrow NR$—, or >$C$=$NR$, wherein each of R, R' and R'' independently is H, hydrocarbyl, preferably $C_1$-$C_{25}$ alkyl, more preferably $C_1$-$C_{10}$ or $C_1$-$C_6$ alkyl, or heterocyclyl, or two of R, R' and R'' together with the N atom form a 3-7 membered saturated ring, optionally containing an O, S or N atom and optionally further substituted at the additional N atom, or the basic group is a N-containing heteroaromatic radical.

The 3-7 membered saturated ring may be aziridine, pyrrolidine, piperidine, morpholine, thiomorpholine, azepine or piperazine optionally substituted at the additional N atom by $C_1$-$C_6$ alkyl optionally substituted by halo, hydroxyl or amino, and the N-containing heteroaromatic radical may be pyrazolyl, imidazolyl, oxazolyl, thiazolyl, pyridyl, quinolinyl, isoquinolinyl, pyrimidyl, 1,2,4-triazinyl, 1,3,5-triazinyl or purinyl.

As defined herein, —$R^+_{10}$ may be ammonium, a cation of a metal, preferably of an alkaline or earth alkaline metal such as Na, K, Li, Ca, Ba, or an organic cation as defined herein for "a cation derived from a N-containing group".

As defined herein, "a negatively charged group" is an anion derived from an acid and include carboxylate (COO$^-$), thio-carboxylate (COS$^-$), sulfonate (SO$_3^-$), and phosphonate (PO$_3^{2-}$), and the "acidic group that is converted to a negatively charged group under physiological conditions" include the carboxylic (—COOH), thio-carboxylic (—COSH), sulfonic (—SO$_3$H) and phosphonic (—PO$_3$H$_2$) acid groups. Bacteriochlorophyll derivatives with these radicals have been described in WO 2004/045492 of the same applicant, herewith incorporated by reference in its entirety as if fully disclosed herein.

As defined herein, R$_7$, R$_8$, R$_9$ and R'$_9$ each independently may be a C$_1$-C$_{25}$ hydrocarbyl optionally containing one or more heteroatoms, carbocyclic or heterocyclic moieties. For example, the C$_1$-C$_{25}$ hydrocarbyl may be a straight or branched C$_1$-C$_{25}$ alkyl or C$_2$-C$_{25}$ alkenyl that may be interrupted by one or more heteroatoms selected from O, S and/or N, and/or may be interrupted and/or substituted by one or more carbocyclic e.g. C$_3$-C$_7$-cycloalkyl or C$_6$-C$_{14}$-aryl, or heterocyclic moieties as defined above.

As defined herein, the C$_1$-C$_{25}$ hydrocarbyl defined for R$_7$, R$_8$, R$_9$ and R'$_9$ may optionally be substituted by one or more functional groups selected from halogen, nitro, oxo, OR, SR, epoxy, epithio, aziridine, —CONRR', —COR, COOR, —OSO$_3$R, —SO$_3$R, —SO$_2$R, —NHSO$_2$R, —SO$_2$NRR'—NRR', =N—OR, =N—NRR', —C(=NR)—NRR', —NR—NRR', —(R)N—C(=NR)—NRR', O←NR—, >C=NR, —(CH$_2$), —NR—COR', —(CH$_2$)$_n$—CO—NRR', —O—(CH$_2$)$_n$—OR, —O—(CH$_2$)$_n$—O—(CH$_2$)$_n$—R, —PRR', —OPO$_3$RR', —PO$_2$HR, PO$_3$RR'; one or more negatively charged groups such as COO$^-$, COS$^-$, —OSO$_3$, —SO$_3^-$, —OPO$_3$R$^-$, —PO$_2$H$^-$, —PO$_3^{2-}$ and —PO$_3$R$^-$; and/or one or more positively charged groups such as —P$^+$(RR'R"), —As$^+$(RR'R"), —O+(RR'), —S$^+$(RR'), —Se$^+$(RR'), —Te$^+$(RR'), —Sb$^+$(RR'R"), —Bi$^+$(RR'R"), O←N$^+$(RR')—, >C=N$^+$(RR'), —N$^+$(RR'R"), —(R)N—N$^+$(RR'R"), —(R)N—C(=HN)—N$^+$RR'R", —C(=NH)—N$^+$(RR'R"), or a N-heteroaromatic cation such as pyrazolium, imidazolium, oxazolium, thiazolium, pyridinium, quinolinium, pyrimidinium, 1,2,4-triazinium, 1,3,5-triazinium and purinium; wherein n is an integer from 1 to 6, R, R' and R" each independently is H, hydrocarbyl or heterocyclyl, or two of R, R' and R" together with the N atom to which they are attached form a 3-7 membered saturated ring, optionally containing one or more heteroatoms selected from the group consisting of O, S or N and optionally further substituted at the additional N atom. The C$_1$-C$_{25}$ hydrocarbyl defined for R$_7$, R$_8$, R$_9$ and R'$_9$ may also be substituted by the residue of a mono-, oligo- or polysaccharide such as glycosyl, or of an amino acid, peptide or protein. In addition, R$_8$, R$_9$ and R'$_9$ each may independently be a residue of a mono-, oligo- or polysaccharide such as glycosyl, or of an amino acid, peptide or protein In the groups OR and SR, when R is H, the groups hydroxy and mercapto are represented, respectively, and when R is other than H, ethers and sulfides are represented. In the group —PRR', the phosphino group is represented when R and R' are H. In the group —COR, when R is H, the formyl group —CHO of an aldehyde is represented, while when R is other than H, this is the residue of a ketone such as alkylcarbonyl and arylcarbonyl groups. In the group COOR, when R is not H, this is a carboxylic acid ester group such as the alkoxycarbonyl and aryloxycarbonyl groups. Similarly, esters are represented in the groups —OSO$_3$R, —SO$_3$R, —SO$_2$R, —OPO$_3$RR', —PO$_2$HR and —PO$_3$RR' when R and R' are other than H.

In one preferred embodiment, R$_1$ in the compound of formula I, or R$_1$ and R$^6$ in a compound of formula II, are a group —OR$_8$ wherein R$_8$ is a C$_1$-C$_6$ alkyl substituted by a positively charged end functional group, more preferably, a group —N$^+$RR'R", most preferably, —N$^+$(CH$_3$)$_3$.

In one embodiment of the invention, R$_7$, R$_8$, R$_9$ and/or R'$_9$ may be the residue of an amino acid, a peptide or a protein. In one preferred embodiment, R$_1$ at position 17$^3$ is —OR$_8$, wherein R$_8$ is the residue of an amino acid containing a free hydroxy group such as serine, threonine or tyrosine or an alkyl, e.g. methyl, ester thereof, or a peptide containing such amino acid or derivative thereof, said hydroxylated amino acid or derivatives thereof or peptide being linked to the —COO group of the Bchl derivative through its hydroxy group. Examples of such amino acid derivatives and peptides are L-serine methyl ester, L-tyrosine methyl ester, and seryl serine methyl ester.

In another preferred embodiment, the group —NR$_9$R'$_9$ is the residue of an amino acid containing a free amino group such as arginine and lysine, or a peptide containing them, or an alkyl ester derivative of said amino acid or peptide, linked to the —CO at position 13$^3$ and/or 17$^3$ of the Bchl molecule through an amide bond. In these compounds, the N atom of the —NR$_9$R'$_9$ group derives from the free amino group of the amino acid.

In a further embodiment, the C$_1$-C$_{25}$ hydrocarbyl group may be substituted by an amino acid residue and, if the terminal amino group of the amino acid is free, the amino acid residue may be the source of the positively charged group under physiological conditions.

R$^+_{10}$ may be a monovalent or divalent cation derived from an alkaline or alkaline earth metal such as K$^+$, Na$^+$, Li$^+$, NH$_4^+$, Ca$^+$, more preferably K$^+$; or it is a cation derived from an amine.

As used herein, the term "cationic derivative of bacteriochlorophyll" means a bacteriochlorophyll containing one or more positively charged groups and/or one or more basic groups that are converted to positively charged groups under physiological conditions. The bacteriochlorophyll molecule may also have neutral groups and/or one or more negatively charged groups and/or one or more acidic groups that are converted to negatively charged groups under physiological conditions. The overall charge of the bacteriochlorophyll molecule is not important.

In a more preferred embodiment, the bacteriochlorophyll derivative of the present invention is a rhodobacteriochlorin of the formula II:

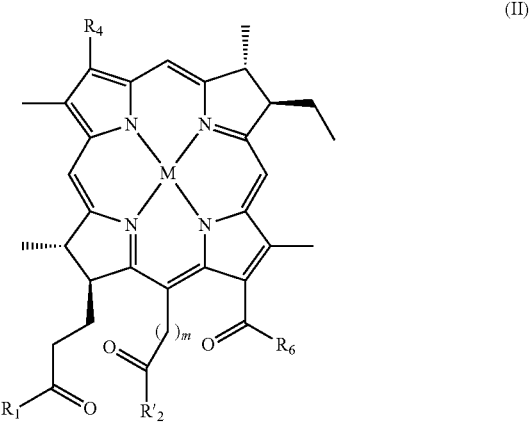

wherein

M represents 2H, a divalent metal atom selected from the group consisting of Pd, Pt, Co, Sn, Ni, Cu, Zn and Mn, or a trivalent metal atom selected from the group consisting of Fe, Mn, Co, Au, Al, Gd, Er, Yb and Cr;

$R_1$, $R'_2$ and $R_6$ each independently is $Y—R_8$, $—NR_9R'_9$, or $—N^+R_9R'_9R''_9A^-$;

Y is O or S;

$R_4$ is $—CH=CR_9R'_9$, $—CH=CR_9Hal$, $—CH=CH—CH_2—NR_9R'_9$, $—CH=CH—CH_2—N^+R_9R'_9R''_9A^-$, $—CHO$, $—CH=NR_9$, $—CH=N^+R_9R'_9A^-$, $—CH_2—OR_9$, $—CH_2—SR_9$, $—CH_2—Hal$, $—CH_2—R_9$, $—CH_2—NR_9R'_9$, $—CH_2—N^+R_9R'_9R''_9A^-$, $—CH_2—CH_2R_9$, $—CH_2—CH_2Hal$, $—CH_2—CH_2OR_9$, $—CH_2—CH_2SR_9$, $—CH_2—CH_2—NR_9R'_9$, $—CH_2—CH_2—N^+R_9R'_9R''_9A^-$, $—COCH_3$, $C(CH_3)=CR_9R'_9$, $—C(CH_3)=CR_9Hal$, $—C(CH_3)=NR_9$, $—CH(CH_3)=N^+R_9R'_9A^-$, $—CH(CH_3)—Hal$, $—CH(CH_3)—OR_9$, $—CH(CH_3)—SR_9$, $—CH(CH_3)—NR_9R'_9$, $—CH(CH_3)—N^+R_9R'_9R''_9A^-$ or $—C≡CR_9$;

$R_8$, $R_9$, $R'_9$ and $R'_9$ each independently is:

(a) H;

(b) $C_1$-$C_{25}$ hydrocarbyl;

(c) $C_1$-$C_{25}$ hydrocarbyl substituted by one or more functional groups selected from the group consisting of halogen, nitro, oxo, OR, SR, epoxy, epithio, $—CONRR'$, $—COR$, COOR, $—OSO_3R$, $—SO_3R$, $—SO_2R$, $—NHSO_2R$, $—SO_2NRR'$, $=N—OR$, $—(CH_2)_n—CO—NRR'$, $—O—(CH_2)_n—OR$, $—O—(CH_2)_n—O—(CH_2)_n—R$, $—OPO_3RR'$, $—PO_2HR$, and $—PO_3RR'$, wherein R and R' each independently is H, hydrocarbyl or heterocyclyl and R'' is hydrocarbyl or heterocyclyl;

(d) $C_1$-$C_{25}$ hydrocarbyl substituted by one or more functional groups selected from the group consisting of positively charged groups, negatively charged groups, basic groups that are converted to positively charged groups under physiological conditions, and acidic groups that are converted to negatively charged groups under physiological conditions;

(e) $C_1$-$C_{25}$ hydrocarbyl containing one or more heteroatoms and/or one or more carbocyclic or heterocyclic moieties;

(f) $C_1$-$C_{25}$ hydrocarbyl containing one or more heteroatoms and/or one or more carbocyclic or heterocyclic moieties and substituted by one or more functional groups as defined in (c) and (d) above;

(g) $C_1$-$C_{25}$ hydrocarbyl substituted by a residue of an amino acid, a peptide, a protein, a monosaccharide, an oligosaccharide, or a polysaccharide; or (h) a residue of an amino acid, a peptide, a protein, a monosaccharide, an oligosaccharide, or a polysaccharide;

$R_8$ may further be $H^+$ or a cation $R^+_{10}$, when $R_1$, $R'_2$ and $R_6$ each independently is $Y—R_8$;

$R^+_{10}$ is a metal, ammonium or an organic cation, $A^-$ is a physiologically acceptable anion;

m is 0 or 1; and pharmaceutically acceptable salts and optical isomers thereof; provided that the bacteriochlorophyll derivative of formula II has at least one positively charged group and/or at least one basic group that is converted to a positively charged group under physiological conditions.

In one preferred embodiment, $R_8$, $R_9$, $R'_9$ or $R''_9$ as defined in (a) above is a $C_1$-$C_{25}$ hydrocarbyl, preferably $C_1$-$C_6$ alkyl, unsubstituted or substituted by one or more functional groups selected from the group consisting of halogen, nitro, oxo, OR, SR, epoxy, epithio, aziridine, $—CONRR'$, $—COR$, COOR, $—COSR$, $—OSO_3R$, $—SO_3R$, $—SO_2R$, $—NHSO_2R$, $—SO_2NRR'$, $—NRR'$, $=N—OR$, $=N—NRR'$, $—C(=NR)—NR'R''$, $—NR—NR'R''$, $O\leftarrow NR—$, $>C=NR$, $—C(=NR)—N^+RR'$, $—(R)N—C(=NR)—N^+RR'$, $—(CH_2)_n—NR—COR'$, $—(CH_2)$, $—CO—NRR'$, $—O—(CH_2)_n—OR$, $—O—(CH_2)_n—O—(CH_2)_n—R$, $—PRR'$, $—OPO_3RR'$, $—PO_2HR$, $—PO_3RR'$; a negatively charged group such as $COO^-$, $COS^-$, $—SO_3^-$, $—OS_3^-$, $—PO_3^{2-}$, $—OPO_3R^-$, $—PO_2H^-$ and $—PO_3R^-$; a positively charged group such as $—P^+(RR'R'')$, $—As^+(RR'R'')$, $—O^+(RR')$, $—S^+(RR')$, $—Se^+(RR')$, $—Te^+(RR')$, $—Sb^+(RR'R'')$, $—Bi^+(RR'R'')$, $O\leftarrow N^+(RR')—$, $>C=N^+(RR')$, $—N^+(RR'R'')$, $—(R)N—N^+(RR')$, $—(R)N—C(=NR)—N^+RR'R''$, $—C(=NR)—N^+(RR'R'')$, and a N-heteroaromatic cation such as pyrazolium, imidazolium, oxazolium, thiazolium, pyridinium, quinolinium, isoquinolinium, pyrimidinium, 1,2,4-triazinium, 1,3,5-triazinium and purinium; wherein n is an integer from 1 to 6, R, R' and R'' each independently is H, hydrocarbyl or heterocyclyl, or two of R, R' and R'' together with the N atom to which they are attached form a 3-7 membered saturated ring, optionally containing one or more heteroatoms selected from the group consisting of O, S or N and optionally further substituted at the additional N atom; or the $C_1$-$C_{25}$ hydrocarbyl may be substituted by, or is by itself, the residue of a mono-, oligo- or polysaccharide such as glucosamine, or a residue of an amino acid, a peptide, or a protein.

In preferred embodiments, the Bchl derivative of the invention is a rhodobacteriochlorin of the formula II, wherein M is 2H or Pd; $R'_2$ is $—OR_8$ wherein $R_8$ is $C_1$-$C_6$ alkyl, preferably methyl; $R_4$ is $—COCH_3$; $R_1$ is OH, $—NR_9R'_9$, or $—NR_9—CH_2—CH(OH)—CH_2OH$; $R_6$ is $—NR_9R'_9$ or $—NR_9—CH_2—CH(OH)—CH_2OH$; $R_9$ is H or $C_1$-$C_6$ alkyl; and $R'_9$ is $C_1$-$C_{25}$ hydrocarbyl substituted by at least one positively charged group and/or at least one basic group that is converted to a positively charged group under physiological conditions.

In more preferred embodiments, in the above compounds $R_9$ is H and $R'_9$ is $C_1$-$C_{25}$ alkyl, preferably $C_1$-$C_{10}$, more preferably $C_1$-$C_6$ alkyl, substituted by at least one positively charged group $—N^+RR'R''$ or by at least one basic group $—NRR'$ and optionally interrupted by a $—N(R'')—$ group, wherein R and R' each independently is H, $C_1$-$C_6$ alkyl optionally substituted by NR''R''', or heterocyclyl such as pyridyl, or R and R' together with the N atom form a 6-membered ring further containing an O, S or N atom, and R'' is H or $C_1$-$C_6$ alkyl.

In one preferred embodiment, the present invention provides a bacteriochlorophyll derivative of formula II, wherein M is 2H or Pd; $R'_2$ is $—OR_8$ wherein $R_8$ is $C_1$-$C_6$ alkyl, preferably methyl; $R^4$ is $—COCH_3$; $R_1$ is OH and $R^6$ is a $—NHR'_9$ group selected from the group consisting of:

(i)

—NH—$(CH_2)_n$—NRR'  or  —NH—$(CH_2)_n$—N$^+$RR'R'';

(ii)

—NH—$(CH_2)_n$—N(R'')—$(CH_2)_n$—NRR';

(iii)

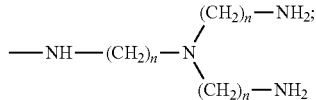

(iv)

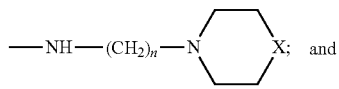

17

(v)

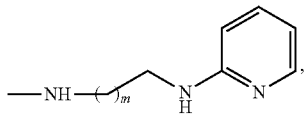

wherein
X is O, S or NR;
R, R' and R" each independently is H or $C_1$-$C_6$ alkyl;
n is an integer from 1 to 10, preferably 2 to 6; and
m is an integer from 1 to 6, preferably 1 to 3.

Examples of such bacteriochlorophyll derivatives are represented by the herein designated compounds 12 and 24-32.

In another preferred embodiment, the present invention provides a bacteriochlorophyll derivative of formula II, wherein M is 2H or Pd; $R'_2$ is —$OR_8$ wherein $R_8$ is $C_1$-$C_6$ alkyl, preferably methyl; $R_4$ is —$COCH_3$; and $R_1$ and $R_6$ are both the same —$NHR'_9$ group as defined above. Examples of such bacteriochlorophyll derivatives are represented by the herein designated compounds 4-11 and 33-45.

In a further preferred embodiment, the present invention provides a bacteriochlorophyll derivative of formula II, wherein M is 2H or Pd; $R'_2$ is —$OR_8$ wherein $R_8$ is $C_1$-$C_6$ alkyl, preferably methyl; $R_4$ is —$COCH_3$; $R_1$ is —NH—$CH_2$—CH(OH)—$CH_2$OH and $R_6$ is a —$NHR'_9$ group as defined above. Examples of such bacteriochlorophyll derivatives are represented by the herein designated compounds 48, 50, 55, 57, 59-64, 71 and 72.

In yet another preferred embodiment, the present invention provides a bacteriochlorophyll derivative of formula II, wherein M is 2H or Pd; $R'_2$ is —$OR_8$ wherein $R_8$ is $C_1$-$C_6$ alkyl, preferably methyl; $R_4$ is —$COCH_3$; $R_6$ is —NH—$CH_2$—CH(OH)—$CH_2$OH and $R_1$ is a —$NHR'_9$ group as defined above. Examples of such bacteriochlorophyll derivatives are represented by the herein designated compounds 46, 47, 49, 51, 56, 58, 73 and 74.

In yet a further preferred embodiment, the present invention provides a bacteriochlorophyll derivative of formula II, wherein M is 2H or Pd; $R'_2$ is —$OR_8$ wherein $R_8$ is $C_1$-$C_6$ alkyl, preferably methyl; $R_4$ is —$COCH_3$; $R_6$ is —NH—$CH_2$—$CH_2$—NRR'; and
$R_1$ is selected from the group consisting of
—NH—$(CH_2)_n$—OH;
—NH—CH(OH)—$CH_3$;
—NH—$(CH_2)$, —NR—$(CH_2)$, —OH; and
glycosylamino;
wherein R and R' each independently is H, methyl or ethyl; and n is 2 or 3.

Examples of such bacteriochlorophyll derivatives are represented by the herein designated compounds 65-70, and 75.

The compounds 4, 6, 8 and 10 and similar compounds of the invention having a basic group can be prepared by a method as depicted in Scheme I wherein Bpheid (compound A) or Pd-Bpheid (compound 1) is reacted with N-hydroxysuccinimide (NHS) in the presence of DCC, and the resulting Bpheid-NHS or Pd-Bpheid-NHS is reacted with an alkylenediamine of the formula $NH_2$—$(CH_2)_n$—$NH_2$.

The compounds 5, 7, 9, 11 and 12 and similar compounds of the invention having a positively charged group can be prepared by a method as depicted in Scheme I by reaction of a $13^1,17^3$-aminoalkylamide described above with the corresponding halide R—Hal, e.g. $CH_3I$. By HPLC purification of the product, different salts can be obtained depending on the buffer use for elution. Thus, citrate salts can be obtained by

18 elution with citrate buffer, phosphate salts can be obtained by elution with phosphate buffer, acetate salts can be obtained by elution with acetic acid, and so on.

In another preferred embodiment, the Bchl derivative of the invention is a rhodobacteriochlorin of the formula II, wherein M is Pd, $R'_2$ is —$OR_8$ wherein $R_8$ is $C_1$-$C_6$ alkyl, preferably methyl, $R_4$ is —$COCH_3$, and $R_1$ and/or $R_6$ are —$NR_9R'_9$, wherein $R_9$ is H and $R'_9$ is $C_1$-$C_{25}$ hydrocarbyl, preferably $C_1$-$C_{25}$ alkyl, more preferably $C_1$-$C_{10}$ alkyl, substituted by a guanidino or guanidinium group. In a more preferred embodiment of the invention, $R_1$ and $R^6$ are a group of the formula —NH—$(CH_2)$, —C(=NH)—$NH_2$ or —NH—$(CH_2)_n$—C(=NH)—$N^+(R)_3$ $A^-$, more preferably, —NH—$(CH_2)_n$—C(=NH)—$N(CH_3)_3{}^+A^-$, wherein n is an integer from 1 to 10, preferably 2, 3 or 6. Examples of such compounds are the $13^1,17^3$-guanidinoethylamide and $13^1,17^3$-trimethylguanidiniumethylamide herein designated compounds 14 and 14a respectively. The guanidine derivatives can be obtained as depicted in Scheme I by reaction of the $13^1,17^3$-aminoalkylamide with 1-amidinopyrazole, and the guanidinium derivative by further reaction with a methyl halide.

In another preferred embodiment, the Bchl derivative of the invention is a rhodobacteriochlorin of the formula II, wherein M is H or Pd, $R'_2$ is —$OR_8$ wherein $R_8$ is $C_1$-$C_6$ alkyl, preferably methyl, $R_4$ is —$COCH_3$, and $R_1$ and/or $R_6$ are —$NR_9R'_9$, wherein $R_9$ is H and $R'_9$ is $C_1$-$C_{25}$ hydrocarbyl, preferably $C_1$-$C_{25}$ alkyl, more preferably $C_1$-$C_{10}$ alkyl, substituted by a sulfonium group. In a more preferred embodiment of the invention, $R^1$ and $R^6$ are a group of the formula —NH—$(CH_2)_n$—$S^+(R)_2$ $A^-$, more preferably, —NH—$(CH_2)_n$—$S(CH_3)_2{+}A^-$, wherein n is an integer from 1 to 10, preferably 2, 3 or 6. An example of such compounds is the $13^1,17^3$-dimethylsulfoniumethylamide herein designated compound 15. This sulfonium derivative can be obtained by reaction of Bpheid or Pd-Bpheid with S,S-dimethylcysteamine diacetate.

In another preferred embodiment, the Bchl derivative of the invention is a rhodobacteriochlorin of the formula II, wherein M is H or Pd, $R'_2$ is —$OR_8$ wherein $R_8$ is $C_1$-$C_6$ alkyl, preferably methyl, $R_4$ is —$COCH_3$, and $R_1$ and/or $R_6$ are —$NR_9R'_9$, wherein $R_9$ is H and $R'_9$ is $C_1$-$C_{25}$ hydrocarbyl, preferably $C_1$-$C_{25}$ alkyl, more preferably $C_1$-$C_{10}$ alkyl, substituted by a phosphino or phosphonium group. In a more preferred embodiment of the invention, $R_1$ and $R^6$ are a group of the formula —NH—$(CH_2)$, —$P(R)_2$, more preferably, —NH—$(CH_2)_n$—$P(CH_3)_2$, or NH—$(CH_2)$, —$P^+(R)_3$ $A^-$, more preferably, —NH—$(CH_2)_n$—$P^+(CH_3)_3A^-$, wherein n is an integer from 1 to 10, preferably 2, 3 or 6. Examples of such compounds are the $13^1,17^3$-dimethylphosphinoethylamide, herein designated compound 18, and the $13^1,17^3$-trimethylphosphoniumethylamide, herein designated compound 17. The phosphino derivative is obtained by reaction of Bpheid-NHS with (2-aminoethyl)dimethylphosphine and the phosphonium derivative can be obtained by either by reaction of the phosphino derivative with alkyl halide, e.g. methyl iodide, or by reaction of a $13^1,17^3$-hydroxyethylamide derivative (compound 16) with trimethylphosphine.

In another preferred embodiment, the Bchl derivative of the invention is a rhodobacteriochlorin of the formula II, wherein M is H or Pd, $R'_2$ is —$OR_8$ wherein $R_8$ is $C_1$-$C_6$ alkyl, preferably methyl, $R_4$ is —$COCH_3$, and $R_1$ and/or $R_6$ are —$NR_9R'_9$, wherein $R_9$ is H and $R'_9$ is $C_1$-$C_{25}$ hydrocarbyl, preferably $C_1$-$C_{25}$ alkyl, more preferably $C_1$-$C_{10}$ alkyl, substituted by an arsino or arsonium group. In a more preferred embodiment of the invention, $R_1$ and $R^6$ are a group of the formula —NH—$(CH_2)_n$—$As(R)_2$, more preferably, —NH—

$(CH_2)_n$—$As(CH_3)_2$, or NH—$(CH_2)_n$—$As^+(R)_3 A^-$, more preferably, —NH—$(CH_2)_n$—$As^+(CH_3)_3 A^-$, wherein n is an integer from 1 to 10, preferably 2, 3 or 6. An example is the $13^1,17^3$-trimethylarsoniumethylamide, herein designated compound 19, that is obtained by reaction of a $13^1,17^3$-hydroxyethylamide derivative (compound 16) with trimethylamine.

In another preferred embodiment, the Bchl derivative of the invention is a rhodobacteriochlorin of the formula II, wherein M is 2H or Pd. $R'_2$ is —$OR_8$ wherein $R_8$ is $C_1$-$C_6$ alkyl, preferably methyl, $R_4$ is —$C(CH_3)$=$NR_9$, and $R_1$ and/or $R_6$ are —$NR'_9 R'_9$, wherein $R'_9$ is H and $R_9$ and $R'_9$ are $C_1$-$C_{25}$ hydrocarbyl, preferably $C_1$-$C_{25}$ alkyl, more preferably $C_1$-$C_{10}$ alkyl, substituted by at least one amino end group or a positively charged group, more preferably an ammonium end group of the formula —$N^+(RR'R'')A^-$, wherein R, R' and R" are preferably the same $C_1$-$C_6$-alkyl, preferably methyl, and $A^-$ is an anion. In a more preferred embodiment of the invention, $R_4$ is a group of the formula —$C(CH_3)$=N—$(CH_2)$, —$NH_2$ or —$C(CH_3)$=N—$(CH_2)_n$—$N(R)_3^+ A^-$ and $R_1$ and $R^6$ are a group of the formula —NH—$(CH_2)_n$—$NH_2$ or NH—$(CH_2)_n$—$N(R)_3^+ A^-$, more preferably, —NH—$(CH_2)_n$—$N(CH_3)_3^+ A^-$, wherein n is an integer from 1 to 10, preferably 2, 3 or 6. Examples of such compounds are the herein designated compounds 20, 21, 22 and 23.

In another preferred embodiment of the invention, the Bchl derivative is a bacteriochlorophyll of formula I:

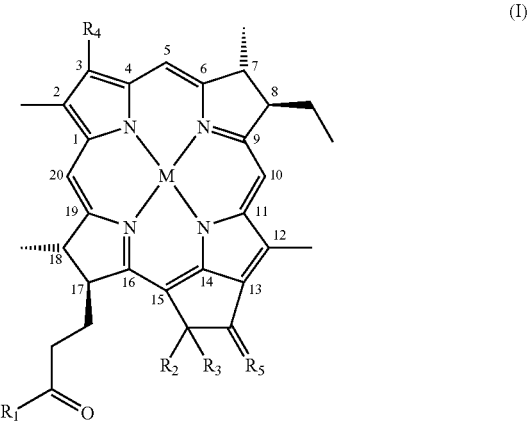

(I)

wherein

M represents 2H or a metal atom selected from divalent Pd, Pt, Co, Sn, Ni, Cu, Zn or Mn, and trivalent Fe, Mn, Co, Au, Al, Gd, Er, Yb or Cr;

$R_1$ is —$NR_9 R'_9$ or Y—$R_8$; Y is O or S; $R_2$ is H, OH or $COOR_9$;

$R_3$ is H, OH or $C_1$-$C_{12}$ alkyl or alkoxy;

$R_4$ is —CH=$CR_9 R'_9$, —CH=$CR_9$Hal, —CH=CH—$CH_2$—$NR_9 R'_9$, —CH=CH—$CH_2$—$N^+R_9 R'_9 R'_9 A^-$, —CHO, —CH=$NR_9$, —CH=$N^+ R_9 R'_9 A^-$, —$CH_2$—$OR_9$, —$CH_2$—$SR_9$, —$CH_2$—Hal, —$CH_2$—$R_9$, —$CH_2$—$NR_9 R'_9$, —$CH_2$—$N^+R_9 R'_9 R'_9 A^-$, —$CH_2$—$CH_2 R_9$, —$CH_2$—$CH_2$Hal, —$CH_2$—$CH_2 OR_9$, —$CH_2$—$CH_2 SR_9$, —$CH_2$—$CH_2$—$NR_9 R'_9$, —$CH_2$—$CH_2$—$N^+ R_9 R'_9 R''_9 A^-$, —$COCH_3$, $C(CH_3)$=$CR_9 R'_9$, —$C(CH_3)$=$CR_9$Hal, —$C(CH_3)$—$NR_9$, —$CH(CH_3)$—$N^+ R_9 R'_9 A^-$, —$CH(CH_3)$—Hal, —CH $(CH_3)$—$OR_9$, —$CH(CH_3)$—$SR_9$, —$CH(CH_3)$—$NR_9 R'_9$, —$CH(CH_3)$—$N^+ R_9 R'_9 R'_9 A^-$, or —C≡$CR_9$;

$R_5$ is =O, =S, =N—$R_9$, =$CR_9 R'_9$ or =$CR_9$—Hal;

$R_8$, $R_9$ and $R'_9$ each independently is H or selected from the group consisting of:

(a) $C_1$-$C_{25}$ hydrocarbyl; $C_1$-$C_{25}$ hydrocarbyl containing one or more heteroatoms, carbocyclic or heterocyclic moieties; $C_1$-$C_{25}$ hydrocarbyl substituted by one or more functional groups including one or more positively charged groups, one or more negatively charged groups, one or more basic groups that are converted to positively charged groups under physiological conditions or one or more acidic group that are converted to negatively charged groups under physiological conditions; or $C_1$-$C_{25}$ hydrocarbyl containing one or more heteroatoms, carbocyclic or heterocyclic moieties and substituted by one or more functional groups as defined hereinbefore;

(b) a residue of an amino acid, a peptide, a protein, or a mono- or poly-carbohydrate;

(c) when $R_1$ is Y—$R_5$, $R_8$ may further be $H^+$ or a cation $R^+_{10}$, wherein the cation $R^+_{10}$ is a metal, ammonium or an organic cation;

provided that when $R_2$ and $R_3$ are both H, $R_5$ is not =N—$R_9$ and/or $R_4$ is not —$C(CH_3)$=$NR_9$; and the bacteriochlorophyll molecule has at least one positively charged group and/or at least one basic group that is converted to a positively charged group under physiological conditions.

In a more preferred embodiment, the invention provides a Bchl derivative of the formula I wherein M is Pd, $R_2$ is —$COOCH_3$, $R_3$ is H, $R_4$ is —$COCH_3$, $R_5$ is =O, and $R_1$ is —$OR_8$, wherein $R_8$ is a residue of an amino acid containing an hydroxy group, preferably serine, or a derivative thereof, preferably an alkyl, more preferably methyl, ester, or a peptide containing said amino acid or derivative thereof, in which amino acid residue the free amino group may be quaternized as a trimethylammonium group. An example of such derivative of formula I is the herein designated compound 13.

The compounds of the invention, also referred herein sometimes by the terms "pigments" and "sensitizers-", present sufficient high polarity to be water-soluble and injected in aqueous solutions with no added surfactants. These compounds form small aggregates in $H_2O$/PBS solutions but undergo monomerization in the presence of serum albumin by being adsorbed on the protein (Mazor et al, 2003). Thus, trafficking of the compounds in and out of different cells is serum albumin dependent.

Figure 3A:
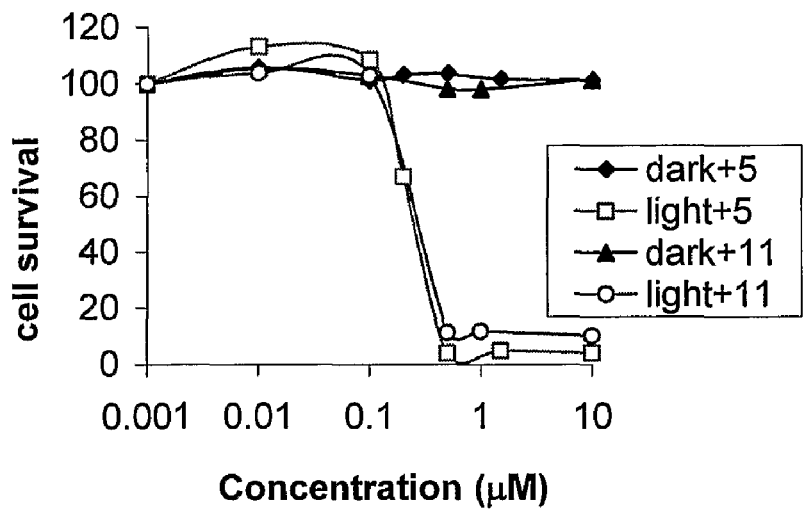
FIGS. 3A-3C are graphs showing the phototoxicity of compounds 5, 7, 9, and 11 on H5V endothelial cells.
Figure 3B:
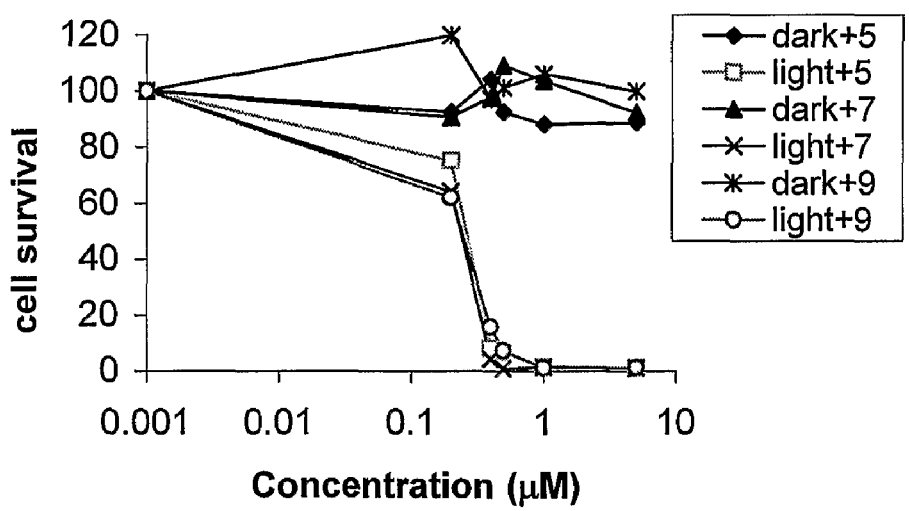
Figure 3C:
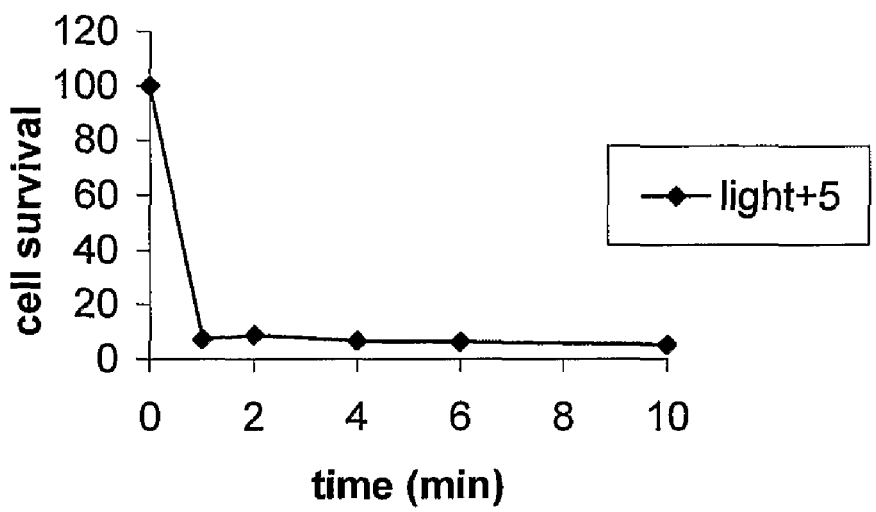
Figure 4:
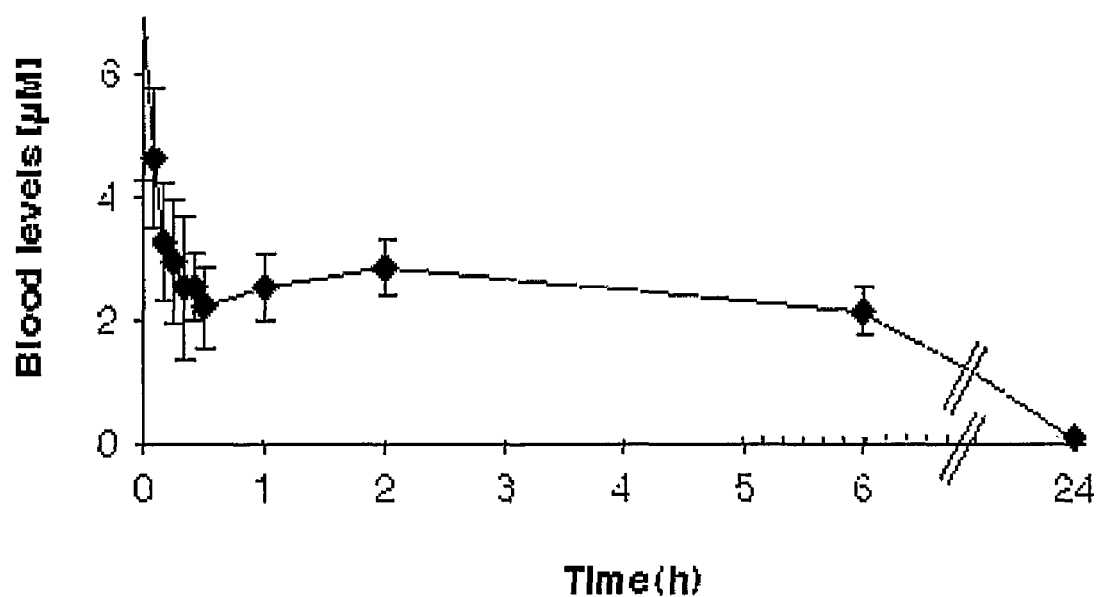
FIG. 4 is a graph showing the pharmacokinetics of compound 5 in Wistar rats blood. Following compound 5 intravenous (i.v.) injection (0.6 mg/kg), blood samples were collected from the same rat at 0, 5, 10, 15, 20, 30, 45 min and 1, 2, 6, 24 h after injection, and fluorescence emission spectra were recorded. Each time point represents average of three rats±STD.

In one embodiment, the biodistribution and pharmacokinetics for the preferred compound 5 are shown herein and, based thereon, it is assumed that this and the other derivatives of the invention remain in the circulation, and for a very short time. Furthermore, as shown in FIG. 3C herein, compound 5 reaches a very high PDT efficiency at less than 5 minutes of incubation with endothelial cell cultures. Therefore, the derivatives of the invention are good sensitizers for vascular-targeting PDT. Treatment of C6 glioma xenografts in mice, as shown herein in FIGS. 6 and 7, demonstrates that 5 is photodynamically active and causes tumor eradication at 10-fold lower concentrations than Pd-Bpheid (disclosed in WO 00/33833) or the negatively-charged Pd $3^1$-oxo-15-methoxycarbonylmethyl-Rhodobacteriochlorin 13'-(2-sulfoethyl) amide dipotassium salt (disclosed in WO 2004/045492). The suggested protocol with compound 5 considered the short clearance time of the drug (FIG. 4). Based on their high phototoxicity and selective effect on the tumor vasculature, these compounds can be used for the treatment of tumor as well as other tissue abnormalities that depend on neovascularization, and also against Gram-positive and Gram-negative bacteria.

Thus, in another aspect, the present invention provides a pharmaceutical composition comprising a BChl derivative of the invention or a pharmaceutically acceptable salt thereof and a pharmaceutically acceptable carrier.

In a preferred embodiment, the pharmaceutical composition comprises a Bchl derivative of formula I, II or III herein, more preferably a derivative of formula II bearing a quarternary ammonium group, most preferably, compound 5.

The new Bchl compounds of the invention have similar optical absorption and photophysical characteristics as the negatively charged Pd-Bchls disclosed in—PCT/IL03/00973 (WO 2004/045492) and very similar to that of Pd-Bpheid (WO 00/33833) and, therefore, once residing within the treated tissue, they are expected to be efficient photodynamic agents. They can thus be useful as photosensitizers and as therapeutic and diagnostic agents in many indications.

In one embodiment, the compounds of the invention are useful in the oncological field for treatment by PDT of pre-cancerous states and several cancer types such as, but not limited to, melanoma, prostate, brain, colon, ovarian, breast, chest wall tumors arising from breast cancer, skin, lung, esophagus and bladder cancers and other hormone-sensitive tumors. The compounds are useful for treatment of primary as well as metastatic tumors.

In another embodiment, the compounds of the invention are useful in non-oncological areas. Besides the efficient destruction of unwanted cells, like neoplasms and tumors, by PDT, the compounds of the invention can also be used against proliferating cells and bacteria. Proliferating cells and blood vessels are the main cause of arteriosclerosis, arthritis, psoriasis and macular degeneration. In addition, the compounds can be used in the treatment of non-malignant tumors such as benign prostate hypertrophy.

In one preferred embodiment, the compounds of the invention can be used in PDT for treatment of cardiovascular diseases mainly for vessel occlusion and thrombosis in coronary artery diseases, intimal hyperplasia, restenosis, and atherosclerotic plaques. In a more preferred embodiment, the compounds of the invention are used for preventing or reducing in-stent restenosis in an individual suffering from a cardiovascular disease that underwent coronary angiography. In another preferred embodiment, the compounds of the invention can be used in a method for the treatment of atherosclerosis by destruction of atheromatous plaque in a diseased blood vessel.

In another preferred embodiment, the compounds of the invention can be used in PDT for treatment of dermatological diseases, disorders and conditions such as acne, acne scarring, psoriasis, athlete's foot, warts, actinic keratosis, and port-wine stains (malformations of tiny blood vessels that connect the veins to the arteries (capillaries) located in the upper levels of the skin).

In another preferred embodiment, the compounds of the invention can be used in PDT for treatment of ophthalmic diseases, disorders and conditions such as corneal and choroidal neovascularization and, more preferably, age-related macular degeneration (AMD).

In a further preferred embodiment, the compounds of the invention can be used in PDT for killing of microorganisms including viruses, fungi and bacteria in samples and living tissues. For example, they can be used for sterilization of biological products such as blood and blood plasma for transfusion, followed by irradiation for destruction of infectious agents. As shown herein, compound 5 is active against both Gram-positive and Gram-negative bacteria (FIG. 8).

The novel water-soluble Bchl derivatives according to the invention sensitize endothelial and/or neoplastic cells or other abnormal tissues and lead to their destruction by irradiation either in vivo or ex vivo using light of appropriate wavelength. It is believed that the photoactivation energy is transferred to endogenous oxygen and converts it to singlet oxygen and/or other reactive oxygen species (ROS) such as superoxide and hydroxyl radicals, which are considered to be responsible for the cytotoxic effect. In addition, the photoactivated forms of some of these novel BChls fluoresce, which fluorescence can aid in localizing tumors or other sites to which the BChls are administered.

Due to their relatively short retention time in the circulation, the compounds of the invention are particularly suitable for vascular-targeting PDT (VTP), as described previously for Pd-Bpheid (Tookad®, a trademark of Steba Biotech) by the inventors and by others (WO 03/094695; Borle et al. 2003) and by the inventors for bacteriochlorophyll-serine (Zilberstein et al., 2001). In VTP, the anti-tumor activity of the bacteriochlorophyll derivative does not depend on direct photointoxication of individual endothelial cells but on the vascular tissue response to the VTP insult. Thus, with Tookad, the inventors have shown that photosensitization of Tookad by fiber-optic-guided transcutaneous illumination shortly after intravenous injection results in oxidative tumor vascular damage and depletion of oxygen, leading to termination of blood supply and tumor eradication In this aspect, it is envisaged by the invention also to use the compounds of the invention in combined hyperthermia and PDT for treatment of tumors as previously described (Kelleher et al., 2003).

The positive charges of the compounds of the invention significantly enhance the absorption of the novel Bchls to tumor endothelium as known in the art for other positively charged drugs that are used for therapy or for imaging of tumors (Dellian et al. 2000; Hashizume et al. 2000; Campbell et al. 2002). The enhanced affinity dramatically decreases the concentration needed for induction of endothelial cell-death at very short times of incubation, as required for vascular targeting PDT. Thus, these compounds enable reactive oxygen species (ROS) generation upon excitation that is limited to the interior vessels and, thereby, causes selective response of abnormal vessels such as those present in tumors and age-related macular degeneration.

The Bchl derivatives of the present invention have high affinity to serum albumin. A significant percentage of the compound molecules are non-covalently bound to serum albumin in the plasma. Thus, after purification and before injection, they allow to interact with serum albumin at a ratio of ~1:1 in aqueous solution.

For the preparation of the pharmaceutical compositions, the Bchls of the invention may be lyophilized, for example, with mannitol, and the dry powder is solubilized in saline or any other pharmaceutically acceptable aqueous solution for injection i.v. to a patient (in the blood, the compound is then adsorbed to the serum albumin) or for application on a sample in vitro target. The preparation of the compositions is carried out by techniques well-known in the art, for example as summarized in Remington: The Science and Practice of Pharmacy, Mack Publishing Co., Easton, Pa., 1990.

For diagnosis purposes, the Bchl derivatives may be used alone or may be labeled with a radioisotope or other detecting means such as paramagnetic metals, as known in the art. In one embodiment, the Bchl derivative is radioactively-labeled by standard procedures, e.g., using $^{67}$Ga, $^{111}$In, $^{201}$Tl, $^{99}$mTc, and is administered to the patient, preferably by i.v. injection. The locus of the cancer may be imaged by standard procedures, during a certain time interval following the administration.

The amount of Bchl derivative to be administered for PDT therapy will be established by the skilled physician according to the experience accumulated with other Bchl derivatives used in PDT, and will vary depending on the choice of the derivative used as active ingredient, the condition to be treated, the mode of administration, the age and condition of the patient, and the judgement of the physician.

The wavelength of the irradiating light is preferably chosen to match the maximum absorbance of the Bchl photosensitizer. The suitable wavelength for any of the compounds can be readily determined from its absorption spectrum. In a preferred embodiment, a strong light source is used, more preferably lasers at 720-790 nm.

Also envisaged by the present invention is conjugation of proteins such as serum albumin, recombinant serum albumin including human serum albumin and chimeric structures of human serum albumin (as described in Tuan et al. 2002), hormones, growth factors or their derivatives, antibodies, peptides that bind specifically to target cells receptors, particularly, endothelial cell receptors and nutrients, e.g. tyrosine, to the Bchl moiety, with the purpose of increasing their retention times in tumor and treated sites. Having the maximum optical absorption of the Bchl derivatives in the near-infra-red allows for a greater depth of penetration, while keeping the ubiquity of the natural system.

Replacement of the Mg ion by other metal ions is expected to optimize the intrinsic and metabolic stability of the Bchl moiety and its intersystem crossing to the excited triplet state, thus also expanding possibilities for new diagnostic procedures.

The combination of positively charged peripheral groups and/or neo-endothelium specific antibodies and/or peptides that have high affinity to neo-endothelial cells, will preferentially target the Bchl moieties to the tumor or treated site. As a result, the concentration of the photosensitizer in the vascular compartment of the malignant tissue is expected to increase dramatically relative to its concentration in the normal tissue, where cells are more dispersed, thus assuring amplification of the PDT effect in the tumor site. This enables effective use of light doses, lower than the damaging threshold of the normal tissue, thus reducing the need for spatially well-defined irradiation.

In one most preferred embodiment of the present invention, the target for treatment with the sensitizers of the invention are abnormal blood vessels, particularly blood vessels of solid tumors, age-related macular degeneration, restenosis, acute inflammation or atherosclerosis (Dougherty and Levy, 2003), due to the inherent difference of sensitivity of normal and abnormal blood vessels to the suggested PDT protocols described herein.

The Bchl derivatives of the invention may be further used in photodynamic therapy as an adjuvant to another current therapy used for the treatment of a disease, disorder or condition, to make it more effective. For example, they may be used intraoperatively in combination with surgery, to help prevent the recurrence of cancer on large surface areas such as the pleura (lining of the lung) and the peritoneum (lining of the abdomen), common sites of spread for some types of cancer, in intraoperative treatment of recurrent head and neck carcinomas, or following femoral artery angioplasty to prevent restenosis. The compounds may be also used in intraoperative PDT tumor diagnosis, for example, of brain tumors.

Another possibility according to the invention is to use the compounds of the invention in PDT of large solid tumors by interstitial therapy, a technique that involves feeding fiber optics directly into tumors using needles guided by computed tomography (CT). This may be especially useful in areas that require extensive surgery such as in head and neck tumors.

The amount of compound to be administered and the route of administration will be determined according to the kind of disease, stage of the disease, age and health conditions of the patient, but will be much lower than the currently used dosage of Photofrin II® (about 5-40 mg HpD/kg body weight) or Tookad® (about 2-10 mg/kg body weight).

The pharmaceutical compositions of the invention are administered to the patient by standard procedures used in PDT, for example, systemically, particularly by injection, more preferably by intravenous injection, locally by direct injection into the solid tumor, or topically for treatment of skin diseases and conditions.

The invention will now be illustrated by the following non-limiting Examples.

EXAMPLES

For convenience and better understanding, the section of the Examples is divided into two subsections: (I) the Chemical Section, describing the synthesis of the cationic and basic Bchl derivatives and intermediates 4-75, and (II) the Biological Section, describing the biological activity of the new Bchl derivatives.

I Chemical Section

In the Examples herein, the derivatives of the invention (4-75) and the intermediates (1-3) will be presented by their respective Arabic numbers in bold and underlined according to the following List of Compounds and the Appendix. The formulas of some of the compounds appear in the Schemes 1 and 2 and in the Appendix at the end of the description, just before the References.

LIST OF COMPOUNDS

1. Bacteriochlorophyll a (Bchl a)
2. Bacteriopheophorbide a (Bpheid)
3. Pd-Bacteriopheophorbide a (Pd-Bpheid)
4. $3^1$-oxo-15-methoxycarbonylmethyl-Rhodobacteriochlorin $13^1,17^{3'}$-di(2-amino ethyl)amide [Example 1]
5. $3^1$-oxo-15-methoxycarbonylmethyl-Rhodobacteriochlorin $13^1,17^3$-di(2-$N^3$-tri-methylammoniumethyl)amide dicitrate salt [Example 2]
6. $3^1$-oxo-15-methoxycarbonylmethyl-Rhodobacteriochlorin $13^1,17^3$-di(3-amino-propyl)amide [Example 3]
7. $3^1$-oxo-15-methoxycarbonylmethyl-Rhodobacteriochlorin $13^1,17^3$-di(3-$N^3$-trimethylammoniumpropyl)amide dicitrate salt [Example 4]
8. $3^1$-oxo-15-methoxycarbonylmethyl-Rhodobacteriochlorin $13^1,17^3$-di(6-aminohexyl)amide [Example 5]
9. $3^1$-oxo-15-methoxycarbonylmethyl-Rhodobacteriochlorin $13^1,17^3$-di(6-$N^3$-trimethylammoniumhexyl)amide dicitrate salt [Example 6]
10. Palladium $3^1$-oxo-15-methoxycarbonylmethyl-Rhodobacteriochlorin $13^1,17^3$-di(2-aminoethyl)amide [Example 7]
11. Palladium $3^1$-oxo-15-methoxycarbonylmethyl-Rhodobacteriochlorin $13^1,17^3$-di(2-$N^3$-trimethylammoniumethyl)amide diphosphate salt [Example 8]
12. Palladium $3^1$-oxo-15-methoxycarbonylmethyl-Rhodobacteriochlorin $13^1$-(2-$N^3$-trimethylammoniumethyl) amide chloride salt [Example 9]
13. O—[Pd-Bpheid]-[$N^3$-trimethylammonium-2-methyl]-Serine methyl ester iodide salt [Example 11]
14. Palladium $3^1$-oxo-15-methoxycarbonylmethyl-Rhodobacteriochlorin $13^1,17^3$-di(2-guanidinoethyl)amide [Example 12]

14a. Palladium $3^1$-oxo-15-methoxycarbonylmethyl-Rhodobacteriochlorin $13^1,17^3$-di(2-trimethylguanidiniumethyl)amide [Example 12]
15. Pd $3^1$-oxo-15-methoxycarbonylmethyl-Rhodobacteriochlorin $13^1$-(2-$S^2$-dimethylsulfoniumethyl)amide citrate salt [Example 13]
16. $3^1$-oxo-15-methoxycarbonylmethyl-Rhodobacteriochlorin $13^1,17^3$-di(2 hydroxyethyl)amide [Example 14]
17. $3^1$-oxo-15-methoxycarbonylmethyl-Rhodobacteriochlorin $13^1,17^3$-di(2-$P^3$-trimethylphosphoniumethyl)amide dicitrate salt [Example 15]
18. $3^1$-Oxo-15-methoxycarbonylmethyl-Rhodobacteriochlorin $13^1,17^3$-di(2-dimethylphosphinoethyl)amide [Example 16]
19. $3^1$-Oxo-15-methoxycarbonylmethyl-Rhodobacteriochlorin $13^1,17^3$-di(2-$As^3$-trimethylarsoniumethyl)amide dicitrate salt [Example 17]
20. $3^1$-(aminoethylimino)-15-methoxycarbonylmethyl-Rhodobacteriochlorin $13^1,17^3$-di(2-aminoethyl)amide
21. Palladium 31-(aminoethylimino)-15-methoxycarbonylmethyl-Rhodobacteriochlorin $13^1,17^3$-di(2-aminoethyl)amide
22. $3^1$-(trimethylammoniumethylimino)-15-methoxycarbonylmethyl-Rhodobacteriochlorin $13^1,17^3$-di(2-trimethylammoniumethyl)amide
23. Palladium $3^1$-(trimethylammoniumethylimino)-15-methoxycarbonylmethyl-Rhodobacteriochlorin $13^1,17^3$-di(2-trimethylammoniumethyl)amide Materials and Methods (i) Bpheid, 2, was prepared as previously described (Wasielewski and Svec, 1980).

(ii) Palladium bacteriopheophorbide (Pd-Bpheid, 3) was either prepared as previously described (WO 00/33833) or it was obtained from Steba Biotech Ltd. through Negma-Lerads, France.

(iii) Diamines (ethylenediamine, 1,3-propylenediamine, 1,6-hexylene-diamine) and trimethylphosphine (1M solution) were purchased from Aldrich (USA); N-hydroxysuccinimide (NHS) was purchased from Sigma (USA); 1,3-dicyclohexylcarbodiimide (DCC) and 1-amidinopyrazole hydrochloride were purchased from Fluka (Switzerland); trimethyl arsine was purchased from Sterm. (2-aminoethyl) dimethyl phosphine was prepared according to Suzuki et al. (1994) and Kinoshita et al. (1981). S,S-dimethylcysteamine diacetate was prepared according to U.S. Pat. No. 3,793,370.

(iv) Chemicals and solvents of analytical grade were generally used except when performing HPLC, where HPLC-grade solvents were applied.

(v) TLC: silica plates (Kieselgel-60, Merck, Germany); chloroform-methanol (4:1, v/v).

(vi) $^1$H Nuclear magnetic resonance (NMR) spectra were recorded on Avance DPX 250 instrument (Bruker, France) and reported in ppm (δ) downfield from tetramethylsilane, with residual solvent peaks as the internal standards.

(vii) The extinction coefficients of the Pd-derivatives were determined by correlating the Pd concentration (using flame photometry with $PdCl_2$ as a standard) with the optical density of the examined solution at the particular wavelength.

(viii) Electrospray ionization mass spectra (ESI-MS) were recorded on a platform LCZ spectrometer (Micromass, England).

(ix) Inductively-Coupled Plasma Mass Spectrometry (ICP-MS) was performed for determination of Pd concentrations using an ELAN-6000 instrument (Perkin Elmer, Conn.).

(x) Optical absorption (UV-VIS) spectra of the different complexes were recorded with Genesis-2 (Milton Roy, England) and V-570 (JASCO, Japan) spectrophotometers.

(xi) HPLC was performed using an LC-900 instrument (JASCO, Japan) equipped with a UV-915 diode-array detector.

CHEMICAL EXAMPLES

Example 1

$3^1$-Oxo-15-methoxycarbonylmethyl-Rhodobacteriochlorin $13^1,17^3$-di(2-aminoethyl)amide (Compound 4)

As depicted in Scheme I, for the synthesis of compound 4 (a rhodobacteriochlorin derivative in which the central metal atom is absent), Bpheid 2 was first activated at the $C$-$17^3$ carboxylic acid by N-hydroxysuccinimide (NHS) as follows: 50 mg of Bpheid (compound A), 80 mg of NHS and 65 mg of 1,3-dicyclohexylcarbodiimide (DCC) were mixed in methyl chloride overnight at room temperature. Then the solvent was evaporated under reduced pressure, the dry residue was dissolved in chloroform (ca. 50 ml), filtered from insoluble material, and, after evaporation of the solvent, the product, Bpheid-$17^3$-(1-oxy-succinimide), was obtained. The conversion was about 95% (TLC).

Eight mg (8 mg) of Bpheid-$17^3$-(1-oxy-succinimide) was dissolved in a mixture of chloroform and methanol (2:1, v:v), in order to enable the opening of the isocylic ring of Bpheid, and ethylenediamine (1 ml) was added. The reaction mixture was treated with Argon for 10 min and stirred at room temperature overnight in the dark, to enable binding of ethylenediamine at both the $13^1$ and $17^3$ positions. The reaction mixture was then evaporated to dryness under vacuum, re-dissolved in chloroform (50 ml) and washed once with water (about 50 ml) to discharge traces of ethylenediamine. The chloroform solution containing the product was collected and evaporated, thus obtaining the compound 4.

ESI-MS (+): 713.89 (M+1), 357.56 ([M+2]/2).

Optical absorption in chloroform, λ (relative absorption): 753 (1.00), 522 (0.28), 354 (1.05) nm.

Example 2

$3^1$-Oxo-15-methoxycarbonylmethyl-Rhodo-bacteriochlorin $13^1,17^3$-di(2-$N^3$-trimethylammoniumethyl) amide dicitrate salt (Compound 5)

Compound 5 was prepared from compound 4, as depicted in Scheme I. Diisopropylethylamine (DIEA) (27 μl) and methyl iodide (30 μl, $CH_3I$) were added to a solution of 4 (3 mg) in 2 ml of chloroform. The reaction mixture was treated with Argon for 10 min and stirred overnight at room temperature in the dark. The product was extracted twice with water (about 50 ml). The aqueous layer was collected and evaporated, and the product was purified by HPLC (HPLC JASCO, Japan). Column: C-8 250×20 (YMC, Japan). Solvent A: 0.05 M citrate buffer, pH 4.0. Solvent B: acetonitrile. The elution profile of title compound 5 as the dicitrate salt is described in Table 1. The fluorescence emission spectrum of compound 5 in methanol is shown in FIG. 1.

TABLE 1

| Gradient profile of purification of compound 5 | | | |
|---|---|---|---|
| Time (min) | Flow (ml/min) | A % | B % |
| 0 | 5 | 100 | 0 |
| 15 | 5 | 0 | 100 |
| 17 | 5 | 0 | 100 |

TABLE 1-continued

Gradient profile of purification of compound 5

| Time (min) | Flow (ml/min) | A % | B % |
|---|---|---|---|
| 22 | 5 | 100 | 0 |
| 30 | 0.2 | 100 | 0 |

ESI-MS (+): 990.12 (M-citrate).

NMR in MeOH-$d_4$: 9.33 (5-H, s), 8.92 (10-H, s), 8.75 (20-H, s), 5.35 and 4.95 ($15^1$-$CH_2$, br), 4.0-4.4 (7,8,17,18-H, m), 3.80 ($15^3$-Me, br s), 3.52 ($2^1$-Me, s), 3.19 ($12^1$-Me, s), 3.09 ($3^2$-Me, s), 1.92-2.41, 1.60-1.75 ($17^1$, $17^2$—$CH_2$, m), 2.19 ($8^1$—$CH_2$, m), 1.91 ($7^1$-Me, d), 1.61 ($18^1$-Me, d), 1.09 ($8^2$-Me, t), 3.62, 3.05 ($CH_2$'s of $NHCH_2CH_2NMe_3$), 3.39 and 3.02 (Me's of $NHCH_2CH_2NMe_3$).

Optical absorption in water, λ (relative absorption): 753 (1.00), 519 (0.30), 354 (1.25) nm. Octanol/water partition ratio is 40/60.

Example 3

$3^1$-Oxo-15-methoxycarbonylmethyl-Rhodobacteriochlorin $13^1$,$17^3$-di(3-aminopropyl)amide (Compound 6)

Compound 6 was obtained as described in Example 1 above by reaction of Bpheid-$17^3$-(1-oxy-succinimide) with 1,3-propylenediamine.

ESI-MS (+): 813.86 (M+$NH_2CH_2CH_2CH_2NH_2$), 739.74 (M).

Optical absorption in chloroform, λ (relative absorption): 753 (1.00), 522 (0.29), 354 (1.22) nm.

Example 4

$3^1$-Oxo-15-methoxycarbonylmethyl-Rhodobacteriochlorin $13^1$,$17^3$-di(3-$N^3$-trimethylammoniumpropyl) amide dicitrate salt (Compound 7)

Compound 7 was obtained from compound 6 by reaction with DIEA and $CH_3I$ as described in Example 2 above.

ESI-MS (+): 413.62 ([M-2×citrate]/2). Octanol/water partition ratio is 50/50.

Optical absorption in water, λ (relative absorption): 753 (1.00), 519 (0.29), 354 (1.21) nm.

Example 5

$3^1$-Oxo-15-methoxycarbonylmethyl-Rhodobacteriochlorin $13^1$,$17^3$-di(6-aminohexyl)amide (Compound 8)

Compound 8 was obtained as described in Example 1 above by reaction of Bpheid-$17^3$-(1-oxy-succinimide) with 1,6-hexylenediamine. Characteristics of compound 8:

ESI-MS (+): 826.20 (M+2), 413.62 ([M+2]/2)

Example 6

$3^1$-Oxo-15-methoxycarbonylmethyl-Rhodobacteriochlorin $13^1$,$17^3$-di(6-$N^3$-trimethylammoniumhexyl) amide dicitrate salt (Compound 2)

Compound 2 was obtained from compound 8 by reaction with DIEA and $CH_3I$ as described in Example 2 above.

ESI-MS (+): 455.89 ([M-2×citrate]/2). Octanol/water partition ratio is 75/25.

Optical absorption in water, λ (relative absorption): 753 (1.00), 519 (0.30), 354 (1.31) nm.

Example 7

Pd $3^1$-oxo-15-methoxycarbonylmethyl-Rhodobacteriochlorin $13^1$,$17^3$-di(2-aminoethyl)amide (Compound 10)

Compound 10 was obtained by reaction of Pd-Bpheid-$17^3$-(1-oxy-succinimide) with ethylenediamine as described in Example 1 above.

ESI-MS (+): 817.59 (M+1), 409.26 ([M+2]/2)

Optical absorption in MeOH (relative absorption): 747 (1.00), 516 (0.13), 384 (0.41), 330 (0.50) nm.

Example 8

Pd $3^1$-oxo-15-methoxycarbonylmethyl-Rhodobacteriochlorin $13^1$,$17^3$-di(2-$N^3$-trimethylammoniumethyl)amide diphosphate salt (Compound 11)

Compound 11 was obtained from compound 10 by reaction with DIEA and $CH_3I$ as described in Example 2 above but using phosphate buffer (0.05 M, pH 5.0) as Solvent A in the HPLC purification step.

ESI-MS (+): 451.38 ([M-2×phosphate]/2).

Optical absorption in water, λ (relative absorption): 747 (1.00), 516 (0.13), 384 (0.41), 330 (0.50) nm.

Example 9

Pd $3^1$-oxo-15-methoxycarbonylmethyl-Rhodobacteriochlorin $13^1$-(2-$N^3$-trimethylammoniumethyl) amide chloride salt (Compound 12)

As depicted in Scheme I, compound 3, Pd-Bpheid (10 mg), was stirred with 2-$N^3$-trimethylammonium-ethylamine chloride hydrochloride salt (15 mg) in DMF (2 ml), in the presence of triethylamine (0.5 ml) under Argon atmosphere at room temperature overnight, thus opening the isocyclic ring of the Bpheid molecule. Then the reaction mixture was evaporated to dryness, and the product was extracted with acetonitrile. After evaporation of the solvent, compound 12 was purified by HPLC under conditions similar to the purification of 5 in Example 2.

ESI-MS (+): 839 (M-Cl+Na—H), 817.82 (M-Cl) m/z.

Optical absorption in water, λ (relative absorption): 747 (1.00), 516 (0.13), 384 (0.41), 330 (0.50) nm.

Example 10

O—[Pd-Bpheid]-serine methyl ester

This compound was synthesized according to the procedure described in U.S. Pat. No. 6,333,319, as follows: Compound 3, Pd-Bpheid (50 mg), N-Trityl-L—Ser methyl ester (200 mg), DCC (16 mg, 0.08 mmol), and N-dimethylaminopyridine (DMAP) (10 mg) were dissolved in 20 ml dichloromethane and stirred overnight at room temperature under inert atmospheric (Argon) conditions. The resulting ester was purified by column chromatography on silica, with chloroform as eluent. The trityl-protecting group was removed by adding trifluoroacetic acid to the chloroform solution (to a final concentration of 1% vol) for 1-3 min, the reaction mixture was washed with water, dried over anhydrous sodium sulfate and evaporated to dryness. The deprotected product was purified on a silica column as follows: first, the major by-product was removed by elution with 5% acetone in chloroform, and then the product, O—[Pd-Bpheid]-Ser methyl ester, was eluted with 2% methanol in chloroform.

$^1$H-NMR in CDCl$_3$: 9.21 (s, 1H, H-α), 8.54 (s, 1H, H-β), 8.48 (s, 1H, H-δ), 5.93 (s, 1H, H-10), 4.37 (m, 2H, H-3,8), 4.22 (m, 1H, Ser-CH), 4.10 (m, 2H, H-4,7), 3.88 (s, 3H, CH$_3$-10b), 3.67 (s, 3H, Ser-OCH$_3$), 3.63 (m, 2H, Ser—CH$_2$), 3.48 (s, 3H, CH$_3$-1a), 3.39 (s, 3H, CH$_3$-5a), 3.09 (s, 3H, CH$_3$-2b), 2.48 (m, 1H, Ser-OH), 2.15-2.30 (m, 4H, CH$_2$-7a, 7b), 2.11 (m, 2H, CH$_2$-4-a), 1.78 (d, 3H, CH$_3$-3a), 1.68 (d, 3H, CH$_3$-8a), 1.08 (t, 3H, CH$_3$-4-b).

Example 11

O—[Pd-Bpheid]-[N$^3$-trimethylammonium-2-methyl]-serine methyl ester iodide salt (Compound 13)

The O—[Pd-Bpheid]-Ser methyl ester obtained in Example 10 above (4 mg) was dissolved in chloroform (3 ml) and stirred with methyl iodide (35 μl) and DIEA (30 μl) overnight at room temperature. The product 13 was obtained by evaporating the reaction mixture and purification on silica column with chloroform-methanol (3:1, v:v) as eluent.

ESI-MS (+): 872.75 (M−I) m/z.

Optical absorption in water, λ (relative absorption): 747 (1.00), 516 (0.13), 384 (0.41), 330 (0.50) nm.

Example 12

Pd 3$^1$-oxo-15-methoxycarbonylmethyl-Rhodobacteriochlorin 13$^1$,17$^3$-di(2-guanidinoethyl)amide (Compound 14)

As depicted in Scheme I, Pd 3$^1$-oxo-15-methoxycarbonylmethyl-Rhodobacteriochlorin 13$^1$,17$^3$-di(2-aminoethyl)amide, compound 10 (8 mg), was mixed with DIEA (30 μl) and 1-amidinopyrazole (6 mg) in chloroform-methanol (1:1, 15 ml). After stirring at room temperature for 20 h, the reaction mixture was evaporated, and the title compound 14 was purified by HPLC under conditions similar to the purification of compound 4 in Example 1.

ESI-MS (+): 451.69 ([M-2×citrate]/2).

By reaction of compound 14 with methyl iodide, the positively charged Palladium 3$^1$-oxo-15-methoxycarbonylmethyl-Rhodobacteriochlorin 13$^1$,17$^3$-di(2-trimethylguanidiumethyl)amide (14a) is obtained.

Example 13

Pd 3$^1$-oxo-15-methoxycarbonylmethyl-Rhodobacteriochlorin 13$^1$-(2-S$^2$-dimethylsulfoniumethyl)amide citrate salt (Compound 15)

Pd-Bpheid, 3 (12 mg) was stirred with S,S-dimethylcysteamine diacetate (20 mg) in DMF (2 ml), in the presence of triethylamine (0.5 ml) and under Argon atmosphere. The reaction mixture was evaporated to dryness, and the title compound 15 was purified by HPLC under conditions as described for compound 5 in Example 2.

ESI-MS (+): 844.78 (M-citrate+Na—H), 820.62 (M-citrate) m/z.

Example 14

3$^1$-oxo-15-methoxycarbonylmethyl-Rhodobacteriochlorin 13$^1$,17$^3$-di(2-hydroxyethyl)amide (Compound 16)

Bpheid-17$^3$-(1-oxy-succinimide) (10 mg), obtained as described in Example 1, was reacted with ethanolamine (1 ml) in a chloroform-methanol mixture (6 ml). The reaction mixture was treated with Argon for 10 min and stirred at room temperature overnight in the dark. Compound 16 was obtained following purification on silica column and elution with chloroform-methanol (10:1, vol/vol).

ESI-MS (+): 737.88 (M+Na), 715.42 (M+H) m/z.

Example 15

3$^1$-oxo-15-methoxycarbonylmethyl-Rhodobacteriochlorin 13$^1$,17$^3$-di(2-P$^3$-trimethylphosphoniumethyl) amide dicitrate salt (Compound 17)

Compound 16 (8 mg) was dissolved in trifluoroacetic anhydride (1 ml) and the mixture was evaporated to dryness after 30 min. The dry product was dissolved in a solution of trimethylphosphine in tetrahydrofuran (0.5 mM, 2 ml), and the mixture was stirred under Argon atmosphere at room temperature for 24 h. The reaction mixture was evaporated to remove excess trimethylphosphine, and the title compound 17 was obtained following purification by HPLC, under the conditions described for purification of 5 in Example 2.

ESI-MS (+): 438.54 ([M-2×citrate]/2+Na—H), 416.46 ([M-2×citrate]/2) m/z.

Example 16

3$^1$-Oxo-15-methoxycarbonylmethyl-Rhodobacteriochlorin 13$^1$,17$^3$-di(2-dimethylphosphinoethyl)amide (Compound 18)

Bpheid-17$^3$-(1-oxy-succinimide) (10 mg), obtained as described in Example 1, was reacted with (2-aminoethyl) dimethylphosphine (200 mg) in chloroform (5 ml) at room temperature overnight The title compound 18 was purified on silica column and eluted with chloroform-acetone (15:1, vol/vol).

ESI-MS (+): 825.34 (M+Na), 803.88 (M+H) m/z.

Treatment of compound 18 with methyl iodide in the presence of DIEA led to a product having quaternary phosphonium group which, after HPLC purification, was found identical to the compound 17 obtained in Example 15 above.

Example 17

3$^1$-Oxo-15-methoxycarbonylmethyl-Rhodobacteriochlorin 13$^1$,17$^3$-di(2-As$^3$-trimethylarsoniumethyl) amide dicitrate salt (Compound 19)

Compound 16 (8 mg) was dissolved in trifluoroacetic anhydride (1 ml) and the mixture was evaporated to dryness after 30 min. The dry product was dissolved in a solution of trimethylarsine in tetrahydrofuran (0.5 mM solution, 2 ml; prepared from pure reagent, Cat. No 33-3750, Strem), and the mixture was stirred under Argon atmosphere at 45° C., for 3 days. Then the mixture was evaporated to remove excess of trimethylarsine, and the title product 19 was purified by HPLC, under conditions as described for purification of 5 in Example 2.

ESI-MS (+): 1133.94 ([M-citrate]+Na—H), 460.40 ([M-2×citrate]/2) m/z.

Example 18

Palladium $3^1$-oxo-15-methoxycarbonylmethyl-Rhodobacteriochlorin-$13^1$-(2-$N^3$-trimethylammoniumethyl)amide acetate (salt) (Compound 14)

The chloride salt of this compound is described in Example 9 (compound 12).

For the preparation of the title compound, 20 mg of Pd-Bpheid, 3 (28 µmol), 24 mg of (2-aminoethyl)trimethylammonium chloride hydrochloride (137 µmol) and sodium ascorbate (1 µmol) were stirred at room temperature in 1 ml of a vacuum degassed mixture of 1:1 of triethylamine in DMF under argon atmosphere. At the end, the reaction mixture was evaporated in vacuum at room temperature, 1 ml of water was added and the product was loaded on a Sep-Pak RP-18 column (Waters) washed first with 20 ml of water, then with 10 ml of 10% solution of acetonitrile in water, then eluted with 50% solution of acetonitrile in water and evaporated. All the workup was done in the glove box under nitrogen atmosphere in order to avoid oxidation.

Formula structure: $C_{40}H_{54}N_6O_6Pd+1\ CH_3COO^-$
Molecular weight: 821.3+59.0
The product was analyzed by HPLC and MS identity confirmation.
Retention time: 13.05 min.
M.S(+): m/z=821
UV-Vis spectrum: 756 nm, 532 nm, 386 nm, 328 nm

Example 19

Palladium $3^1$-oxo-15-methoxycarbonylmethyl-Rhodobacteriochlorin-$13^1$-(2-$N^2$-dimethylaminoethyl)amide (Compound 15)

20 mg of Pd-Bpheid, 3 (28 µmol) and 1 ml (8.66 mmol) of N,N-Dimethyl ethylenediamine (95%), were stirred at room temperature for 2 hours under argon atmosphere. At the end of the reaction, the mixture was diluted with 3 ml of water and neutralized by glacial acetic acid. The product was purified by preparative HPLC, C-18 column, mobile phase: A=0.2% acetic acid in water. B=0.2% acetic acid in acetonitrile. Gradient: 20% B (0-6 min) to 95% B (30-33 min). Flow rate: 4 ml/min Formula structure: $C_{39}H_{50}N_6O_6Pd+1\ CH_3COOH$
Molecular weight: 803.3+60.0
The product was analyzed by HPLC and MS identity confirmation.
Retention time: 14.46 min.
M.S(+): m/z=803
UV-Vis-spectrum (MeOH): 748 nm, 521 nm, 384 nm, 332 nm

Example 20

Palladium $3^1$-oxo-15-methoxycarbonylmethyl-Rhodobacteriochlorin-$13^1$-(3-$N^2$-dimethylaminopropyl)amide (Compound 16)

20 mg of Pd-Bpheid, 3 (28 µmol) and 1 ml (7.88 mmol) of 3-dimethylamino-1-propylamine (99%), were stirred at room temperature for 2 hours under argon atmosphere. At the end of the reaction, the mixture was diluted with 5 ml of water and neutralized by glacial acetic acid. The product was purified by preparative HPLC, C-18 column, mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{40}H_{52}N_6O_6Pd+1\ CH_3COOH$
Molecular weight: 817.30+60.0
The product was analyzed by HPLC and MS identity confirmation.
Retention time: 14.26 min.
M.S(+): m/z=817
UV-Vis spectrum (MeOH): 749 nm, 516 nm, 380 nm, 334 nm

Example 21

Palladium $3^1$-oxo-15-methoxycarbonylmethyl-Rhodobacteriochlorin-$13^1$-(2-[(2-aminoethyl)amino]ethyl)amide (Compound 27)

20 mg of Pd-Bpheid, 3 (28 µmol) and 2 ml (18.35 mmol) of Diethylenetriamine (99%), were stirred at room temperature for 3 hours under argon atmosphere. The mixture was diluted with 5 ml of water and neutralized by glacial acetic acid. The product was purified by preparative HPLC, C-18 column, mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{39}H_{51}N_7O_6Pd+2\ CH_3COOH$
Molecular weight: 818.3+120.1
The product was analyzed by HPLC and MS identity confirmation.
Retention time: 12.91 min.
M.S(+): m/z=818.
UV-Vis spectrum (MeOH): 752 nm, 519 nm, 380 nm, 334 nm.

Example 22

Palladium $3^1$-oxo-15-methoxycarbonylmethyl-Rhodobacteriochlorin-$13^1$-([2-bis(2-aminoethyl)amino]ethyl)amide (Compound 28)

20 mg (28 Amos) of Pd-Bpheid, 3 were stirred with 1 ml (6.7 mmol) of tris-(2-aminoethyl)amine in 1 ml of N-methyl-2-pyrrolidone at room temperature under argon atmosphere during 90 minutes. The product was purified by injection to HPLC, containing a C-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{41}H_{56}N_8O_6Pd+3\ CH_3COOH$
Molecular weight: 861.4+180.1
The product was analyzed by HPLC and MS identity confirmation.
M.S(+): m/z=861.
UV-Vis spectrum (MeOH): 750 nm, 516 nm, 354 nm.

Example 23

Palladium $3^1$-oxo-15-methoxycarbonylmethyl-Rhodobacteriochlorin-$13^1$-(2-morpholino-N-ethyl)amide (Compound 29)

20 mg of Pd-Bpheid, 3 (28 µmol) and 1 ml (7.5 mmol) of N-(2-aminoethyl)morpholine (98%), were stirred at room temperature for 4 hours under argon atmosphere. At the end of the reaction, the mixture was diluted with 3 ml of water and neutralized by glacial acetic acid. The product was purified by preparative HPLC, C-18 column, mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{41}H_{52}N_6O_7Pd+1\ CH_3COOH$
Molecular weight: 845.3+60.0
The product was analyzed by HPLC and MS identity confirmation.
Retention time: 15.68 min.
M.S(+): m/z=845.
UV-Vis spectrum (MeOH): 749 nm, 516 nm, 383 nm, 331 nm.

Example 24

Palladium $3^1$-oxo-15-methoxycarbonylmethyl-Rhodobacteriochlorin-$13^1$-(2-piperazino-N-ethyl)amide (Compound 30)

20 mg of Pd-Bpheid, 3 (28 μmol) and 0.5 ml (3.7 mmol) of 1-(2-aminoethyl)piperazine (97%), were stirred at room temperature for 19 hours under argon atmosphere. At the end of the reaction, the mixture was diluted with 1 ml of water and neutralized by glacial acetic acid. The product was purified by preparative HPLC, C-18 column, mobile phase: A=0.2% acetic acid in water. B=0.2% acetic acid in acetonitrile. Gradient: 30% B (0-6 min) to 95% B (30-33 min). Flow rate: 4 nm/min.

Formula structure: $C_{41}H_{53}N_7O_6Pd+2\ CH_3COOH$
Molecular weight: 844.3+120.1
The product was analyzed by HPLC and MS identity confirmation.
Retention time: 14.37 min.
M.S(+): m/z=844
UV-Vis spectrum (MeOH): 747 nm, 516 nm, 380 nm, 330 nm

Example 25

Palladium $3^1$-oxo-15-methoxycarbonylmethyl-Rhodobacteriochlorin-$13^1$-(2-[(2-$N^2$-diethylaminoethyl)amino]ethyl)amide (Compound 31)

20 mg of Pd-Bpheid, 3 (28 μmol) and 1 ml (2.66 mmol) of N,N-diethyldiethylenetriamine (98%), were stirred at room temperature for 4 hours under argon atmosphere. At the end of the reaction, the mixture was diluted with 1 ml of water and neutralized by glacial acetic acid. The product was purified by preparative HPLC, C-18 column, mobile phase: A=0.2% acetic acid in water. B=0.2% acetic acid in acetonitrile. Gradient 30% B (0-6 min) to 95% B (30-33 min). Flow rate: 4 ml/min.

Formula structure: $C_{43}H_{59}N_7O_6Pd+2\ CH_3COOH$
Molecular weight: 874.4+120.1
The product was analyzed by HPLC and MS identity confirmation.
Retention time: 13.77 min.
M.S(+): m/z=874
UV-Vis spectrum (MeOH): 742 nm, 513 nm, 380 nm, 330 nm

Example 26

Palladium $3^1$-oxo-15-methoxycarbonylmethyl-Rhodobacteriochlorin-$13^1$-(3-[(3-aminopropyl)amino]propyl)amide (Compound 32)

Pd-Bpheid 3 (30 mg, 420 μmol) and bis(3-aminopropyl)amine (3 ml, 20.61 mmol) were stirred at room temperature for 2 hours under argon atmosphere. After reaction completion (TLC) the reaction mixture was diluted with water (100 ml), and the solution was extracted with n-butanol (twice, with 100 and 50 ml respectively) in a separation funnel. Butanolic extract was washed three times with 50 ml water. The phase separation was improved by adding 10-ml portions of 25% aqueous solution of NaCl. The butanolic extract was dried with $MgSO_4$ and evaporated under reduced pressure. The solid was re-dissolved in 10% aqueous acetic acid (10 ml), and the product was precipitated by addition of tenfold volume of acetone. The precipitate was re-dissolved in 0.5% aqueous acetic acid (13 ml) and lyophilized.

Formula structure: $C41H53N7O6Pd+2\ CH_3COOH$
Molecular weight: 846.5+120.1
The product was analyzed by HPLC and MS identity confirmation.
Retention time: 1-3.63 min.
M.S(+): m/z=846
UV-Vis spectrum (MeOH): 752 nm, 519 nm, 380 nm, 334 nm.

Example 27

Palladium $3^1$-oxo-15-methoxycarbonylmethyl-Rhodobacteriochlorin-$13^1$, $17^3$-di(2-$N^3$-trimethylammoniumethyl)amide diacetate salt (Compound 33)

The diphosphate salt of this compound is described in Example 8 (compound 11)

For the preparation of the title compound, 101 mg of Pd-Bpheid, 3 (141 μmol) and 10 ml of Ethylenediamine (148 mmol), were stirred at room temperature for 2 hours under argon atmosphere. Then, a solution of 659 mg of coupling reagent bromo-tris-pyrrolidino-phosphonium hexafluorophosphate (PyBroP) (1.4 mmol) in 2.3 ml of chloroform was introduced to the reaction. The mixture was stirred for another 2 hours at room temperature under argon atmosphere. Then the reaction was cooled, and excess of coupling reagent was destroyed by adding 5 ml of water. The mixture was diluted with 250 ml of chloroform and washed with 200 ml of water. The organic phase was dried over $MgSO_4$, filtered and evaporated. Approximately 245 mg of compound 10 was obtained.

Compound 10 (245 mg) was dissolved in 90 ml of chloroform. The reaction mixture was degassed by argon for about 5 min before introducing diisopropylethyl amine (DIEA) (2.6 ml, 14.88 mmol). After 5-min stirring, $CH_3I$ (2 ml, 31.8 mmol) was introduced to the reaction. A slow stream of argon was passed for further 2 min. The reaction was stirred at room temperature in the dark overnight.

After this time a moderate stream of argon was passed trough the reaction solution in order to remove unreacted $CH_3I$. The solvent was evaporated and the remaining product was dissolved in 350 ml of water and washed (4×100 ml) with ethyl acetate. The aqueous solution was concentrated by evaporation of water to a final volume of 150 ml.

The product was purified by 50-ml portions of aqueous solution on a Sep-Pack column, initially pre-washed with 120-ml of water and 200 ml of 1%-aqueous acetic acid, by elution with 5 ml of acetonitrile, containing 2% of acetic acid. acetonitrile solutions of several separations were combined, and the solvent was evaporated. The purified product was re-dissolved in 3 ml of water and lyophilized.

Formula: $C_{45}H_{66}N_8O_5Pd+2\ CH_3COO^-$
Molecular weight: 904.4+118.1

The product was analyzed by HPLC and MS identity confirmation.

Retention time: 11.35 min.

M.S(+): m/z=904

UV-Vis spectrum (MeOH): 747 nm, 514 nm, 382 nm, 330 nm

Example 28

Palladium $3^1$-oxo-15-methoxycarbonylmethyl-Rhodobacteriochlorin-$13^1$, $17^3$-di(3-aminopropyl) amide (Compound 34)

20 mg of Pd-Bpheid, 3 (28 μmol) and 2 ml (23.7 mmol) of freshly distilled 1,3-diaminopropane, were stirred at room temperature for 75 min. under argon atmosphere. After this time, a solution of 138.8 mg of PyBroP (297 μmol) in 200 μl of chloroform was introduced to the reaction vessel. The mixture was stirred for another 30 min. at room temperature under argon atmosphere. Then the reaction was cooled, and excess of coupling reagent was destroyed by adding 1 ml of water. The mixture was diluted with 50 ml of chloroform and washed with 2×100 ml of water. The organic phase was dried over MgSO$_4$, filtered and evaporated. The final product was purified by preparative HPLC, C-18 column, mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{41}H_{54}N_8O_5Pd+2\ CH_3COOH$

Molecular weight: 845.4+120.1

The product was analyzed by HPLC and MS identity confirmation.

Retention time: 10.81 min.

M.S(+): m/z=845

UV-Vis spectrum (MeOH): 745 nm, 514 nm, 380 nm, 330 nm

Example 29

Palladium $3^1$-oxo-15-methoxycarbonylmethyl-Rhodobacteriochlorin-$13^1$, $17^3$-di(4-aminobutyl) amide (Compound 35)

20 mg of Pd-Bpheid, 3 (28 μmol) and 2 ml (19.7 mmol) of 1,4-diaminobutane, were stirred at 30° C. for 1 hour under argon atmosphere. After this time, a solution of 133.4 mg of PyBroP (286 μmol) in 200 μl of chloroform was introduced to the reaction vessel. The mixture was stirred for another 60 min. at 30° C. under argon atmosphere. Then the reaction was cooled, and excess of coupling reagent was destroyed by adding 1 ml of water. The excess of amine was evaporated and the product was purified by preparative HPLC, C-18 column, mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{43}H_{58}N_8O_5Pd+2\ CH_3COOH$

Molecular weight: 873.2+120.1

The product was analyzed by HPLC and MS identity confirmation.

Retention time: 5.11 min.

M.S(+): m/z=873

UV-Vis spectrum (MeOH): 748 nm, 516 nm, 384 nm, 332 nm

Example 30

Palladium $3^1$-oxo-15-methoxycarbonylmethyl-Rhodobacteriochlorin-$13^1$, $17^3$-di(2-aminoethyl) amide (Compound 10)

20 mg of Pd-Bpheid, 3 (28 μmol) and 2 ml (29.6 mmol) of Ethylenediamine, were stirred at room temperature for 40 min. under argon atmosphere. After this time, a solution of 136.8 mg of PyBroP (293 μmol) in 200 μl of chloroform was introduced to the reaction vessel. The mixture was stirred for another 2 hours at room temperature under argon atmosphere. Then the reaction was cooled, and excess of coupling reagent was destroyed by adding 2 ml of water. The reaction mixture was diluted with 50 ml of chloroform and washed twice with 100 ml of water. The solvent was evaporated and the final product was purified by preparative HPLC, C-18 column, mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{39}H_{50}N_8O_5Pd+2\ CH_3COOH$

Molecular weight: 817.3+120.1

The product was analyzed by HPLC and MS identity confirmation.

Retention time: 10.13 min.

M.S(+): m/z=817

UV-Vis spectrum (MeOH): 750 nm, 516 nm, 384 nm, 332 nm

Example 31

Palladium $3^1$-oxo-15-methoxycarbonylmethyl-Rhodobacteriochlorin-$13^1$, $17^3$-di(2-$N^2$-dimethylaminoethyl)amide (Compound 36)

20 mg of Pd-Bpheid, 3 (28 μmol) and 1.5 ml (13 mmol) of N,N-dimethylethylenediamine, were stirred at room temperature for 1 hour under argon atmosphere. After this time, a solution of $13^1$ mg of PyBroP (281 μmol) in 170 μl of chloroform was introduced to the reaction vessel. The mixture was stirred for another 2 hours at room temperature under argon atmosphere. Then the reaction was cooled, and excess of coupling reagent was destroyed by adding 1 ml of water. The reaction mixture was diluted with 50 ml of ethyl acetate and washed twice with 100 ml of water. The solvent was evaporated and the final product was purified by preparative HPLC, C-18 column, mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{43}H_{58}N_8O_5Pd+2\ CH_3COOH$

Molecular weight: 873.2+120.1

The product was analyzed by HPLC and MS identity confirmation.

Retention time 6-0.56 min.

M.S(+): m/z=873

UV-Vis spectrum (MeOH): 748 nm, 516 nm, 384 nm, 332 nm

Example 32

Palladium $3^1$-oxo-15-methoxycarbonylmethyl-Rhodobacteriochlorin-$13^1$, $17^3$-di(3-$N^2$-dimethylaminopropyl)amide (Compound 37)

20 mg of Pd-Bpheid, 3 (28 μmol) and 1.5 ml (11.8 mmol) of 3-dimethylamino-1-propylamine, were stirred at room temperature for 1 hour under argon atmosphere. After this time, a solution of 130.6 mg of PyBroP (280 μmol) in 170 μl of chloroform was introduced to the reaction vessel. The mixture was stirred for another 2 hours at room temperature under argon atmosphere. Then the reaction was cooled, and excess of coupling reagent was destroyed by adding 1 ml of water. The reaction mixture was diluted with 50 ml of ethyl acetate and washed twice with 100 ml of water. The water layers were washed with 100 ml ethyl acetate. Both organic layers were joined and evaporated. The final product was purified by preparative HPLC, C-18 column, mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{45}H_{62}N_8O_5Pd+2\ CH_3COOH$
Molecular weight: 901.2+120.1
The product was analyzed by HPLC and MS identity confirmation.
Retention time: 12.9 min.
M.S(+): m/z=901
UV-Vis spectrum (MeOH): 746 nm, 516 nm, 384 nm, 332 nm

Example 33

Palladium $3^1$-oxo-15-methoxycarbonylmethyl-Rhodobacteriochlorin-$13^1$, $17^3$-di-(2-[(2-aminoethyl)amino]ethyl)amide (Compound 38)

20 mg of Pd-Bpheid, 3 (28 μmol) and 2 ml (18.3 mmol) of Diethylenetriamine were stirred at room temperature for 90 minutes under argon atmosphere. After this time, a solution of 130 mg of PyBroP (279 μmol) in 700 μl of chloroform was introduced to the reaction vessel. The mixture was stirred for another 90 min. at room temperature under argon atmosphere. Then the reaction was cooled, and excess of coupling reagent was destroyed by adding 1 ml of water. The reaction mixture was neutralized by glacial acetic acid and diluted with water. The product was purified by preparative HPLC, C-18 column, mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{43}H_{60}N_{10}O_5Pd+4\ CH_3COOH$
Molecular weight: 904.1+240.2
The product was analyzed by HPLC and MS identity confirmation.
Retention time: 1.95 min. (aggregate)
M.S(+): m/z=904
UV-Vis spectrum (MeOH): 745 nm, 514 nm, 382 nm, 330 nm

Example 34

Palladium $3^1$-oxo-15-methoxycarbonylmethyl-Rhodobacteriochlorin-$13^1$,$17^3$-di-(2-[(2-$N^2$-diethylaminoethyl)amino]ethyl) amide (Compound 39)

20 mg of Pd-Bpheid, 3 (28 μmol) and 1 ml (5.33 mmol) of N,N-diethyl-diethylenetriamine, were stirred at room temperature for 4 hours under argon atmosphere. After this time, a solution of 130 mg of PyBroP (279 μmol) in 500 μl of chloroform was introduced to the reaction vessel. The mixture was stirred for another 2.5 hours at room temperature under argon atmosphere. Then the reaction was cooled, and excess of coupling reagent was destroyed by adding 1 ml of water. The reaction mixture was neutralized by glacial acetic acid and diluted in water. The product was purified by preparative HPLC, C-18 column, mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{51}H_{76}N_{10}O_5Pd+4\ CH_3COOH$
Molecular weight: 1015.5+240.2
The product was analyzed by HPLC and MS identity confirmation.
Retention time: 5.3-6.6 min.
M.S(+): m/z=1015
UV-Vis spectrum (MeOH): 743 nm, 512 nm, 380 nm, 329 nm

Example 35

Palladium $3^1$-oxo-15-methoxycarbonylmethyl-Rhodobacteriochlorin-$13^1$, $17^3$-di(2-morpholino-N-ethyl)amide (Compound 40)

20 mg of Pd-Bpheid, 3 (28 μmol) and 2 ml (15.2 mmol) of N-(2-aminoethyl)morpholine, were stirred at room temperature for 2 hours under argon atmosphere. After this time, a solution of 136 mg of PyBroP (291 μmol) in 700 μl of chloroform was introduced to the reaction vessel. The mixture was stirred for another 2 hours at room temperature under argon atmosphere. Then the reaction was cooled, and excess of coupling reagent was destroyed by adding 1 ml of water. The reaction mixture was neutralized by glacial acetic acid and diluted in water. The mixture was dissolved in water and washed with chloroform, 3×100 ml. The organic solvent was evaporated and the product was purified by preparative HPLC, C-18 column, mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{47}H_{62}N_8O_7Pd+2\ CH_3COOH$
Molecular weight: 958.4+120.1
The product was analyzed by HPLC and MS identity confirmation.
Retention time: 11.6 min.
M.S(+): m/z=958
UV-Vis spectrum (MeOH): 745 nm, 513 nm, 381 nm, 330 nm.

Example 36

Palladium $3^1$-oxo-15-methoxycarbonylmethyl-Rhodobacteriochlorin-$13^1$, $17^3$-di(2-piperazino-N-ethyl)amide (Compound 41)

20 mg of Pd-Bpheid, 3 (28 μmol) and 1 ml (7.4 mmol) of N-(2-aminoethyl)piperazine (97%), were stirred at room temperature for 22 hours under argon atmosphere. After this time, a solution of 130 mg of PyBroP (279 μmol) in 500 μl of chloroform was introduced to the reaction vessel. The mixture was stirred for another 3.5 hours at room temperature under argon atmosphere. Then the reaction was cooled, and excess of coupling reagent was destroyed by adding 1 ml of water. The reaction mixture was neutralized by glacial acetic acid and diluted in water. The product was purified by preparative HPLC, C-18 column, mobile phase: A=0.2% acetic acid in water. B=0.2% acetic acid in acetonitrile. Gradient: 40% B (0-6 min) to 95% B (30-33 min). Flow rate: 4 ml/min.

Formula structure: $C_{47}H_{64}N_{10}O_5Pd+4\ CH_3COOH$
Molecular weight: 955.5+240.2
The product was analyzed by HPLC and MS identity confirmation.
Retention time: 11.4 min.
M.S(+): m/z=955
UV-Vis spectrum (MeOH): 744 nm, 513 nm, 380 nm, 329 nm.

Example 37

Palladium $3^1$-oxo-15-methoxycarbonylmethyl-Rhodobacteriochlorin-$13^1$, $17^3$-di-(3-[(3-aminopropyl)amino]propyl)amide (Compound 42)

Active ester preparation—Typically, 25 mg of Pd-Bpheid, 3 (35 μmol) and 39.4 mg of N-hydroxysuccinimide (HOSu or NHS) (342 µmol) were dissolved in 1 ml of dry DMF under argon. 31 mg of 1,3-dicyclohexylcarbodiimide (DCC) (150 µmol) were added in 500 µl of dry DMF. The reaction was stirred at room temperature overnight. The DMF was then evaporated and the product was purified by $SiO_2$ liquid chromatography with 95% $CHCl_3$:5% EtOH as the eluent. The solvent was then evaporated to yield 55 mg of activated ester. Experiments show that it is not necessary to isolate and purify the active ester.

20 mg of Pd-Bpheid-OSu (24.7 µmol) were stirred at room temperature with 1 ml of freshly distilled bis(3-aminopropyl) amine for 3 hours under argon atmosphere. The reaction mixture was then vacuum evaporated at room temperature. After evaporation, 1 ml of water was added to the residue and the product was purified by preparative HPLC on a C-18, Mobile phase: A=0.1% acetic acid, pH=7.2, in water. B=0.1% acetic acid, pH=7.2, in acetonitrile. Gradient: 20% B (0-2 min) to 90% B (20-22 min). Flow rate: 4 ml/min.

Formula structure: $C_{47}H_{68}N_{10}O_5Pd$+4 $CH_3COOH$
Molecular weight: 959.4+240.2
The product was analyzed by HPLC and MS identity confirmation.
Retention time: 12.83 min.
M.S(+): m/z=959
UV-Vis spectrum: 750 nm, 516 nm, 386 nm 330 nm 268 nm

Example 38

Palladium $3^1$-oxo-15-methoxycarbonylmethyl-Rhodobacteriochlorin-$13^1$,$17^3$-di([2-bis(2-aminoethyl)amino]ethyl)amide (Compound 43)

20 mg of Pd-Bpheid-OSu (24.7 µmol) prepared in Example 38 above, were stirred in room temperature with 1 ml of tris(2-aminoethyl)amine for 3 hours under argon atmosphere. The reaction mixture was then vacuum evaporated at room temperature. Then, 1 ml of water was added to the residue and the product was purified on preparative HPLC with C-18 silica column, Mobile phase: A=0.1% acetic acid, pH=7.2, in water. B=0.1% acetic acid, pH=7.2, in acetonitrile. Gradient: 20% B (0-2 min) to 90% B (20-22 min). Flow rate: 4 ml/min.

Formula structure: $C_{47}H_{70}N_{12}O_5Pd$+6 $CH_3COOH$
Molecular weight: 989.4+360.3
The product was analyzed by HPLC and MS identity confirmation.
Retention time: 114.15 min.
M.S(+): m/z=989
UV-Vis spectrum: 750 nm, 516 nm, 386 nm 332 nm

Example 39

Palladium $3^1$-oxo-15-methoxycarbonylmethyl-Rhodobacteriochlorin-$13^1$,$17^3$-di(2-N-(2'-pyridyl)aminoethyl)amide (Compound 44)

1) 500 mg of 2-chloropyridine (4.40 mmol) were dissolved in 3.0 ml of ethylenediamine (44.0 mmol) and the mixture was refluxed for 6 hours at 100° C. At the end, the excess of ethylenediamine was evaporated in vacuum at room temperature. The product N-(2-pyridyl)ethylenediamine) was purified on silica gel 60 (0.040-0.063 mm). Mobil phase: methanol 90%, ammonia solution 10%.

TLC analysis on sheet Silica gel 60 $F_{254}$ Mobil phase: methanol 90%, ammonia solution 10%. Product Rf=0.43.

2) 30 mg of Pd-Bpheid-OSu (0.037 mmol, prepared in Example 38) were added to a solution of 110 mg of N-(2-pyridyl)ethylenediamine (0.80 mmol) in dry dimethylformamide. The solution was stirred during 5 hours at room temperature under argon atmosphere.

The product was purified by preparative HPLC, using a C-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{49}H_{56}N_{10}O_5Pd$+4 $CH_3COOH$
Molecular weight: 971.5+240.2
The product was analyzed by HPLC and MS identity confirmation.
Retention time: 13.96 min.
M.S(+): m/z=971
UV-Vis spectrum: 750 nm, 516 nm, 386 nm 332 nm

Example 40

Palladium $3^1$-oxo-15-methoxycarbonylmethyl-Rhodobacteriochlorin-$13^1$, $17^3$-di(2-$N^2$-diethylaminoethyl)amide (Compound 45)

1) 30 mg of Pd-Bpheid, 3 (42 µmole) were stirred in 300 µl of 2-(diethylamino)ethylamine (2.11 mmol) at room temperature for 3 hours under argon atmosphere. The aminolysis product was analyzed by HPLC-MS.
Retention time: 15.49 min. M.S(+): m/z=831

2) A solution of 40 mg of PyBroP (0.086 mmol) in 200 µl of DMF was added to the previous reaction mixture. The solution was stirred at room temperature for 3 hours under argon atmosphere.

The product was purified by preparative HPLC, using a C-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{47}H_{66}N_8O_5Pd$+2 $CH_3COOH$
Molecular weight: 931.5+120.1
The product was analyzed by HPLC and MS identity confirmation.
Retention time: 12.81 min.
M.S(+): m/z=931
UV-Vis spectrum: 750 nm, 516 nm, 386 nm 332 nm

Example 41

Palladium $3^1$-oxo-15-methoxycarbonylmethyl-Rhodobacteriochlorin-$13^1$-(2,3-dihydroxypropyl)amide-$17^3$-(2-$N^3$-trimethyl ammoniumethyl)amide acetate salt (Compound 46)

1) Pd-Bpheid, 3 (100 mg, 0.140 mmol) was dissolved in 1.0 ml of N-methyl-2-pyrrolidone (NMP) and 3-amino-1,2-propanediol (405 mg, 4.45 mmol). The solution was stirred for 3 hours at room temperature under an argon atmosphere. The obtained product (Pd-Bpheid-aminopropanediol adduct) was purified on silica gel 60 (0.040-0.063 mm). Mobil phase: methanol 90%-ammonia solution 10%.

TLC analysis on sheet Silica gel 60 $F_{254}$ Mobil phase: methanol 80%, ammonia solution 20%. Product Rf=0.86.

The product was analyzed by HPLC-MS. Retention time: 18.42 min.
M.S(+): m/z=805

2) The Pd-Bpheid-aminopropanediol adduct (37 mg, 0.052 mmol) was dissolved in 1.5 ml of NMP. A coupling reagent benzotriazole-N,N,N',N'-tetramethyluronium hexafluorophosphate (HBTU) (200 mg, 0.52 mmol), triethylamine (110 µl, 0.78 mmol) and (2-aminoethyl)trimethylammonium chloride hydrochloride (46 mg, 0.26 mmol) were added. The solution was stirred for 2 hours at room temperature under argon atmosphere. The product was purified by HPLC, using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{43}H_{61}N_7O_7Pd+CH_3COO^-$
Molecular weight: 892.4+59.0

The product was analyzed by HPLC and MS identity confirmation.

Retention time: 13.34 min.
M.S(+): m/z=892

Example 42

Palladium $3^1$-oxo-15-methoxycarbonylmethyl-Rhodobacteriochlorin-$13^1$-(2,3-dihydroxypropyl)amide-$17^3$-(2-aminoethyl) amide (Compound 47)

1) Aminolysis of Pd-Bpheid with 3-amino-1,2-propanediol and subsequent purification were performed as described in Example 42 for compound 46.

2) 37 mg of the Pd-Bpheid-aminopropanediol adduct (0.052 mmol) were dissolved in 300 μl of NMP. 22 mg of PyBroP (0.046 mmol), 10 μl of ethylenediamine (0.155 mmol) were added. The solution was stirred for 1 hour at room temperature under argon atmosphere. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{40}H_{53}N_7O_7Pd+CH_3COOH$
Molecular weight: 848.3+60.0

The product was analyzed by HPLC and MS identity confirmation.

Retention time: 13.15 min.
M.S(+): m/z=848

Example 43

Palladium $3^1$-oxo-15-methoxycarbonylmethyl-Rhodobacteriochlorin-$13^1$-(2-aminoethyl)amide-$17^3$-(2,3-dihydroxypropyl) amide (Compound 48)

1) 30 mg of Pd-Bpheid, 3 (42 μmol) were stirred in 1 ml (15 mmol) of ethylenediamine, during 30 minutes at room temperature under argon atmosphere. At the end, the excess of ethylenediamine was evaporated in vacuum at room temperature, and then the solution was frozen in liquid nitrogen and lyophilized in order to eliminate traces of ethylenediamine.

2) The aminolysis product was reacted with 80 mg (0.17 mmol) of PyBroP dissolved in 100 μl of chloroform and 80 mg (0.88 mmol) of 3-amino-1,2-propanediol dissolved in 2 ml of NMP at room temperature, under argon atmosphere during 16 hours. The product was purified by HPLC, using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{40}H_{53}N_7O_7Pd+CH_3COOH$
Molecular weight: 848.3+60.0

The product was analyzed by HPLC and MS identity confirmation.

Retention time: 8.43 min.
M.S(+): m/z=848

Example 44

Palladium $3^1$-oxo-15-methoxycarbonylmethyl-Rhodobacteriochlorin-$13^1$-(2,3-dihydroxypropyl)amide-$17^3$-(2-$N^2$-dimethyl aminoethyl)amide (Compound 49)

1) Aminolysis of Pd-Bpheid with 3-amino-1,2-propanediol and subsequent purification were performed as described for compound 46 in Example 42.

2) The Pd-Bpheid aminopropanediol adduct (25 mg, 0.031 mmol) was dissolved in 300 μl of NMP. HBTU (120 mg, 0.32 mmol), N,N-dimethylethylenediamine (14 mg, 0.16 mmol) and potassium carbonate (88 mg) were added. Buffer solution was added to pH=7. The solution was stirred for 20 hour at room temperature under argon atmosphere. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{42}H_{57}N_7O_7Pd+CH_3COOH$
Molecular weight: 876.3+60.0

The product was analyzed by HPLC and MS identity confirmation.

Retention time: 14.74 min.
M.S(+): m/z=876

Example 45

Palladium $3^1$-oxo-15-methoxycarbonylmethyl-Rhodobacteriochlorin-$13^1$-(2-$N^2$-dimethylaminoethyl)amide-$17^3$-(2,3-dihydroxypropyl)amide (Compound 50)

1) Aminolysis of Pd-Bpheid with N,N-dimethyl ethylenediamine and subsequent purification were performed as described for compound 25 in Example 20.

2) The aminolysis product was reacted with 80 mg (0.17 mmol) of PyBroP dissolved in 100 μl of chloroform and 80 mg (0.88 mmol) of 3-amino-1,2-propanediol dissolved in 2 ml of NMP at room temperature under argon atmosphere during 16 hours. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 μl/min.

Formula structure: $C_{42}H_{57}N_7O_7Pd+CH_3COOH$
Molecular weight: 876.3+60.0

The product was analyzed by HPLC and MS identity confirmation.

Retention time: 12.31 min.
M.S(+): m/z=876

Example 46

Palladium $3^1$-oxo-15-methoxycarbonylmethyl-Rhodobacteriochlorin-$13^1$-(2,3-dihydroxypropyl)amide-$17^3$-(2-[(2-aminoethyl)amino]ethyl)amide (Compound 51)

1) Aminolysis of Pd-Bpheid with 3-amino-1,2-propanediol and subsequent purification were performed as described for 46 in Example 42.

2) 12 mg of the Pd-Bpheid aminopropanediol adduct (0.015 mmol) were dissolved in 400 μl of DMF. 34 mg of HBTU (0.64 mmol), 21 μl of triethylamine (0.15 mmol) and 16 μl of diethylenetriamine (0.15 mmol) were added. The solution was stirred for 5 hour at room temperature under argon atmosphere. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{42}H_{58}N_8O_7Pd+2CH_3COOH$
Molecular weight: 891.4+120.1
The product was analyzed by HPLC and MS identity confirmation.
Retention time: 12.42 min.
M.S(+): m/z=891

Example 47

Palladium $3^1$-oxo-15-methoxycarbonylmethyl-Rhodobacteriochlorin-$13^1$-(2,3-dihydroxypropyl)amide-$17^3$-(2-[(2-$N^2$-diethyl aminoethyl)amino]ethyl)amide (Compound 52)

1) Aminolysis of Pd-Bpheid with 3-amino-1,2-propanediol and subsequent purification were performed as described for 46 in Example 42.

2) 20 mg of the Pd-Bpheid aminopropanediol adduct (0.025 mmol) were dissolved in 1.0 ml of NMP. 94 mg of HBTU (0.25 mmol), 52 µl of triethylamine (0.375 mmol) and 23 µl of N,N-diethyldiethylenetriamine (0.125 mmol) were added. The solution was stirred for 3 hour at room temperature under argon atmosphere. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{46}H_{66}N_8O_7Pd+2CH_3COOH$
Molecular weight: 947.5+120.1
The product was analyzed by HPLC and MS identity confirmation.
Retention time: 11.70 min.
M.S(+): m/z=947

Example 48

Palladium $3^1$-oxo-15-methoxycarbonylmethyl-Rhodobacteriochlorin-$13^1$-(2,3-dihydroxypropyl)amide-$17^3$-(2-morpholino-N-ethyl)amide (Compound 53)

1) Aminolysis of Pd-Bpheid with 3-amino-1,2-propanediol and subsequent purification was performed as described for 46 in Example 42.

2) 50 mg of the Pd-Bpheid aminopropanediol adduct (0.07 mmol) were dissolved in 800 µl of dry DMF. 80 mg of HOSu (0.70 mmol) and 216 mg of DCC (1.04 mmol) were added. The solution was stirred for 90 minutes at room temperature under argon atmosphere. The product was purified by injection to HPLC, using a RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

3) 7.0 mg of the Pd-Bpheid-aminopropanediol-OSu-activated compound (7.77×10⁻³ mmol) were dissolved in 200 µl of dry DMF. 25 µl of dry N-methyl-morpholine (0.23 mmol) and 30 µl N-(2-aminoethyl)morpholine (0.23 mmol) were added. The solution was stirred for 75 minutes at room temperature under argon atmosphere. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min Formula structure: $C_{44}H_{59}N_7O_8Pd+CH_3COOH$
Molecular weight: 918.4+60.0

The product was analyzed by HPLC and MS identity confirmation.
Retention time: 13.05 min.
M.S(+): m/z=918

Example 49

Palladium $3^1$-oxo-15-methoxycarbonylmethyl-Rhodobacteriochlorin-$13^1$-(2,3-dihydroxypropyl)amide-$17^3$-(2-piperazino-N-ethyl)amide (Compound 54)

1) Aminolysis of Pd-Bpheid with 3-amino-1,2-propanediol and subsequent purification was performed as described for 46 in Example 42.

2) 23 mg of the Pd-Bpheid aminopropanediol adduct (0.032 mmol) were dissolved in 200 µl of dry DMF. 5.55 mg of HOSu (0.048 mmol) and 10.85 mg of DCC (0.048 mmol) were added. The solution was stirred for 22 hours at room temperature under argon atmosphere.

3) To the reaction vessel of (2), 4 µl of 1-(2-aminoethyl)piperazine (0.03 mmol) and 12 µl of triethylamine (0.09 mmol) were added. The solution was stirred for 4 hours at room temperature under argon atmosphere. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min Formula structure: $C_{44}H_{60}N_8O_7Pd+2CH_3COOH$ Molecular weight: 917.4+120.1

The product was analyzed by HPLC and MS identity confirmation.

Retention time: 13.03 min.

M.S(+): m/z=917.

Example 50

Palladium $3^1$-oxo-15-methoxycarbonylmethyl-Rhodobacteriochlorin-$13^1$-(2-[(2-aminoethyl)amino]ethyl)amide-$17^3$-(2,3-dihydroxypropyl)amide (Compound 5)

1) Aminolysis of Pd-Bpheid with diethylenetriamine was performed as described for compound 27 in Example 22. The product was purified on a silica column with a running solution of 80% methanol and 20% ammonia.

2) The Pd-Bpheid aminolysis product was reacted with 80 mg (0.17 mmol) of PyBroP dissolved in 100 µl of chloroform and 80 mg (0.88 mmol) of 3-amino-1,2-propanediol dissolved in 2 ml of NMP at room temperature, under argon atmosphere during 16 hours. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{42}H_{59}N_8O_7Pd+2CH_3COOH$

Molecular weight: 890+120.1

The product was analyzed by HPLC and MS identity confirmation.

Retention time: 11.90 min.

M.S(+): m/z=890

Example 51

Palladium $3^1$-oxo-15-methoxycarbonylmethyl-Rhodobacteriochlorin-$13^1$-(2,3-dihydroxypropyl)amide-$17^3$-(2-N-(2'-pyridyl)aminoethyl)amide (Compound 56)

1) Aminolysis of Pd-Bpheid with 3-amino-1,2-propanediol and subsequent purification was performed as described for 46 in Example 42.

2) 19 mg of the Pd-Bpheid aminolysis product (0.024 mmol) were dissolved in 1.0 ml of dry NMP. 97 mg of N-(2-pyridyl)ethylenediamine (0.142 mmol), prepared as described in Example 40, 77 mg of the coupling reagent O-(benzotriazol-1-yl)-N,N,N',N'-tetramethyluronium tetrafluoroborate (TBTU) (0.24 mmol) and 50 µl of triethylamine (0.36 mmol) were added. The solution was stirred for 90 minutes at room temperature under argon atmosphere. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min Formula structure: $C_{45}H_{56}N_8O_7Pd+2CH_3COOH$
Molecular weight: 925.4+120.1
The product was analyzed by HPLC and MS identity confirmation.
Retention time: 14.38 min.
M.S(+): m/z=925

Example 52

Palladium $3^1$-oxo-15-methoxycarbonylmethyl-Rhodobacteriochlorin-$13^1$-(2-N-(2'-pyridyl)aminoethyl)amide-$17^3$-(2,3-dihydroxypropyl)amide (Compound 57)

1) N-(2-pyridyl)ethylenediamine prepared as described in Example 40 above (200 mg), was mixed with 40 mg of Pd-Bpheid overnight at room temperature under argon atmosphere. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

2) The Pd-Bpheid-2-(diaminoethyl)-pyridine aminolysis product (35 mg, 0.042 mmol) was dissolved in 200 µl of dry DMF. 10 mg of HOSu (0.086 mmol) and 22 mg of DCC (0.105 mmol) were added. The solution was stirred for 5 hours at room temperature under argon atmosphere.

The product was analyzed by HPLC and MS identity confirmation. Retention time: 18.91 min.
M.S(+): m/z=949

2) 28 mg of the Pd-Bpheid-2-(diaminoethyl)-pyridine-OSu-activated ester (0.03 mmol) were dissolved in 300 µl of dry dimethylformamide. 28 mg of 3-amino-1,2-propanediol (0.31 mmol) and 41 µl of triethylamine were added. The solution was stirred for 14 hours at room temperature under argon atmosphere. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{45}H_{56}N_8O_7Pd+2CH_3COOH$
Molecular weight: 925.4+120.1
The product was analyzed by HPLC and MS identity confirmation.
Retention time: 14.53 min.
M.S(+): m/z=925

Example 53

Palladium $3^1$-oxo-15-methoxycarbonylmethyl-Rhodobacteriochlorin-$13^1$-(2,3-dihydroxypropyl)amide-$17^3$-([2-bis(2-aminoethyl)amino]ethyl)amide (Compound 58)

1) Aminolysis of Pd-Bpheid with 3-amino-1,2-propanediol and subsequent purification was performed as described for 46 in Example 42.

2) All solvents were vacuum degassed. The purified amino diol was dissolved in 2 ml of NMP and 200 µl of DMSO. To the solution, 100 mg (0.21 mmol) of PyBroP in 200 µl of chloroform, and 160 µl (1 mmol) of liquid tris(2-ethylamino)amine were added. The compounds were stirred under argon at room temperature during 16 hrs. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{44}H_{63}N_9O_7Pd+3CH_3COOH$
Molecular weight: 933.2+180.2
The product was analyzed by HPLC and MS identity confirmation.
Retention time: 10.86 min.
M.S(+): m/z=933.

Example 54

Palladium $3^1$-oxo-15-methoxycarbonylmethyl-Rhodobacteriochlorin-$13^1$-([2-bis(2-aminoethyl)amine]ethyl)amide-$17^3$-(2,3-dihydroxypropyl)amide (Compound 59)

1) 25 mg of Pd-Bpheid, 3 (35 µmol) and 39.4 mg of HOSu (342 µmol) were dissolved in 1 ml of dry DMF under argon atmosphere. 31 mg of DCC (150 µmol) dissolved in 500 µl of dry DMF were introduced. The reaction was stirred at room temperature overnight. DMF was evaporated and the product was purified by liquid chromatography using $SiO_2$ as a stationary phase and 95% $CHCl_3$:5% EtOH as eluent. The product was received in the first four fractions. The solvent was evaporated; 55 mg of Pd-Bpheid-OSu were received.

2) 25 mg of the previous product, Pd-Bpheid-OSu, (30 µmol), were dissolved in 1 ml of dry DMF. To this solution 13 µl of N,N-diisopropylethylamine (DIPEA) (74 µmol) were added. The reaction mixture was stirred under argon atmosphere for a couple of minutes. 3-amino-1,2-propanediol (97 µl, 37 µmol) in 1 ml DMF were added to the reaction vessel. The reaction was stirred at room temperature under inert atmosphere for 5 hours. No aminolysis product was detected.

3) 200 ml (1.28 mmol) of tris(aminoethyl)amine were added to the reaction vessel of (2). Argon was passed through the reaction vessel. The mixture was stirred overnight at room temperature. The product was purified by diluting the reaction mixture with 30 ml of water and washing the aqueous layer with 30 ml of n-butanol. The organic layer was then washed with 3×30 ml of water. The butanol was evaporated and the product was dissolved in 1.5 ml of acidic water and 300 µl of acetonitrile. The solution was divided into aliquots and lyophilized.

Formula structure: $C_{44}H_{63}N_9O_7Pd\ 3CH_3COOH$
Molecular weight: 933.2+180.2
The product was analyzed by HPLC and MS identity confirmation.
Retention time: 12.46 min.
M.S(+): m/z=934

Example 55

Palladium $3^1$-oxo-15-methoxycarbonylmethyl-Rhodobacteriochlorin-$13^1$-(3-aminopropyl)amide-$17^3$-(2,3-dihydroxypropyl)amide (Compound 60)

1) 30 mg of Pd-Bpheid, 3 (42 μmol) were stirred in 1 ml (11.8 mmol) of 1,3-diaminopropane, during 60 minutes at room temperature under argon atmosphere. Then the excess of amine was evaporated in high vacuum during 16 hrs.

2) The product was dissolved in 1 ml of DMSO and 1 ml of DMF, and stirred with a solution of 100 mg (0.21 mmol) of PyBroP in 500 μl of chloroform and 100 mg of 3-amino-1,2-propanediol at room temperature under argon atmosphere, during 16 hrs. Purification of the product was made by precipitation with water followed by HPLC purification using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{41}H_{55}N_7O_7Pd+CH_3COOH$
Molecular weight: 861.2+60.0
The product was analyzed by HPLC and MS identity confirmation.
Retention time: 13.06 min.
M.S(+): m/z=861

Example 56

Palladium $3^1$-oxo-15-methoxycarbonylmethyl-Rhodobacteriochlorin-$13^1$-(4-aminobutyl)amide-$17^3$-(2,3-dihydroxypropyl) amide (Compound 61)

1) 20 mg of Pd-Bpheid, 3 (28 μmol) and 0.5 ml (4.9 mmol) of 1,4-diaminobutane (99%), were stirred at 30° C. for 4 hours under argon atmosphere at which time 1 ml of water was added to the reaction vessel and stirred for a couple of minutes. The solution was then lyophilized.

2) The Pd-Bpheid aminolysis product was dissolved in 2 ml of dry DMF. A solution of 414 mg (4.4 mmol) of 3-amino-1,2-propanediol (97%) in 400 μl of dry DMF was added to the mixture. The reaction vessel was flushed with argon. 130 mg of PyBroP (279 μmol) in 500 μl of chloroform were introduced to the reaction vessel. The mixture was stirred for another 90 min at 30° C. under argon atmosphere. Then the reaction was cooled, and excess of coupling reagent was destroyed by adding 1 ml of water. The mixture was diluted with 100 ml of water. The product was extracted four times with chloroform, 100 ml and 3×50 ml. The organic washings were combined and evaporated. The product was purified by HPLC using an RP-18 column. Mobile phase: A=0.2% acetic acid in water. B=A=0.2% acetic acid in acetonitrile. Gradient: 20% B (0-6 min) to 95% B (30-33 min). Flow rate: 4 ml/min.

Formula structure: $C_{42}H_{57}N_7O_7Pd+CH_3COOH$
Molecular weight: 876.4+60.0
The product was analyzed by HPLC and MS identity confirmation.
Retention time: 13.32 min.
M.S(+): m/z=876

Example 57

Palladium $3^1$-oxo-15-methoxycarbonylmethyl-Rhodobacteriochlorin-$13^1$-(2-$N^2$-diethylaminoethyl)amide-$17^3$-(2,3-dihydroxy propyl)amide (Compound 62)

1) 30 mg of Pd-Bpheid, 3 (0.042 mmol) were dissolved in 300 μl of 2-(diethylaminoethyl)amine (2.11 mmol). The solution was stirred for 3 hours at room temperature under argon atmosphere. The excess of 2-(diethylaminoethyl)amine was evaporated in high vacuum.

The product was analyzed by HPLC-MS. Retention time: 15.49 min.
M.S(+): m/z=831

2) 27 mg of 3-amino-1,2-propanediol (0.3 mmol), 28 mg of PyBroP (0.06 mmol) and 300 μl of DMF were added to the solution in section 1. The solution was stirred for 2 hours at room temperature under argon atmosphere. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{44}H_{61}N_7O_7Pd+CH_3COOH$
Molecular weight: 906.4+60.0
The product was analyzed by HPLC and MS identity confirmation.
Retention time: 13.93 min.
M.S(+): m/z=904

Example 58

Palladium $3^1$-oxo-15-methoxycarbonylmethyl-Rhodobacteriochlorin-$13^1$-(2-N-ethylaminoethyl)amide-$17^3$-(2,3-dihydroxy propyl)amide (Compound 63)

1) 30 mg of Pd-Bpheid, 3 (42 μmol) were stirred in 1 ml (9.5 mmol) of N-ethylethylenediamine for 60 minutes at room temperature under argon atmosphere. Then the excess of amine was evaporated in high vacuum.

2) The product was then dissolved in 800 μl of DMF and stirred with a solution of 70 mg (0.77 mmol) of 3-amino-1,2-propanediol in 200 μl of DMF and a solution of 70 mg (0.15 mmol) of PyBroP in 200 μl of chloroform, at room temperature under argon atmosphere for 2 hrs. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{42}H_{57}N_7O_7Pd+CH_3COOH$
Molecular weight: 875.2+60.0
The product was analyzed by HPLC and MS identity confirmation.
Retention time: 13.16 min.
M.S(+): m/z 875

Example 59

Palladium $3^1$-oxo-15-methoxycarbonylmethyl-Rhodobacteriochlorin-$13^1$-(3-N-methylaminopropyl)amide-$17^3$-(2,3-dihydroxypropyl)amide (Compound 64)

1) 30 mg of Pd-Bpheid, 3 (42 μmol) were stirred in 1 ml (9.6 mmol) of N-methyl-1,3-propanediamine, for 120 minutes at room temperature under argon atmosphere. Then the excess of amine was evaporated in high vacuum.

2) The product was then dissolved in 800 μl of DMF and stirred with a solution of 80 mg (0.88 mmol) of 3-amino-1,2-propanediol in 200 μl of DMF and a solution of 75 mg (0.16 mmol) of PyBroP in 200 μl of chloroform, at room temperature under argon atmosphere during 2 hrs. The product was purified by HPLC using an RP-18 column. Mobile phase:

A=0.2% acetic acid in water. B=0.2% acetic acid in acetonitrile. Gradient: 20% B (0-6 min) to 95% B (30-33 min). Flow rate: 4 ml/min.

Formula structure: $C_{42}H_{57}N_7O_7Pd+CH_3COOH$
Molecular weight: 875.2+60.0
The product was analyzed by HPLC and MS identity confirmation.
Retention time: 12.93 min.
M.S(+): m/z 875

Example 60

Palladium $3^1$-oxo-15-methoxycarbonylmethyl-Rhodobacteriochlorin-$13^1$-(2-N-dimethylaminoethyl)amide-$17^3$-(2-hydroxy ethyl)amide (Compound 65)

1) 300 mg of Pd-Bpheid, 3 (420 μmol), 655 mg of PyBroP (1260 μmol), 30.781 of ethanolamine (504 μl), 0.6 ml of DMF and 0.1 ml of triethylamine were stirred in room temperature for 1 hr under argon atmosphere. The reaction mixture was evaporated in vacuum, the product was purified by water chloroform extraction. The chloroform phase containing the product was dried over anhydrous $MgSO_4$, filtered and evaporated.

2) After evaporation, 460 μl of N,N-dimethylethylenediamine (4.2 mmol) were added and the reaction mixture was stirred at room temperature for 1 hr under argon atmosphere. The product was purified by water and n-butanol extraction. The n-butanol phase containing the product was dried ($MgSO_4$ anhydrous), filtered and evaporated.

Formula structure: $C_{41}H_{55}N_7O_6Pd+CH_3COOH$
Molecular weight: 848.2+60.0
The product was analyzed by HPLC and MS identity confirmation.
M.S(+): m/z (most abundant)=846
UV-Vis spectrum: 750 nm, 516 nm, 386 nm, 332 nm, 264 nm Example 61

Palladium $3^1$-oxo-15-methoxycarbonylmethyl-Rhodobacteriochlorin-$13^1$-(2-$N^2$-dimethylaminoethyl)amide-$17^3$-(3-hydroxy propyl)amide (Compound 66)

1) Aminolysis of Pd-Bpheid was performed as described for compound 25 in Example 20.

2) The entire product obtained in step 1 above was then dissolved in 6 ml of DMF. 1 ml of the solution was reacted with 20 μl (0.26 mmol) of 3-amino-1-propanol, 70 mg (0.15 mmol) of PyBroP and 20 μl (0.18 mmol) of N-methyl-morpholine. The mixture was stirred for 90 minutes at room temperature under argon atmosphere. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{42}H_{57}N_7O_6Pd+CH_3COOH$
Molecular weight: 859.3+60.0
The product was analyzed by HPLC and MS identity confirmation.
Retention time: 15.38 min.
M.S(+): m/z=859

Example 62

Palladium $3^1$-oxo-15-methoxycarbonylmethyl-Rhodobacteriochlorin-$13^1$-(2-$N^2$-dimethylaminoethyl)amide-$17^3$-(2-hydroxy propyl)amide (Compound 67)

1) Aminolysis of Pd-Bpheid was performed as described for compound 25 in Example 20.

2) The product was then dissolved in 6 ml of DMF. 1 ml of the solution was reacted with 20 μl (0.25 mmol) of 1-amino-2-propanol, 70 mg (0.15 mmol) of PyBroP and 20 μl (0.18 mmol) of N-methyl-morpholine. The mixture was stirred for 90 minutes at room temperature under argon atmosphere. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{42}H_{57}N_7O_6Pd+CH_3COOH$
Molecular weight: 859.3+60.0
The product was analyzed by HPLC and MS identity confirmation.
Retention time: 14.82 min.
M.S(+): m/z=859.

Example 63

Palladium $3^1$-oxo-15-methoxycarbonylmethyl-Rhodobacteriochlorin-$13^1$-(2-$N^2$-dimethylaminoethyl)amide-$17^3$-((R)-2-hydroxypropyl)amide (Compound 68)

The synthesis of compound 68 was identical to that of compound 67 described in Example 63 above, using the R optical isomer of the amino alcohol.

Formula structure: $C_{42}H_{57}N_7O_6Pd+CH_3COOH$
Molecular weight: 859.3+60.0
The product was analyzed by HPLC and MS identity confirmation.
Retention time: 15.52 min.
M.S(+): m/z=859.

Example 64

Palladium $3^1$-oxo-15-methoxycarbonylmethyl-Rhodobacteriochlorin-$13^1$-(2-$N^2$-dimethylaminoethyl)amide-$17^3$-((S)-2-hydroxypropyl)amide (Compound 69)

The synthesis of compound 68 was identical to that of compound 67 described in Example 63 above, using the S optical isomer of the amino alcohol.

Formula structure: $C_{42}H_{57}N_7O_6Pd+CH_3COOH$
Molecular weight: 859.3+60.0
The product was analyzed by HPLC and MS identity confirmation.
Retention time: 15.50 min.
M.S(+): m/z=859.

Example 65

Palladium $3^1$-oxo-15-methoxycarbonylmethyl-Rhodobacteriochlorin-$13^1$-(2-$N^2$-dimethylaminoethyl)amide-$17^3$-(2-(2-hydroxyethylamino)ethyl)amide (Compound 70)

1) Aminolysis of Pd-Bpheid was performed as described for compound 25 in Example 20.

2) The product was then dissolved in 6 ml of DMF. 1 ml of the solution was reacted with of N-(2-hydroxyethyl)-ethylenediamine (20 µl, 0.17 mmol), 70 mg (0.15 mmol) of PyBroP and 20 µl (0.18 mmol) of N-methyl-morpholine. The mixture was stirred for 90 minutes at room temperature under argon atmosphere. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 n/min.

Formula structure: $C_{43}H_{60}N_8O_6Pd+2CH_3COOH$

Molecular weight: 889.2+120.1

The product was analyzed by HPLC and MS identity confirmation.

Retention time: 13.34 min.

M.S(+): m/z=888.

Example 66

Palladium $3^1$-oxo-15-methoxycarbonylmethyl-Rhodobacteriochlorin-$13^1$-(3-N-(2'-pyridyl)aminopropyl)amide-$17^3$-(2,3-dihydroxypropyl)amide (Compound 71)

1) 500 mg of 2-chloropyridine (8.73 mmol) were dissolved in 3.6 ml of 1,3-diaminopropane (44 mmol). 100 mg of potassium carbonate and 200 µl of DMF were added. The compound was refluxed for 22 hours at 102° C. The product N-(2-pyridyl)propylenediamine was purified on silica gel 60 (0.040-0.063 mm). Mobil phase: methanol 90%, ammonia solution 10%. The product was non-colored oil. TLC analysis on sheet Silica gel 60 $F_{254}$ Mobil phase: methanol 90%, ammonia solution 10%. Product Rf=0.38.

2) 20 mg of Pd-Bpheid, 3 (28 µmol) were dissolved in 300 µl of NMP and 125 mg (0.83 mmol) of N-(2-pyridyl)propylenediamine were added. The solution was stirred for 23 hours at room temperature under argon atmosphere. The aminolysis product was purified on silica gel 60 (0.040-0.063 mm). Mobil phase: methanol 90%, ammonia solution 10%.

The product was analyzed by HPLC-MS. Retention time: 8.02 min.

M.S(+): m/z=864.

3) The Pd-Bpheid aminolysis product (30 mg; 0.023 mmol) was dissolved in 400 µl of NMP. 90 mg of HBTU (0.24 mmol), 50 µl of triethylamine (0.35 mmol) and 20 mg of 3-amino-1,2-propanediol (0.23 mmol) were added. The solution was stirred for 4 hours at room temperature under argon atmosphere. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{46}H_{58}N_8O_7Pd+2\ CH_3COOH$

Molecular weight: 941.4+120.1

The product was analyzed by HPLC and MS identity confirmation.

Retention time: 18.89 min.

M.S(+): m/z=941.

Example 67

Palladium $3^1$-oxo-15-methoxycarbonylmethyl-Rhodobacteriochlorin-$13^1$-(4-N-(2'-pyridyl)aminobutyl)amide-$17^3$-(2,3-dihydroxypropyl)amide (Compound 72)

1) 0.835 ml of 2-chloropyridine (8.8 mmol) were dissolved in 8.8 ml of 1,4-diaminobutane (88 mmol). The mixture was refluxed for 4 hours at 128° C. The product was purified on silica gel 60 (0.040-0.063 mm). Mobil phase: methanol 90%, ammonia solution 10%. The product was a colorless oil. TLC sheet Silica gel 60 $F_{254}$. Mobil phase: methanol 90%, ammonia solution 10%. Butyl diamine: Rf=0, Product Rf=0.42.

2) 30 mg of Pd-Bpheid, 3 (42 µmol) were dissolved in 700 µl of NMP and 80 mg (0.48 mmol) of N-(2-pyridyl)butylenediamine were added. The solution was stirred for 15 hours at room temperature under argon atmosphere. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

The product was analyzed by HPLC and MS identity confirmation

Retention time: 22.36 min.

M.S. (+): m/z=877.

3) 17 mg of the Pd-Bpheid aminolysis product (0.019 mmol) were dissolved in 400 µl of NMP and 100 µl of water. 9 mg of HOSu (0.077 mmol), 17 mg of N-(3-dimethylamino propyl)-N-ethylcarbodiimide (EDC) (0.87 mmol) and 5 µl of ammonia solution were added. After 16 hours, 200 mg of 3-amino-1,2-propanediol (2.2 mmol) were added. The solution was stirred for 2 hours at room temperature under argon atmosphere. The product was purified by preparative HPLC using an RP-18 column. Mobile phase: A=0.2% acetic acid in water. B=0.2% acetic acid in acetonitrile. Gradient: 20% B (0-6 min) to 95% B (30-33 nm). Flow rate: 4 ml/min.

Formula structure: $C_{47}H_{60}N_8O_7Pd+2CH_3COOH$

Molecular weight: 949.5+120.1

The product was analyzed by HPLC and MS identity confirmation.

Retention time: 15.79 min.

M.S(+): m/z=949

Example 68

Palladium $3^1$-oxo-15-methoxycarbonylmethyl-Rhodobacteriochlorin-$13^1$-(2,3-dihydroxypropyl)amide-$17^3$-(3-N-(2'-pyridyl)aminopropyl)amide (Compound 73)

1) Aminolysis with 3-amino-1,2-propanediol and subsequent purification was performed as described for compound 46 in Example 42.

2) 32 mg of the Pd-Bpheid aminolysis product (0.04 mmol) were dissolved in 800 µl of NMP. 152 mg of HBTU (0.4 mmol), 56 µl of triethylamine and 60 mg of N-(2-pyridyl)propylenediamine (prepared as described above for compound 72) were added. The solution was stirred for 16 hours at room temperature under argon atmosphere. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{46}H_{58}N_8O_7Pd+2\ CH_3COOH$

Molecular weight: 939.4+120.1

The product was analyzed by HPLC and MS identity confirmation.

Retention time: 15.28 min.

M.S(+): m/z=939

Example 69

Palladium $3^1$-oxo-15-methoxycarbonylmethyl-Rhodobacteriochlorin-$13^1$-(2,3-dihydroxypropyl)amide-$17^3$-(4-N-(2'-pyridyl)aminobutyl)amide (Compound 74)

1) Aminolysis with 3-amino-1,2-propanediol and subsequent purification was performed as described for compound 46 in Example 42.

2) 25 mg of the Pd-Bpheid aminolysis product (0.031 mmol) were dissolved in 600 µl of NMP. 120 mg of HBTU (0.31 mmol), 45 µl of triethylamine and 50 mg of N-(2-pyridyl)butylenediamine (prepared as described above for compound 72) were added. The solution was stirred for 20 hours at room temperature under argon atmosphere. The product was purified by HPLC using an RP-18 column. Mobile phase: A=0.2% acetic acid in water. B=0.2% acetic acid in acetonitrile. Gradient: 20% B (0-6 min) to 95% B (30-33 min). Flow rate: 4 ml/min.

Formula structure: $C_{47}H_{60}N_8O_7Pd + 2CH_3COOH$
Molecular weight: 953.5+120.1

The product was analyzed by HPLC and MS identity confirmation.
Retention time: 15.43 min.
M.S(+): m/z=953

Example 70

Palladium $3^1$-oxo-15-methoxycarbonylmethyl-Rhodobacteriochlorin-$13^1$-(2-$N^2$-dimethylaminoethyl)amide-$17^3$-(glycosyl) amide (Compound 75)

1) 300 mg of Pd-Bpheid, 3 (420 µmol) and 476 mg of HOSu (4.14 mmol) were dissolved in 4 ml of dry DMF under argon atmosphere. 435.5 mg of DCC (2.1 mmol) dissolved in 2 ml of dry DMF were introduced. The reaction was stirred at room temperature overnight. TLC (92% $CHCl_3$:8% MeOH) showed no un-reacted Pd-Bpheid.

2) 926 mg of glycosylamine hydrochloride, 98% (4.28 mmol) and 2190 µl of DIPEA (12.6 mmol) were introduced to the prior reaction vessel containing the active ester, Pd-Bpheid-OSu. The reaction was stirred under argon atmosphere at room temperature for 24 hours. TLC (8% $CHCl_3$: 92% MeOH) showed no un-reacted active ester remains in the reaction vessel.

3) 3 ml of N,N-dimethylethylenediamine (26 mmol) were added to the reaction vessel of step (2) and stirred over night at room temperature under argon. HPLC-MS showed that the desired product and its Schiff base are the main products. The reaction mixture was diluted with 100 ml of water and washed with 4×50 ml of n-butanol. It was necessary to add to each washing a small volume of aqueous saturated NaCl in order to achieve separation. The organic layers were combined and washed with 50 ml of water. The butanol was then evaporated and residual Schiff base was hydrolyzed using diluted acetic acid. The evaporated product was diluted in 60 ml of water containing 1% acetic acid. The acidic solution was stirred for 1 hour under argon atmosphere at room temperature. HPLC-MS showed the Schiff base was completely destroyed.

Formula structure: $C_{45}H_{61}N_7O_9Pd + CH_3COOH$
Molecular weight: 948.4+60.0

The product was analyzed by HPLC and MS identity confirmation.
Retention time: 13.81 min.
M.S(+): m/z=948

Example 71

Interactions of the Dicationic Compound 5 with Human Serum Albumin (HSA)

The photodynamic activity of the different Bchl derivatives critically depends on both the bioavailability of their monomeric (dimeric) forms and transcellular trafficking, which can be markedly modulated by binding to serum albumin.

A solution of 5 in PBS ($3.2 \times 10^{-4}$ M, 100 µl) was mixed with various amounts of human serum albumin (0.1, 0.5, 1, 2, and 5 mg). Aggregation, at high concentrations of 5 in aqueous solutions, is reflected by splitting of the original monomeric peak at 747 nm into two new peaks at 720 and 760 nm. The state of aggregation was followed spectrophotometrically over the range of albumin concentrations at room temperature in a 0.1 mm cuvette. The absorbance intensity values at the peak wavelengths were taken as an indication of the aggregation.

Figure 2:
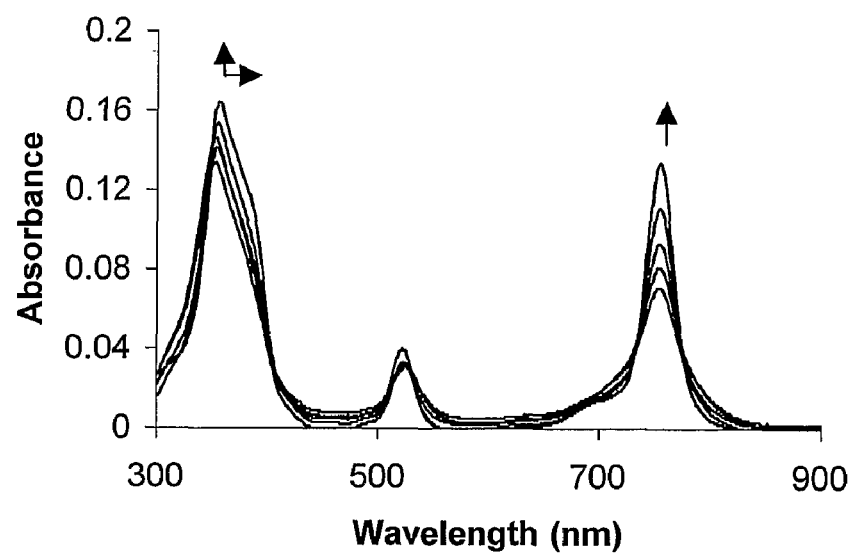
FIG. 2 depicts the absorption spectra of compound 5 in phosphate-buffered saline (PBS) with increasing concentrations of human serum albumin (HSA). ($\lambda_{ex}$=520 nm).

Addition of the albumin caused disaggregation of the sensitizer 5 in PBS (FIG. 2). The absorption spectra of the solutions containing increasing amounts of albumin resembled the spectrum of the monomeric pigment 5 in methanol.

II. Biological Section
Materials and Methods (i) Cell culture. H5V mouse endothelial cells were cultured as monolayers in Dulbecco's modified Eagle's medium (DMEM)/F12 containing 25 mM HEPES, pH 7.4, 10% fetal calf serum (FCS), glutamine (2 mM), penicillin (0.06 mg/ml), and streptomycin (0.1 mg/ml) (hereinafter referred to as the "culture medium"). The cells were grown at 37° C. in an 8% $CO_2$-humidified atmosphere.

(ii) Bacterial cultures. Bacteria of strains St. albus and *E. coli* XL-1 were cultured in liquid LB medium (*E. coli* in LB containing 12.5 µg tetracyclin/ml) to a final density of $OD_{600}$ nm=0.5-0.9 (1 OD=$8 \times 10^8$ bacteria/ml). The bacteria were spun down (4000×g, 5 min.) and resuspended in PBS.

(iii) Preparation of sensitizers for in vitro experiments. Stock solutions of the compounds 5, 7, 2 and 11 were prepared by dissolving the dry compounds directly in culture medium to the desired concentrations, prior to use.

(iv) Phototoxicity Assay.

(a) Cells. To determine the photodynamic efficacy, cells were cultured in 96-well plates ($40 \times 10^3$/well) and incubated in the dark in culture medium containing increasing concentrations of sensitizers 5, 7, 9 and 11, for a period of 1 min to 8 h. Unbound sensitizer was removed by washing the cells once with fresh culture medium. The plates were illuminated at room temperature, from their bottom side, for 10 min (650<λ<800 nm, 12 J/cm²). The light source was a 100 W Halogen lamp (Osram, Germany) equipped with a <650 nm cutoff and a 4-cm water filter. The cultures were placed in the culture incubator and cell survival was determined 24 h after illumination, by Neutral Red viability assay. Cell survival was calculated as the percent of the dye accumulated in the untreated controls. Triplicate determinations were conducted and representative experiments are shown. Three kinds of controls were used: (i) light control: cells illuminated in the absence of pigments; (ii) dark control: cells treated with pigments but kept in the dark; and (iii) untreated cells that were kept in the dark.

(b) Bacterial. To determine the photodynamic efficacy, bacteria were diluted to aliquots of 300 µl containing about $10^7$ bacteria, and incubated with increasing concentrations of sensitizer in plastic test tubes in the dark for 1 h at room temperature, and then illuminated at 70 mW/cm² for 15 min. Samples of the treated bacteria cultures were subsequently plated at different dilutions (50-200 bacteria/plate) on LB agar and cultured for 24 h at 37° C. for determination of bacterial survival by colony counting. Triplicate determinations were conducted and representative experiments are shown.

(v) Animals. Male CD1 nude mice (28-32 g) and male Wistar rats (250-300 g) were kept with free access to food and water in the departmental animal facility according to the guidelines of the Weizmann Institute of Science, Rehovot, Israel.

(vi) Anesthesia. Mice were anesthetized by i.p. injection of 80 µl ketamine (100 mg/ml, Rhone-Merieux, France) and xylazine (2%, Vitamed, Israel) mixture (85:15, v:v). Rats were anaesthetized by gas (2% of isofluorane in 98% $O_2$).

(vii) Tumor implantation. Cultured C6 glioma cell monolayers were scraped in saline, centrifuged at 250 g for 5 min, resuspended in saline and subcutaneously injected ($2 \times 10^6$ cells/mouse) into the back of CD1 nude mice. Tumors reached a treatment diameter of 6-8 mm within 2 weeks. The mice were sacrificed (according to the guidelines of the Weizmann Institute of Science) when tumors reached the diameter of $\geq 15$ mm.

(viii) Preparation of sensitizers for injection. Stock solutions of compounds 5 and 11 were prepared prior to use by dissolving the dry compounds directly in PBS to the desired concentration for injection.

(ix) Pharmacokinetics. Anesthetized Wistar rats (n=3 per each time-point) were i.v. injected with compound 5 of the invention (0.6 mg/kg). Blood samples (~100-200 µl) were drawn at 0, 5, 10, 15, 20, 30, 45, 60, 120, 360 and 480 min after injection, transferred into and weighed in pre-weighted 2 ml test tubes containing 10 µl of heparin, and mixed carefully. Control blood samples were collected from three untreated rats and treated accordingly. The test tubes containing the blood samples were weighed again in order to calculate the exact sample mass. The blood samples were then frozen in liquid nitrogen and lyophilized. The lyophilized samples were extracted with methanol (1 ml each), vortexed and centrifuged. The supernatant was collected and analyzed by fluorescence measurements (Spectrofluorimeter SLM-8000, Aminco USA). The fluorescence emission spectra were recorded in a range of 650-850 nm, with excitation at 520 nm. Fluorescence of methanol and untreated blood extracts were used as blanks. A calibration curve with known concentrations of the sensitizer was prepared.

(x) Biodistribution. Wistar rats (n=2) were anesthetized and compound 5 of the invention (0.6 mg/kg) was injected into their tail vein. The control group (n=2) was not treated with the sensitizer. At 30 min and 24 h after injection, rats (one for each time-point), were sacrificed and samples of the indicated organs or tissues (heart, liver, lung, spleen, kidney, brain, testes, skin, muscle and fat) were collected into and weighed in pre-weighted vials, immediately frozen on dry ice and stored at −200 in the dark until analyzed. For examination, each sample was thawed, weighed again, and homogenized (Polytron, Kinematica GmbH or Ultra-Turrax) in ice-cold water. The vials were then frozen in liquid nitrogen and lyophilized. The lyophilized samples were extracted with methanol (5-10 ml) in an amount equivalent to the tissue weight, and then vortexed and centrifuged. The supernatant was collected and analyzed and fluorescence measured as described in (ix) above. The fluorescence of methanol and of tissue extracts from control animals were used as blanks.

(xi) PDT Protocol. CD1 nude mice bearing C6 glioma (n=17) were anesthetized and compound 5 (0.3 mg/kg) was injected via the tail vein. The tumor area was immediately illuminated (drug-to-light time interval (DLTI)=0) transcutaneously for 15 min by 755 nm diode laser (CeramOptec, Germany) with light dose of 80 mW/cm² (light field diameter—14 mm). Following illumination the mice (n=12) were placed back in the cage. Tumor response (using local necrosis at day 8 post-PDT as end point) was recorded photographically, and tumor volume was assessed (Gleave et al., 1992.) Response was considered as partial when only a part of the illuminated tumor became necrotic. Mice were considered cured if they were tumor free 90 days after treatment. Continued tumor growth following PDT was scored as no response. Mice were sacrificed when tumor diameter reached 15 mm. The following controls were used: (i) dark control (n=3)-tumor-bearing mice i.v. injected with sensitizer but not illuminated; (ii) light control (n=2)-tumor-bearing mice not injected with sensitizer but illuminated; (iii) untreated control (n=2)-tumor-bearing mice not injected with sensitizer and not illuminated.

Example 72

Cytophotoxicity of Compounds 5, 7, 9, and 11 on Endothelial Cells

The phototoxicity of compounds 5, 7, 9, and 11 on H5V mouse endothelial cells was determined as described in section (iv) (a) above. Cells were incubated with increasing concentrations (0.001, 0.01. 0.1, 1, or 10 µM) of the compounds for 1, 6, 60, 90, 120, 240 and 480 min, washed and then illuminated or kept in the dark. The results are shown in FIGS. 3A-3C: phototoxicity of compounds 5 and 11 after 90 min incubation is shown in FIG. 3A; phototoxicity of compounds 5, 7 and 9 after 2 hours incubation is shown in FIG. 3B; and phototoxicity of compound 5 (10 µM) after incubation for 1-10 min is shown in FIG. 3C. As can be seen in the figures, the sensitizers are fast acting, their phototoxicity is concentration- and light-dependent, and their $LD_{50}$ is about the same (3 and ~0.2 µM after ~3 min and 2 h of preincubation, respectively). No dark toxicity was observed for the range of concentration tested.

Example 73

Pharmacokinetics and Biodistribution of Compound 5

The pharmacokinetics and biodistribution of the sensitizer 5 were determined in vivo in Wistar rats as described in sections (ix) and (x) above.

Figure 5A:
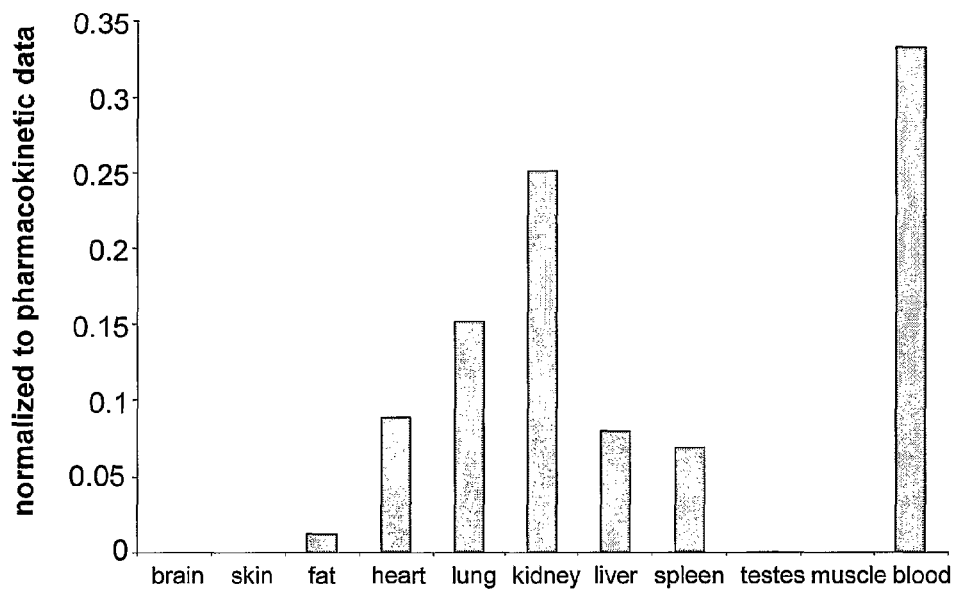
FIGS. 5A-5B show biodistribution of compound 5 in Wistar rat. Rats were sacrificed 30 min (FIG. 5A) or 24 hours (FIG. 5B) following compound 5 i.v. injection (0.6 mg/kg), and fluorescence emission spectra of the indicated organs and tissues were recorded and normalized to the pharmacokinetic data.
Figure 5B:
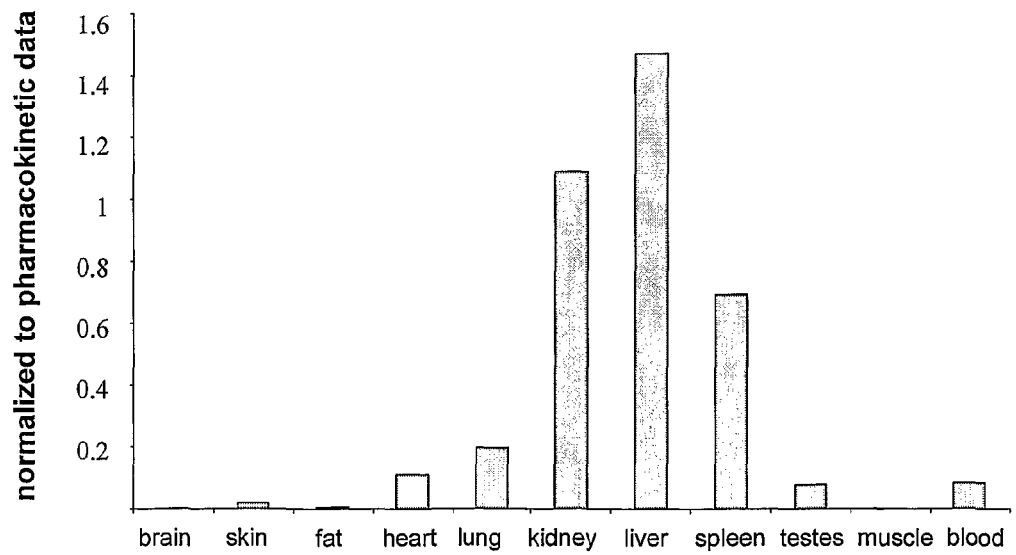

The results of the pharmacokinetics, as depicted in FIG. 4, show that about 60% of the sensitizer 5 cleared within 30 min after i.v. injection (0.6 mg/kg). The clearance kinetics indicates a bicompartmental distribution 24 h after i.v. administration The results of the biodistribution, as depicted in FIGS. 5A-5B, show that 30 min after injection the levels of the sensitizer 5 are relatively high in the blood, kidneys and lungs (FIG. 5A), and 24 h after injection the level of the sensitizer drops to almost background level in the blood but significant levels were still found in the kidneys, liver and spleen (FIG. 5B).

Example 74

Photodynamic Treatment of C6 Glioma Xenografts in CD1 Nude Mice With Compound 5

Figure 6A:
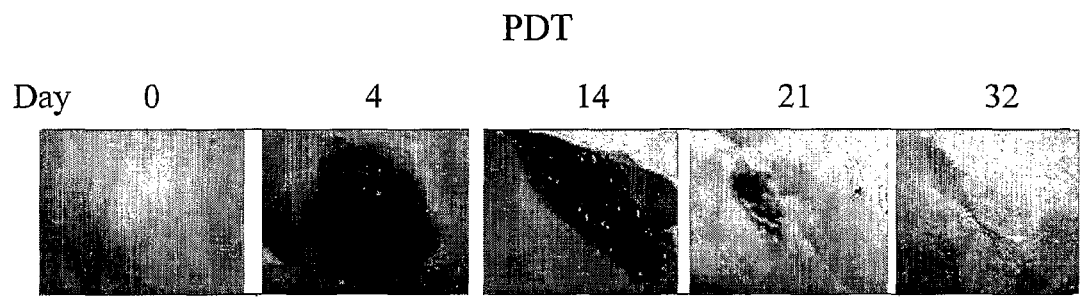
FIGS. 6A-6C are photographs showing the local effect of PDT in mice bearing C6 glioma xenograft and treated i.v. with compound 5. CD1 male nude mice were treated with 0.3 mg/kg of 5 and illuminated with 755 nm laser (80 mW/cm$^2$) for 15 min.
Figure 6B:
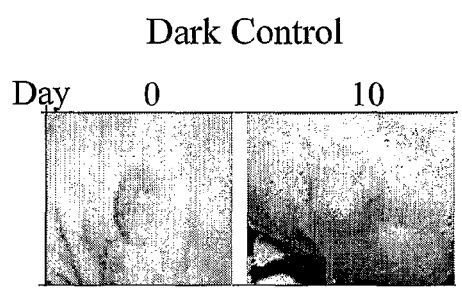
Figure 6C:
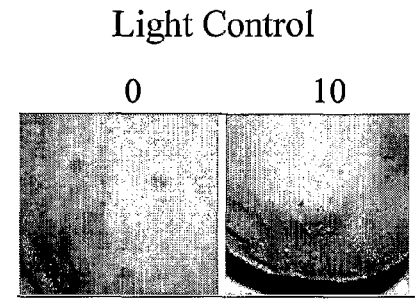

Based on the pharmacokinetic data described in Example 20 above, the treatment protocol for compound 5 was set to 15-min illumination immediately after injection of the sensitizer, using a dedicated medical laser matched to the peak absorption of 5 (CeramOptec, Germany, 755 nm). In order to test the drug efficiency, CD1 male nude mice (n=12) were treated with a dose of 0.3 mg/kg compound 5 and light intensity of 80 mW/cm$^2$. All animals in the light-and-drug (full) treatment group developed inflammation and edema at day 1 after treatment. FIG. 6A shows photographs of the tumor site of a PDT-treated mice at days 0, 4, 14, 21 and 32. Tumor development was observed at day 4 and tumor necrosis was observed at day 14. By day 21, tumor flattening was observed with a scab covering the wound. By day 32, the wound healed and the animal was cured. FIGS. 6B-6C are photographs of the tumor site of a mice injected with compound 5 but not illuminated and of a mice injected with saline and illuminated, respectively. No necrosis of the tumor occurred in both cases.

Figure 7:
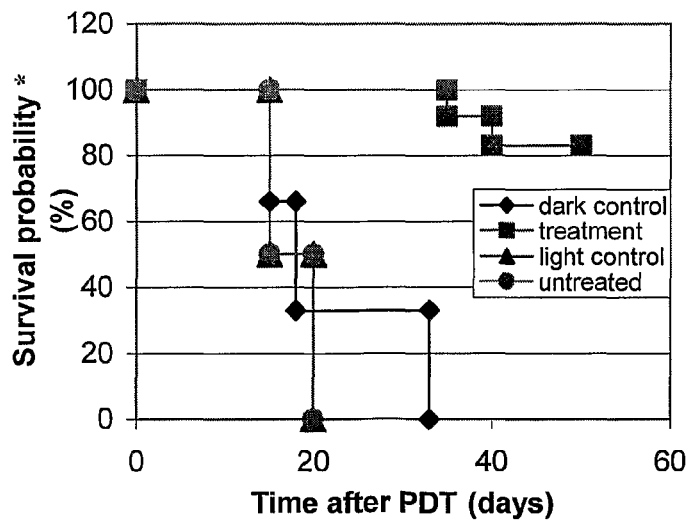
FIG. 7 shows the survival probability of mice bearing C6 glioma xenografts treated by PDT with compound 5. Mice bearing C6 glioma xenografts (n=17) were i.v. injected with compound 5 (0.3 mg/g) and immediately illuminated for 15 min with light intensity of 80 mW/cm$^2$ (full treatment group, n=12, squares). Control groups: untreated tumor-bearing mice (n=2, circles), dark control (n=3, diamonds), light control (n=2, triangles). *probability of tumor volume<2 ml.

FIG. 7 depicts a Kaplan-Meier survival curve showing 80% survival for mice treated with compound 5 and illuminated (treatment, squares).

Example 75

Figure 8A:
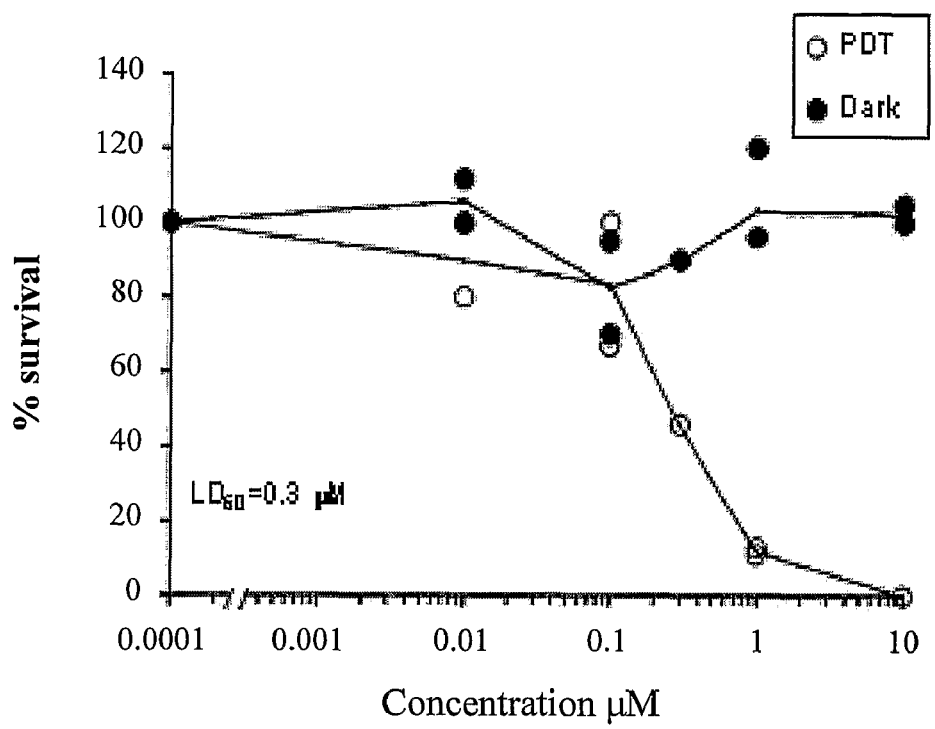
FIGS. 8A-8D are graphs showing the phototoxicity of a negatively charged bacteriochlorophyll derivative (see Example 22) and compound 5 on Gram-positive and Gram-negative bacteria. Gram-positive (St. albus, FIGS. 8A, 8B) and Gram-negative (E. coli, FIGS. 8C, 8D) bacteria were incubated for 1 hour with the indicated concentrations of the negatively charged bacteriochlorophyll derivative (FIGS. 8A, 8C) or with compound 5 (FIGS. 8B, 8D), and illuminated for 15 min with 70 mW/cm$^2$. Bacterial survival was determined by colony counting. Triplicate determinations were conducted and representative experiments are shown.
Figure 8B:
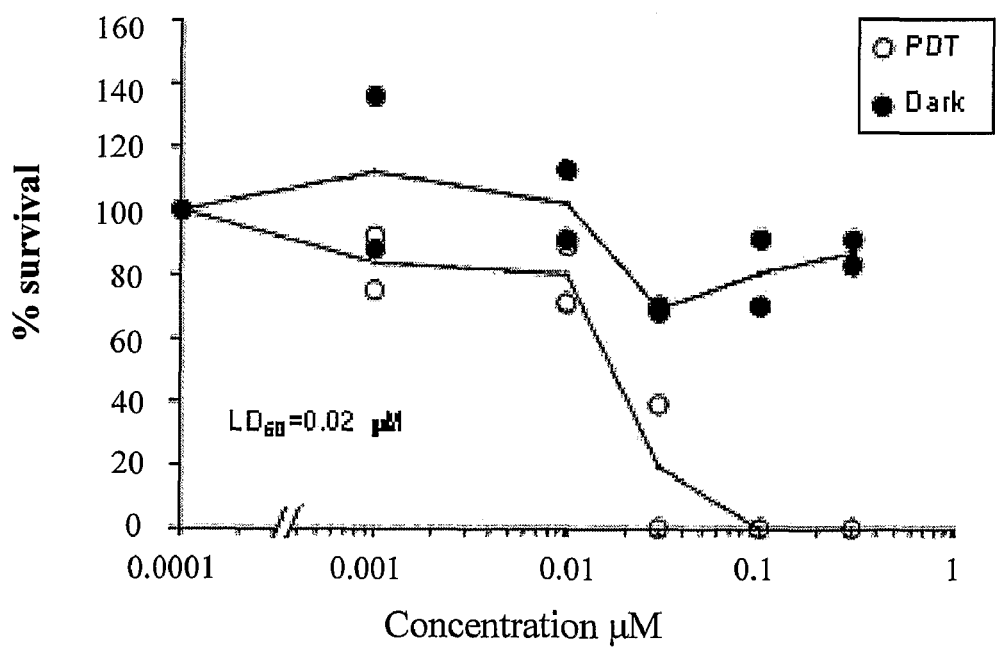
Figure 8C:
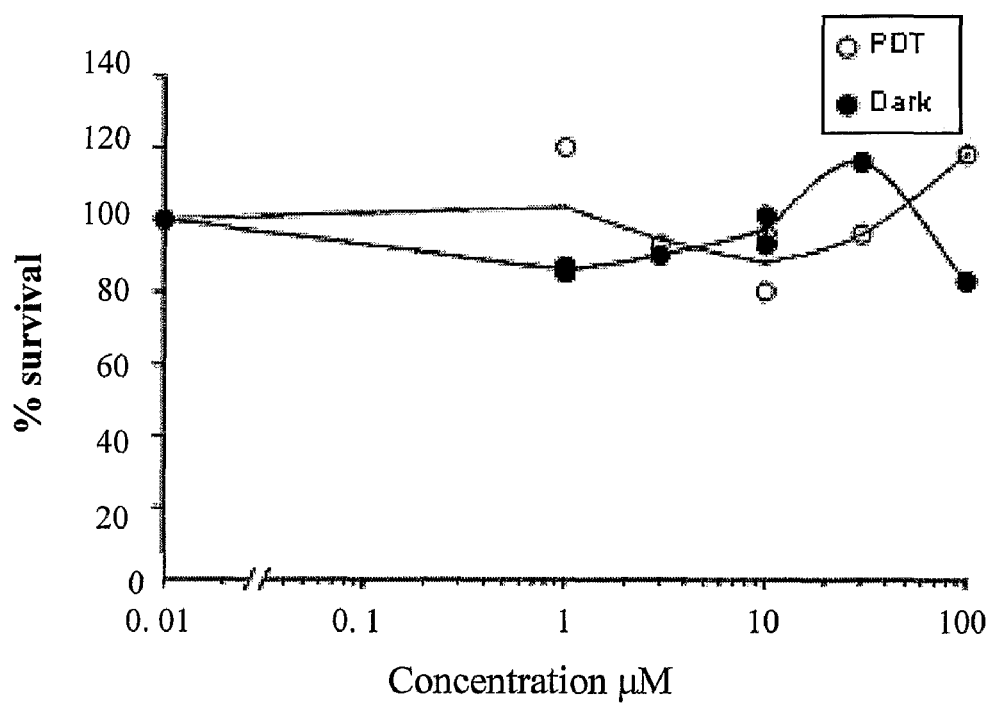
Figure 8D:
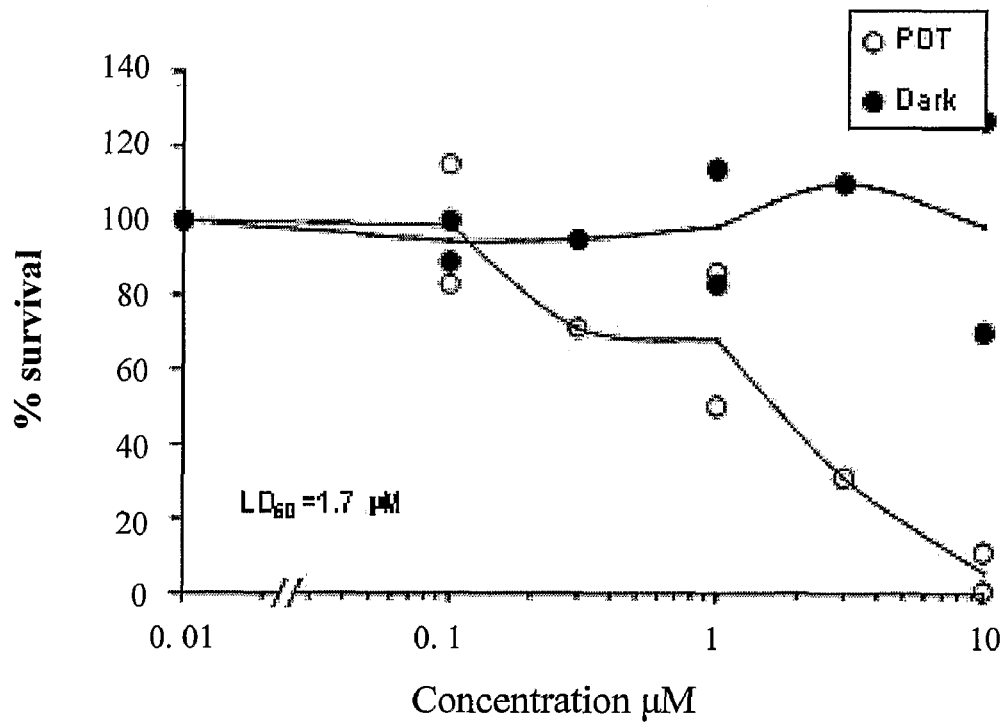
Figure 9A:
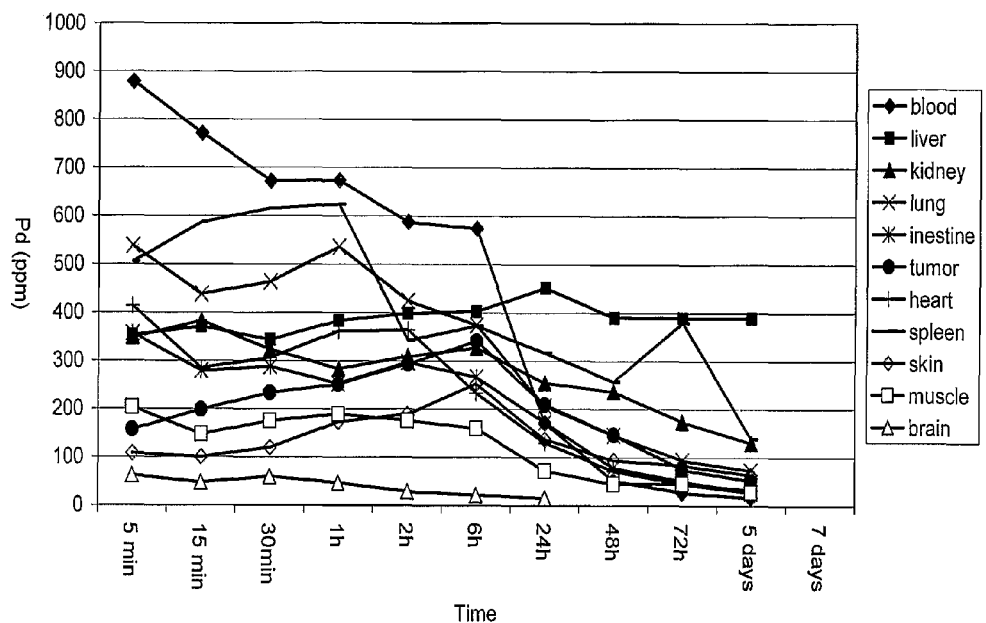
FIGS. 9A-9E are graphs showing the biodistribution of the compounds 28, 32, 10, 36, and 75, respectively, in several organs of nude mice bearing renal cell carcinoma (RCC) xenograft. The rats were injected with a solution of the test compound in isotonic mannitol (1.5 mg/kg) at different time points.
Figure 9B:
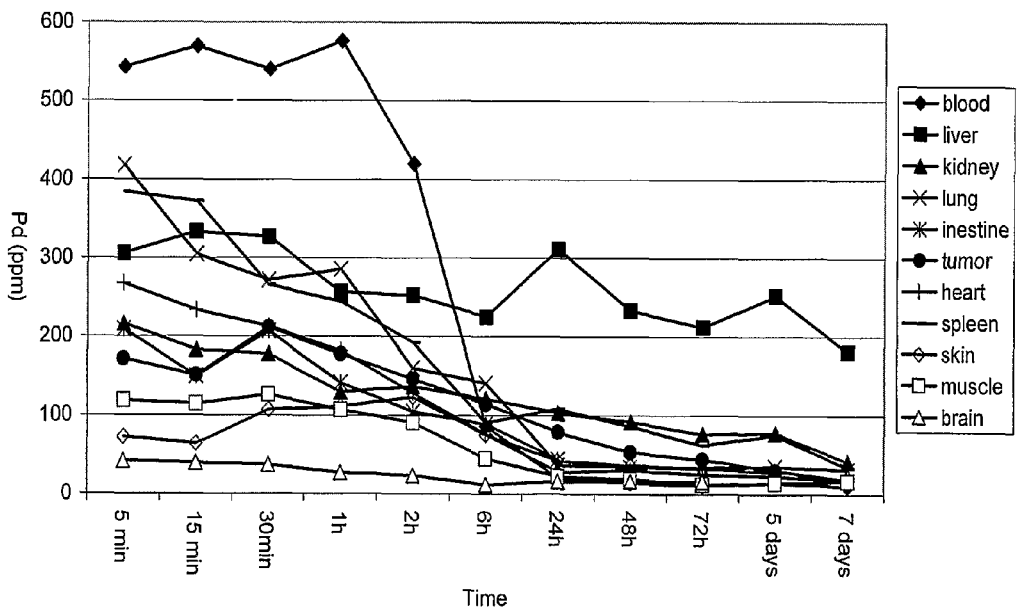
Figure 9C:
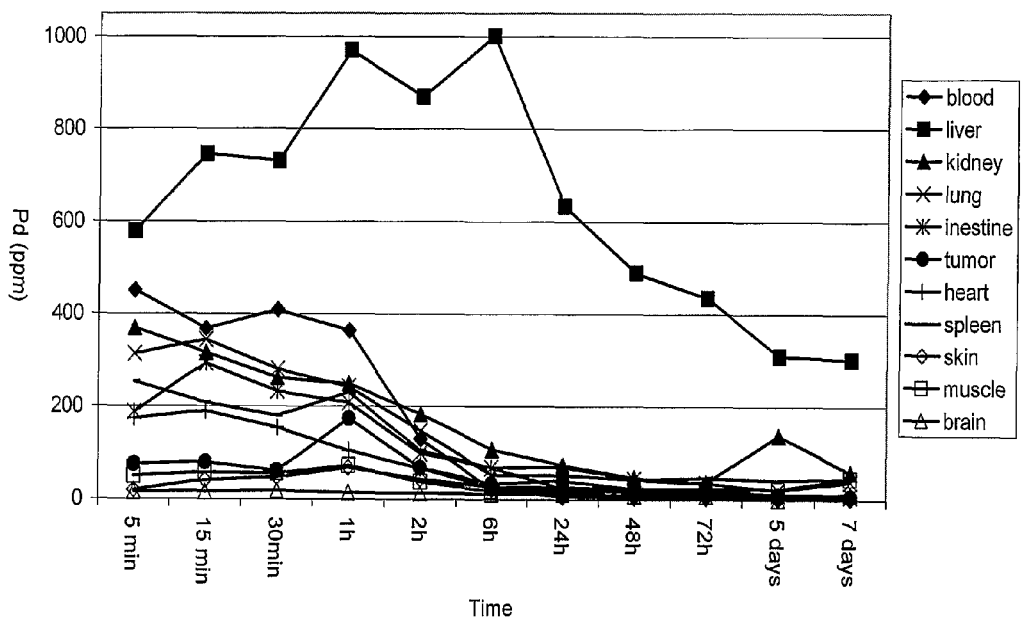
Figure 9D:
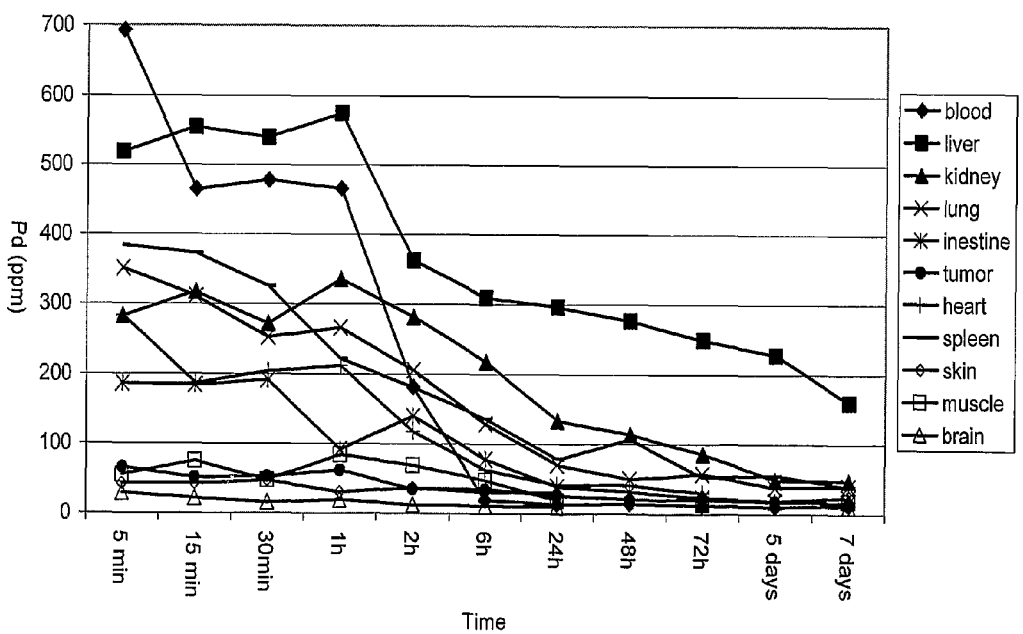
Figure 9E:
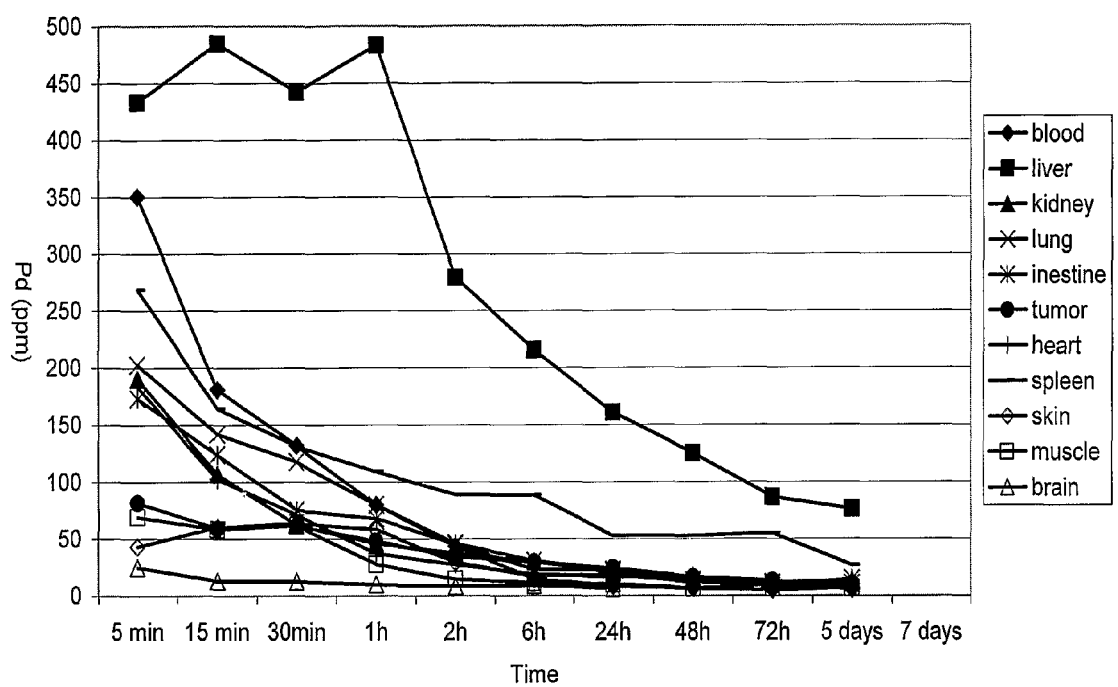

Phototoxicity of Compound 5 Against Gram-Positive and Gram-Negative Bacteria The phototoxicity of positively-charged compound 5 was tested on Gram-positive St. albus and Gram-negative E. coli bacteria in comparison to the negatively-charged Pd 3$^1$-oxo-15-methoxycarbonylmethyl-Rhodobacteriochlorin 13$^1$-(2-sulfoethyl)amide dipotassium salt (described in PCT/IL03/00973). Bacteria were incubated with increasing concentrations of the sensitizers for 1 h and illuminated or kept in the dark. The results, depicted in FIGS. 8A-8D, show that the positively-charged sensitizer compound 5 was phototoxic against both the Gram-positive St. albus (FIG. 8B) ($K_d$ 0.02 µM) and Gram-negative E. coli (FIG. 8D) ($K_d$ 1.7 µM) bacteria, whereas the negatively-charged sensitizer of the prior art was effective against the Gram-positive St. albus (FIG. 8A) ($K_d$ 0.3 µM), but not against Gram-negative E. coli (FIG. 8C). Nearly 100% death of E. coli was observed with 10 µM of compound 5 (FIG. 8D). Gram-positive bacteria St. albus, was 100 times more sensitive to compound 5 than Gram-negative E. coli. No phototoxicity was observed when bacteria were incubated and treated with the same sensitizers' concentration range without illumination (dark controls).

Example 76

Phototoxicity Assay

The materials and methods are as described in the Biological Section above.

H5V cells (40×10$^3$/well) were cultured in 96-well plates for 24 h to ~80% confluence. To determine phototoxicity, the culture medium was replaced with 100 µl/well medium, in the absence or presence of 10$^{-8}$ to 10$^{-6}$ M sensitizer, and incubated in the dark for 15 min or 3 h in the culture incubator. The plates (PDT group) were then placed in the light field at room temperature and illuminated from the bottom for 10 min (800>λ>650 nm, 12 J/cm$^2$). After illumination, the medium was changed to fresh culture medium. The cultures were then placed in the culture incubator and cell survival was determined 24 h later, using the neutral red survival assay described below.

The following controls were used:
1. Light control: cells were illuminated in the absence of sensitizer.
2. Dark control: cells were treated with sensitizer but kept in the dark.

Untreated: cells were kept in the dark without any treatment.

Following 24 h post PDT the culture medium in the wells was replaced with 100 µl fresh medium containing 40 µg/ml neutral red. The plate was incubated for 1.5 h in a dark culture incubator. The medium was aspirated and the cells washed with 100 µl of solution containing 1% CaCl$_2$ and 0.5% formaldehyde, which removes the unincorporated dye and fixes the cells to the substratum. The dye was then extracted from the cells into the supernatant upon addition of 100 µl 1% glacial acetic acid in 50% ethanol. After 1-2 min at room temperature, the optical density of the wells was determined in a microplate spectrophotometer using a 570 nm filter. After subtraction of assay blanks, net optical density was computed as the average value of triplicate determinations. Cell survival was calculated as the percent of the dye accumulated in the untreated control. To determine cell survival data was plotted against sensitizer concentration. These curves were then used to calculated LD$_{50}$ values.

Following synthesis, the compounds described in the Examples 23 to 75 above were purified, divided into equal aliquots and lyophilized for storage (desiccated at −20° C.). The exact material content was determined by HPLC-diode array detection, and the PDT efficacy was evaluated at two incubation times as described in the experimental section. The results are presented in Tables 1-3 below:

TABLE 1

| Compound | IC$_{50}$ (μM) 3 hours | IC$_{50}$ (μM) 15 min |
| --- | --- | --- |
| 24 | 1.2 | 2.4 |
| 25 | 0.75 | 1.1 |
| 26 | 0.45 | 1.0 |
| 27 | 0.45 | 1.5 |
| 28 | 0.38 | 1.3 |
| 29 | 1.9 | 1.9 |
| 30 | 0.61 | 1.7 |
| 31 | 0.60 | 2.6 |
| 32 | 0.25 | 0.60 |

All of the compounds prepared according to the invention showed better solubility in comparison to Pd-Bpheid, 3. Most of the compounds require low percentages of Cremophor in isotonic mannitol to form 100% monomeric solution at 2 mg/ml while some of the compounds require low concentrations of propylene glycol or PEG-400 to obtain the same monomeric solution (both additives are considered very safe for use), The zwitterionic nature of these compounds may be a contributing factor for the need for Cremophor to generate a monomeric solution.

The synthesis of compounds 25-32 is much simpler than that of the original mono-cation taken as the reference and reproduced herein as 24. Noteworthy are the PDT activities of compounds 26, 28, and 32 (for example 32 is about 4-5 times more active than 24 at both incubation times).

TABLE 2

| Compound | IC$_{50}$ (μM) 3 hours | IC$_{50}$ (μM) 15 min |
| --- | --- | --- |
| 33* | 0.45 | 0.75 |
| 34 | 0.20 | 0.48 |
| 35 | 0.21 | 1.23 |
| 10 | 0.24 | 0.74 |
| 36 | 0.15 | 0.37 |
| 37 | 0.21 | 0.75 |
| 38 | 0.16 | 0.44 |
| 39 | 1.10 | 2.44 |
| 40 | 0.35 | 0.70 |
| 41 | 0.46 | 1.13 |
| 42 | 0.28 | 0.68 |
| 43 | 0.18 | 0.60 |
| 44 | 0.17 | 1.41 |
| 45 | 0.18 | 0.20 |

The synthesis of compounds 34-45 is much simpler than that of the original di-cation taken as a reference and reproduced herein as 33. Noteworthy are the PDT activities at short incubation time of 34, 36, 38 and 45 (for example, 36 is more active at 15 min. incubation time then 33 is at 3 hours).

TABLE 3

| Compound | IC$_{50}$ 3 hours (μM) | IC$_{50}$ 15 min (μM) |
| --- | --- | --- |
| 46 | 0.60 | 1.33 |
| 47 | 0.25 | 0.45 |
| 48 | 0.20 | 0.60 |
| 49 | 0.57 | 1.15 |
| 50 | 0.17 | 0.47 |
| 51 | 0.40 | 0.78 |
| 52 | 0.89 | 0.83 |
| 53 | 0.90 | 2.00 |
| 54 | 0.27 | 0.75 |
| 55 | 0.43 | 1.07 |
| 56 | 0.32 | 0.79 |
| 57 | 0.60 | 1.33 |
| 58 | 0.37 | 0.64 |
| 59 | 0.19 | 0.45 |
| 60 | 0.24 | 0.62 |
| 61 | 0.21 | 0.69 |
| 62 | 0.19 | 0.63 |
| 63 | 0.21 | 0.66 |
| 64 | 0.17 | 0.56 |
| 65 | 0.22 | 0.43 |
| 66 | 0.20 | 0.55 |
| 67 | 0.18 | 0.50 |
| 68(R) | 0.16 | 0.50 |
| 69(S) | 0.16 | 0.50 |
| 70 | 0.16 | 0.55 |
| 73 | 0.30 | 0.38 |
| 74 | 0.29 | 0.74 |
| 75 | 0.16 | 0.50 |

All of the compounds of the above table showed better solubility in comparison to Pd-Bpheid, 3. Most of the compounds only require low percentages of propylene glycol or PEG-400 to form 100% monomeric solution at 2 mg/ml. Although the synthesis of most compounds requires a two or three chemical transformations, most of the compounds may be prepared in one pot reactions with minimal intermediate purifications and isolations (in the examples presented herein, preparative HPLC was used in many reactions during intermediate and final purification steps, simply for convenience. Simple extractions and precipitations have also been successfully employed to purify these compounds, thus circumventing the need for expensive and tedious large scale HPLC purification.

Example 77

Biodistribution of the Compounds

The animals were CD1 Nude male mice bearing RCC xenografts. Three animals were used for each time point. Compounds 28, 32, 10, 36, and 75 were used in the experiments.

Anaesthesia was made with ketamine:xylazine (85:15, vol/vol).

Anaesthetized animals were injected with a solution of the test compound (2 mg/ml) in isotonic mannitol at a dose of 1.5 mg/kg. Three animals were sacrificed at each time point and samples of blood, heart, lung, liver, kidney, intestine, spleen, muscle, skin, tumor and brain were collected. The time points used were 5 min, 15 min, 30 min, 1 h, 2 h, 6 h, 24 h, 48 h, 72 h, 5 days and 7 days after injection. Samples were accurately weighed, dissolved in concentrated nitric acid and analyzed for Palladium by ICPMS.

The results are represented in the graphs annexed herewith (FIGS. 9A to 9E).
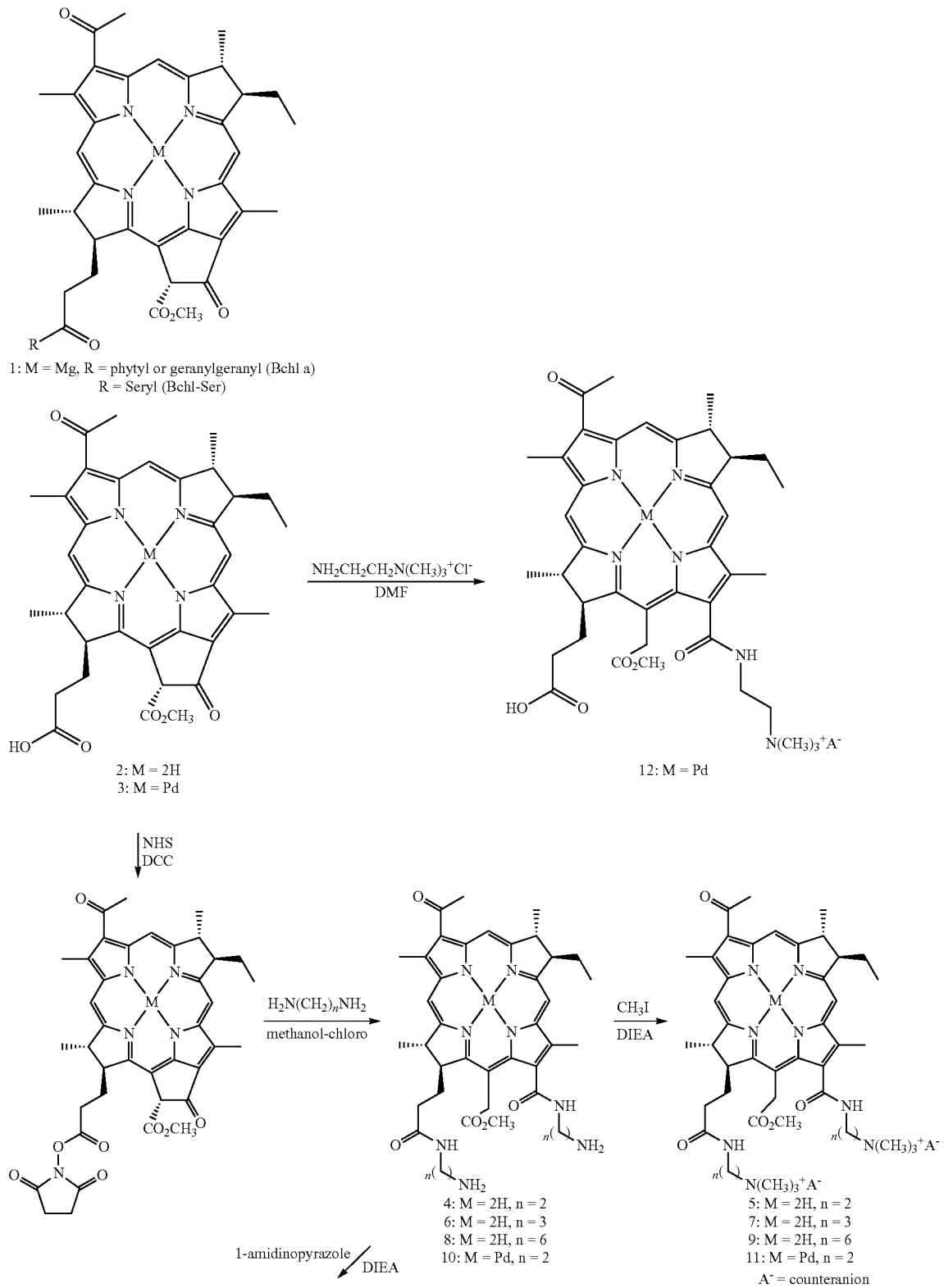
Scheme I

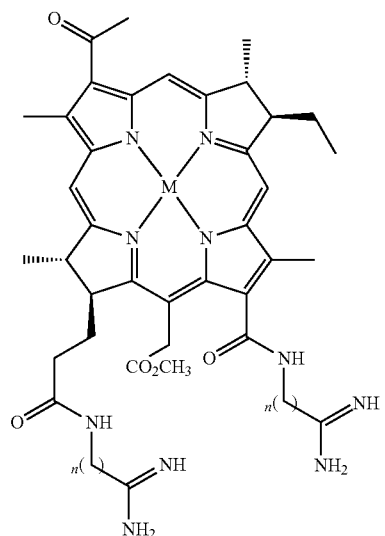
14: M = Pd, n = 2
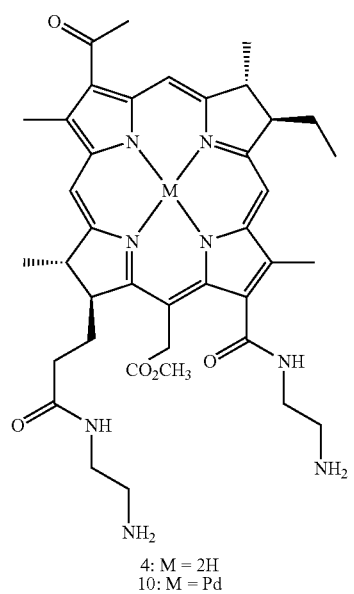
Scheme 2
4: M = 2H
10: M = Pd
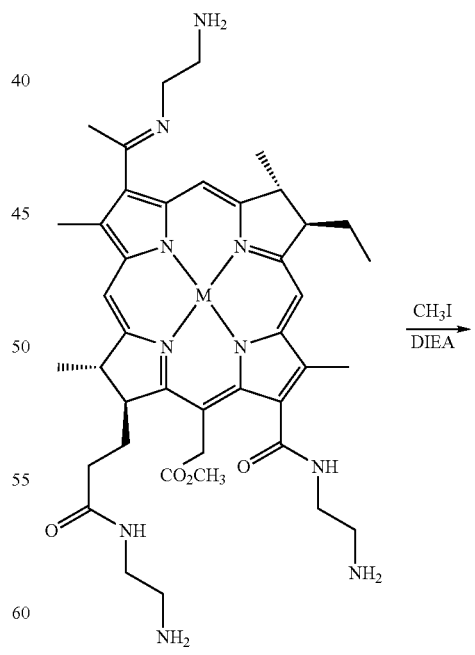
20: M = 2H
21: M = Pd -continued
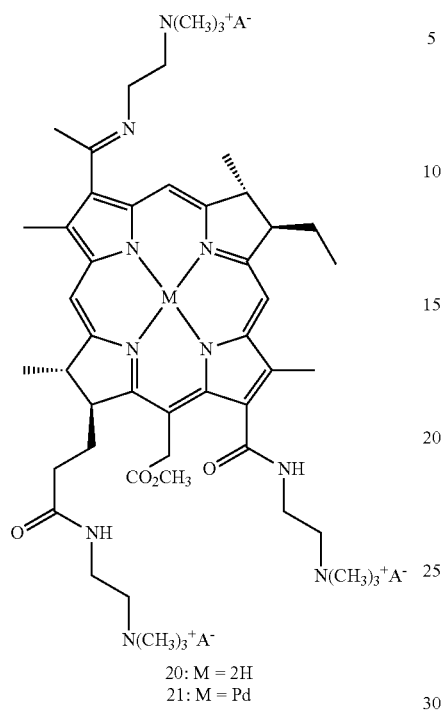
20: M = 2H
21: M = Pd
APPENDIX
Table of Compounds 24-75
| Compound No. | Compound Name | Chemical Structure |
|---|---|---|
| 24 | Palladium $3^1$-oxo-15-methoxycarbonylmethyl-Rhodobacteriochlorin-$13^1$-(2-$N^3$-trimethylammoniumethyl)amide acetate (salt) | 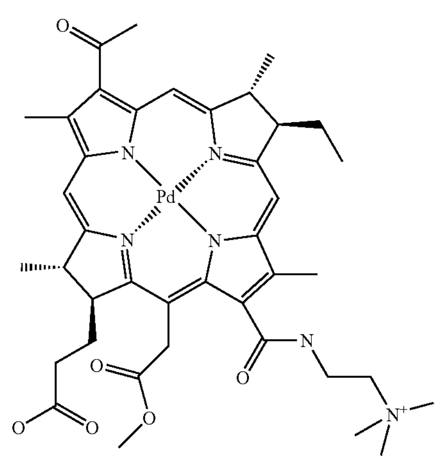 |

| Compound No. | Compound Name | Chemical Structure |
|---|---|---|
| 25 | Palladium $3^1$-oxo-15-methoxycarbonylmethyl-Rhodobacteriochlorin-$13^1$-(2-$N^2$-dimethylaminoethyl)amide | 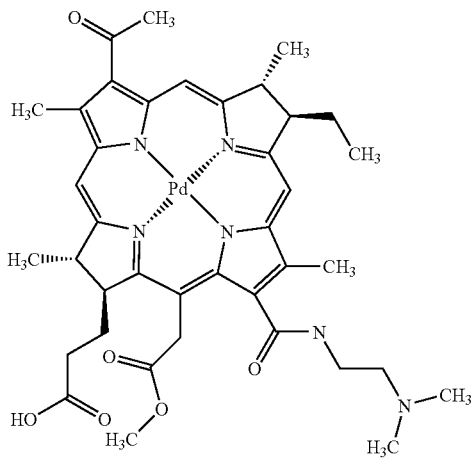 |
| 26 | Palladium $3^1$-oxo-15-methoxycarbonylmethyl-Rhodobacteriochlorin-$13^1$-(3-$N^2$-dimethylaminopropyl)amide | 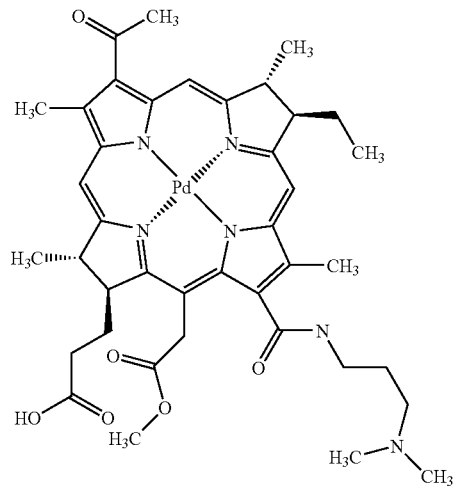 |
| 27 | Palladium $3^1$-oxo-15-methoxycarbonylmethyl-Rhodobacteriochlorin-$13^1$-(2-[(2-aminoethyl)amino]ethyl)amide | 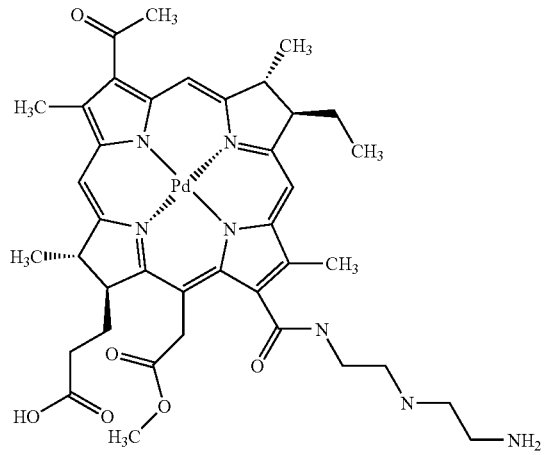 |

| Compound No. | Compound Name | Chemical Structure |
|---|---|---|
| 28 | Palladium $3^1$-oxo-15-methoxycarbonylmethyl-Rhodobacteriochlorin-$13^1$-([2-bis(2-aminoethyl)amino]ethyl) amide | 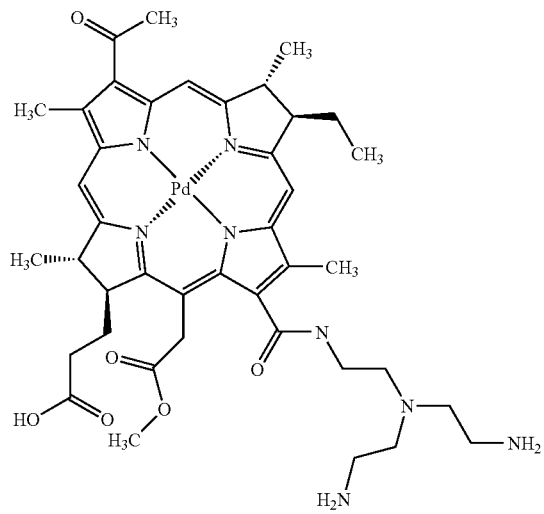 |
| 29 | Palladium $3^1$-oxo-15-methoxycarbonylmethyl-Rhodobacteriochlorin-$13^1$-(2-morpholino-N-ethyl)amide | 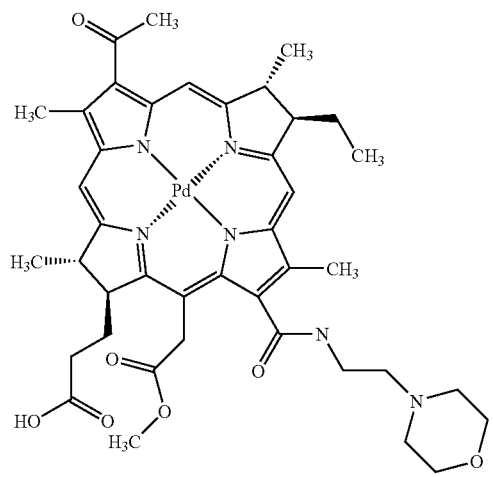 |
| 30 | Palladium $3^1$-oxo-15-methoxycarbonylmethyl-Rhodobacteriochlorin-$13^1$-(2-piperazino-N-ethyl)amide | 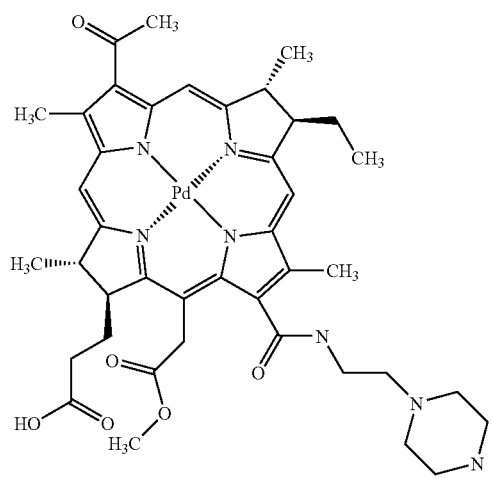 |

-continued

| Compound No. | Compound Name | Chemical Structure |
|---|---|---|
| 31 | Palladium $3^1$-oxo-15-methoxycarbonylmethyl-Rhodobacteriochlorin-$13^1$-(2-[(2-$N^2$-diethylaminoethyl)amino]ethyl) amide | 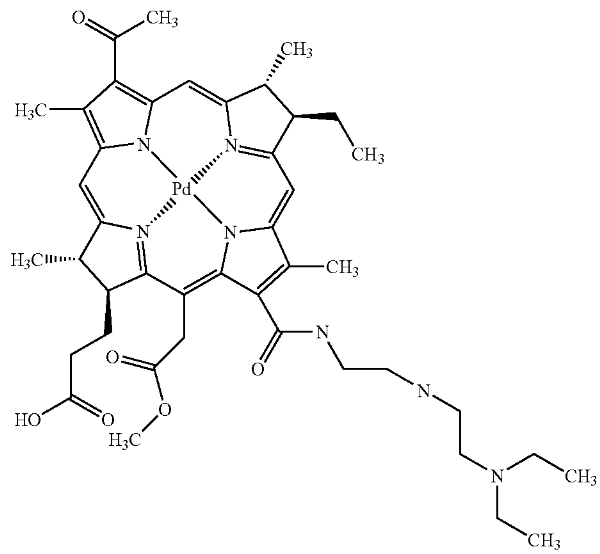 |
| 32 | Palladium $3^1$-oxo-15-methoxycarbonylmethyl-Rhodobacteriochlorin-$13^1$-(3-[(3-aminopropyl)amino]propyl)amide | 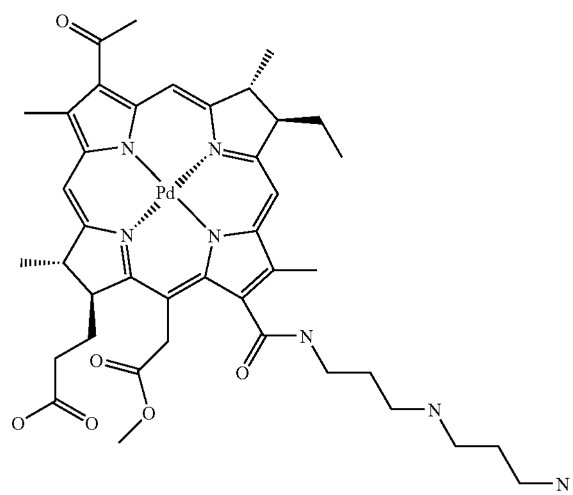 |
| 33 | Palladium $3^1$-oxo-15-methoxycarbonylmethyl-Rhodobacteriochlorin-$13^1$,$17^3$-di(2-$N^3$-trimethylammoniumethyl) amide diacetate salt | 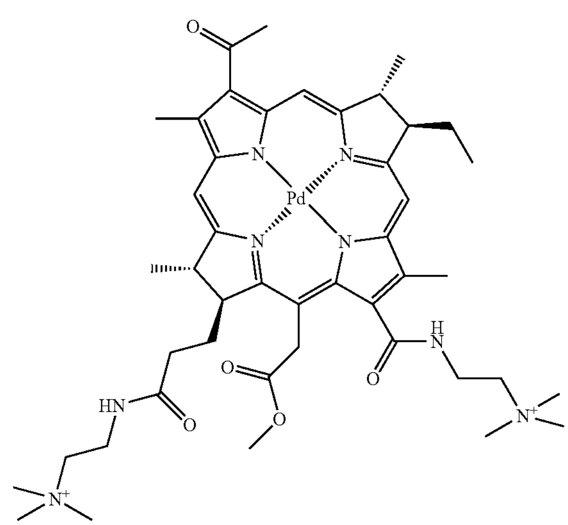 |

| Compound No. | Compound Name | Chemical Structure |
|---|---|---|
| 34 | Palladium $3^1$-oxo-15-methoxycarbonylmethyl-Rhodobacteriochlorin-$13^1$,$17^3$-di(3-aminopropyl)amide | 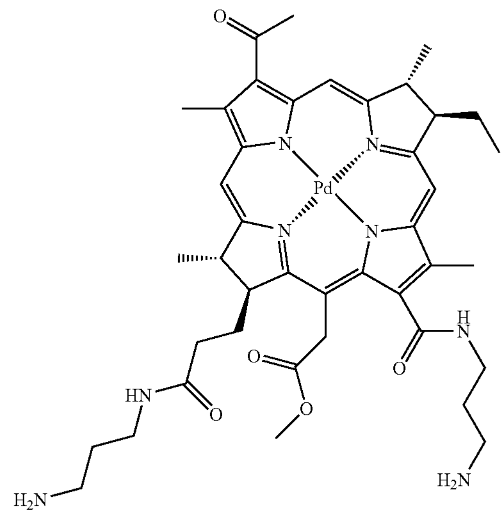 |
| 35 | Palladium $3^1$-oxo-15-methoxycarbonylmethyl-Rhodobacteriochlorin-$13^1$,$17^3$-di(4-aminobutyl)amide | 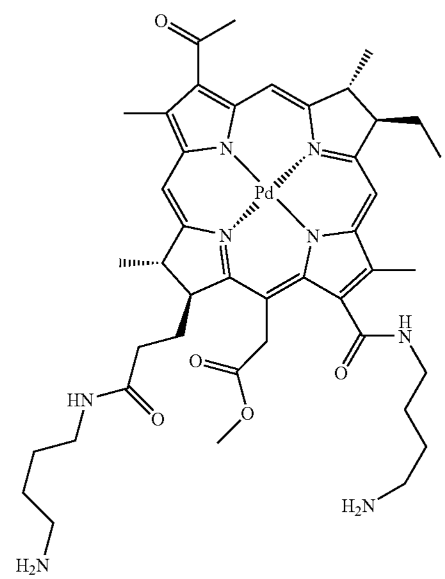 |
| 10 | Palladium $3^1$-oxo-15-methoxycarbonylmethyl-Rhodobacteriochlorin-$13^1$,$17^3$-di(2-aminoethyl)amide | 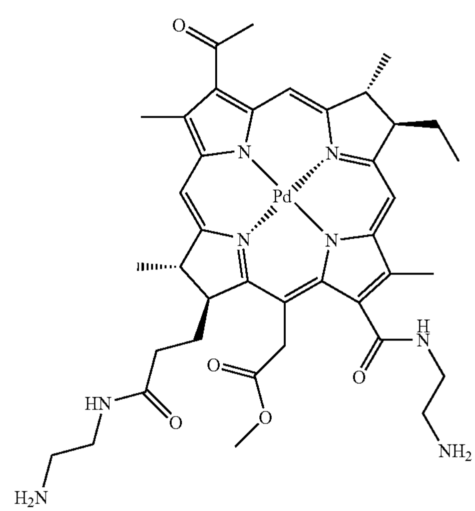 |

| Compound No. | Compound Name | Chemical Structure |
|---|---|---|
| 36 | Palladium $3^1$-oxo-15-methoxycarbonylmethyl-Rhodobacteriochlorin-$13^1$,$17^3$-di(2-$N^2$-dimethylaminoethyl)amide | 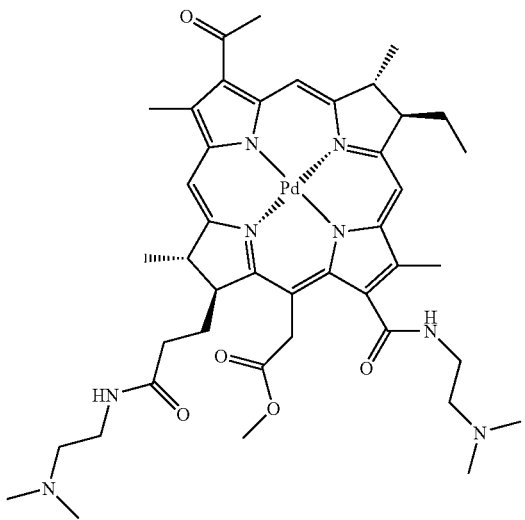 |
| 37 | Palladium $3^1$-oxo-15-methoxycarbonylmethyl-Rhodobacteriochlorin-$13^1$,$17^3$-di(3-$N^2$-dimethylaminopropyl)amide | 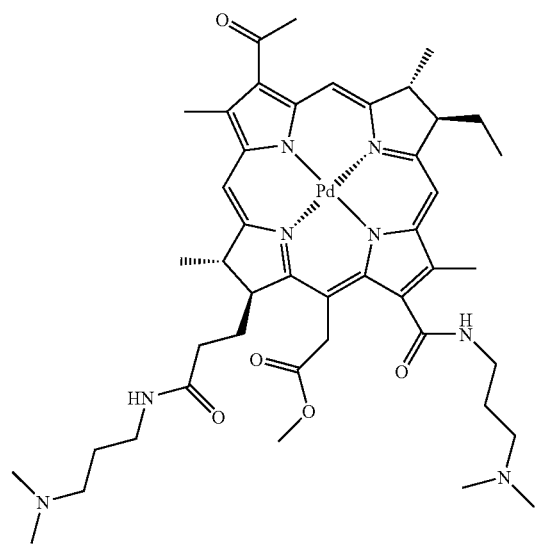 |

| Compound No. | Compound Name | Chemical Structure |
|---|---|---|
| 38 | Palladium 3$^1$-oxo-15-methoxycarbonylmethyl-Rhodobacteriochlorin-13$^1$,17$^3$-di-(2-[(2-aminoethyl)amino]ethyl)amide | 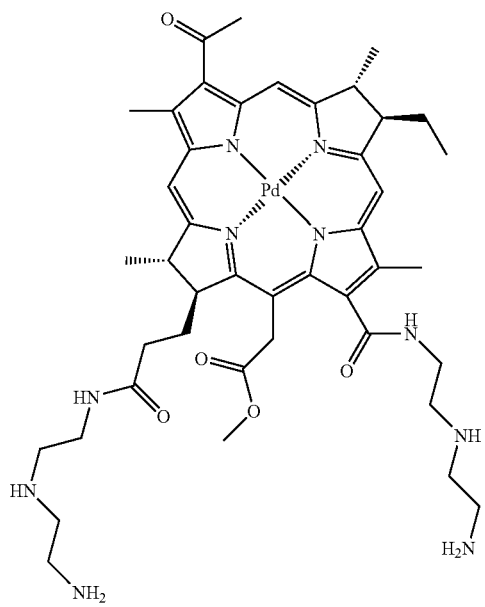 |
| 39 | Palladium 3$^1$-oxo-15-methoxycarbonylmethyl-Rhodobacteriochlorin-13$^1$,17$^3$-di-(2-[(2-N$^2$-diethylaminoethyl)amino]ethyl) amide | 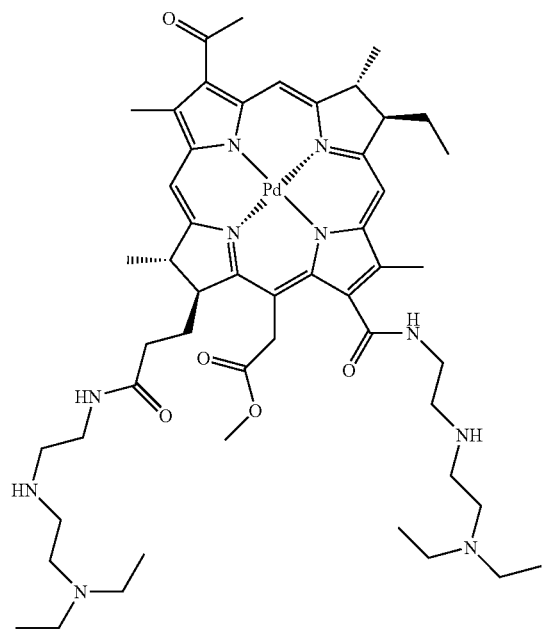 |

-continued
| Compound No. | Compound Name | Chemical Structure |
|---|---|---|
| 40 | Palladium $3^1$-oxo-15-methoxycarbonylmethyl-Rhodobacteriochlorin-$13^1$,$17^3$-di(2-morpholino-N-ethyl)amide | 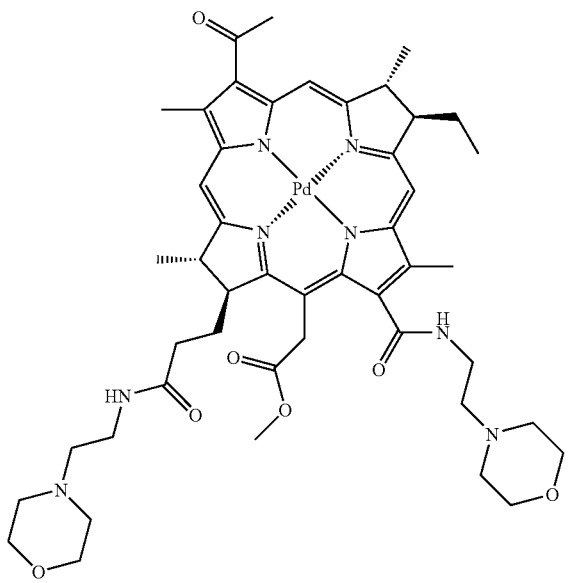 |
| 41 | Palladium $3^1$-oxo-15-methoxycarbonylmethyl-Rhodobacteriochlorin-$13^1$,$17^3$-di(2-piperazino-N-ethyl)amide | 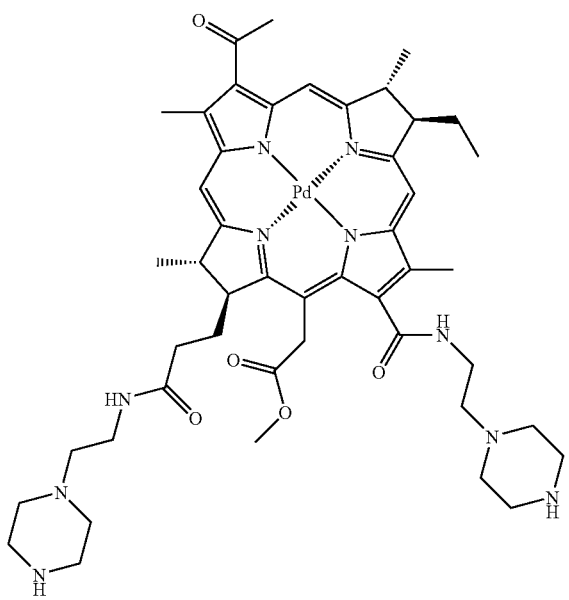 |

| Compound No. | Compound Name | Chemical Structure |
|---|---|---|
| 42 | Palladium $3^1$-oxo-15-methoxycarbonylmethyl-Rhodobacteriochlorin-$13^1$,$17^3$-di-(3-[(3aminopropyl)amino]propyl)amide | 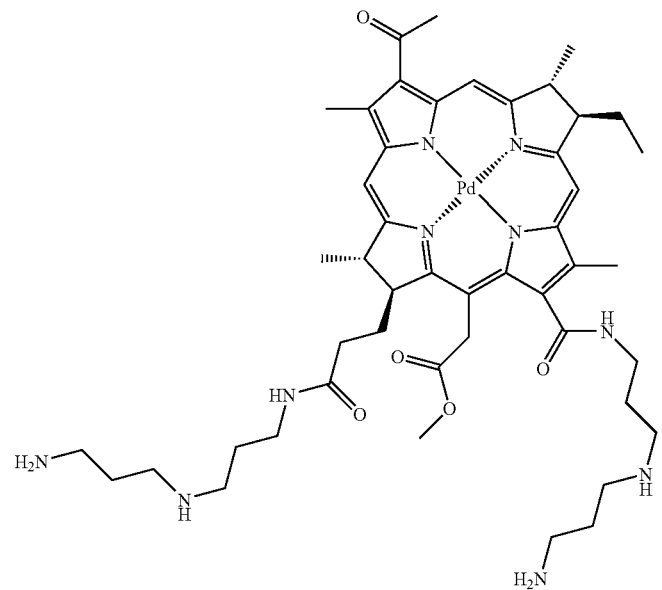 |
| 43 | Palladium $3^1$-oxo-15-methoxycarbonylmethyl-Rhodobacteriochlorin-$13^1$,$17^3$-di([2-bis(2-aminoethyl)amino]ethyl)amide | 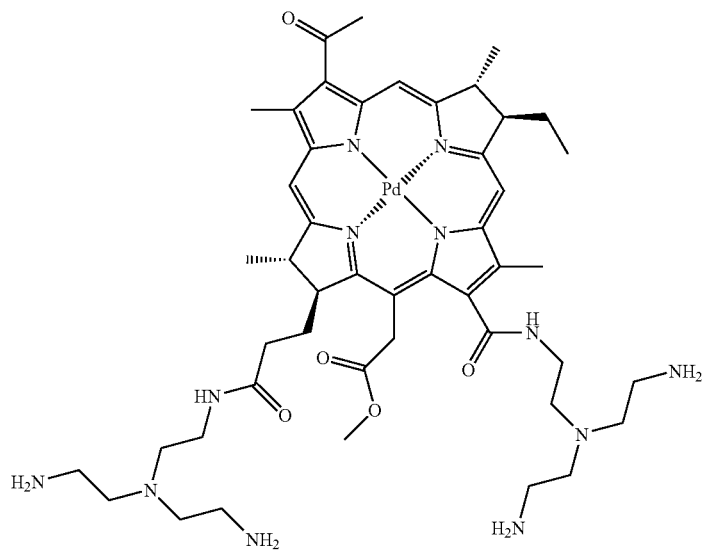 |

| Compound No. | Compound Name | Chemical Structure |
|---|---|---|
| 44 | Palladium $3^1$-oxo-15-methoxycarbonylmethyl-Rhodobacteriochlorin-$13^1$,$17^3$-di(2-N-(2'-pyridyl)aminoethyl)amide | 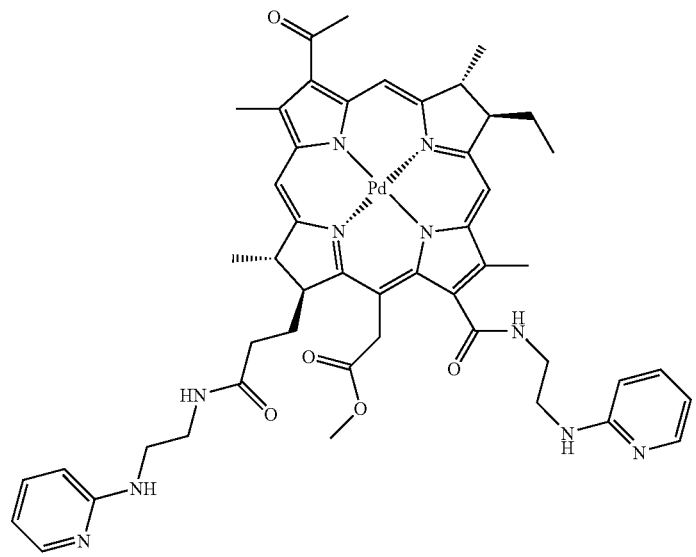 |
| 45 | Palladium $3^1$-oxo-15-methoxycarbonylmethyl-Rhodobacteriochlorin-$13^1$,$17^3$-di(2-$N^2$-diethylaminoethyl)amide | 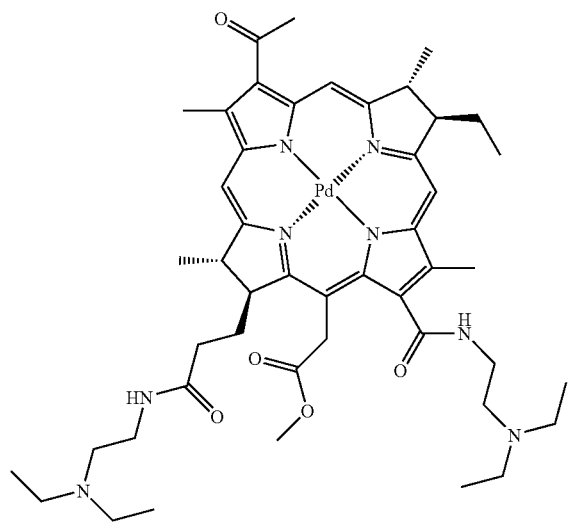 |

| Compound No. | Compound Name | Chemical Structure |
|---|---|---|
| 46 | Palladium $3^1$-oxo-15-methoxycarbonylmethyl-Rhodobacteriochlorin-$13^1$-(2,3-dihydroxypropyl)amide-$17^3$-(2-$N^3$-trimethyl ammoniumethyl)amide acetate salt | 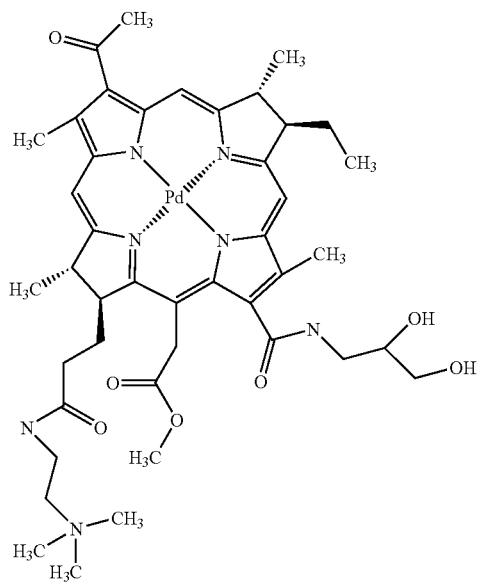 |
| 47 | Palladium $3^1$-oxo-15-methoxycarbonylmethyl-Rhodobacteriochlorin-$13^1$-(2,3-dihydroxypropyl)amide-$17^3$-(2-aminoethyl)amide | 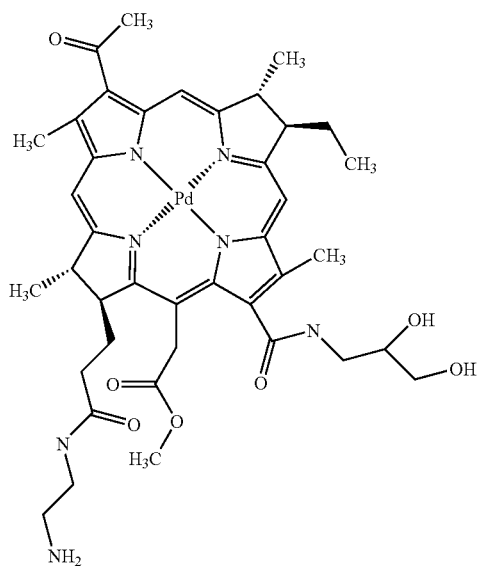 |

| Compound No. | Compound Name | Chemical Structure |
|---|---|---|
| 48 | Palladium $3^1$-oxo-15-methoxycarbonylmethyl-Rhodobacteriochlorin-$13^1$-(2-aminoethyl)amide-$17^3$-(2,3-dihydroxypropyl) amide | 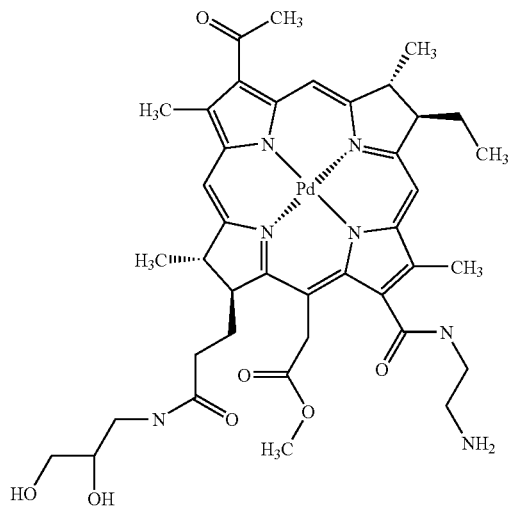 |
| 49 | Palladium $3^1$-oxo-15-methoxycarbonylmethyl-Rhodobacteriochlorin-$13^1$-(2,3-dihydroxypropyl)amide-$17^3$-(2-$N^2$-dimethyl aminoethyl)amide | 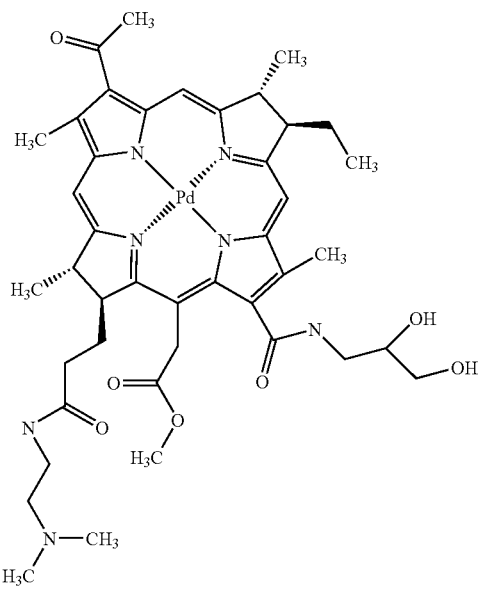 |

| Compound No. | Compound Name | Chemical Structure |
|---|---|---|
| 50 | Palladium $3^1$-oxo-15-methoxycarbonylmethyl-Rhodobacteriochlorin-$13^1$-(2-$N^2$-dimethylaminoethyl)amide-$17^3$-(2,3-dihydroxypropyl)amide | 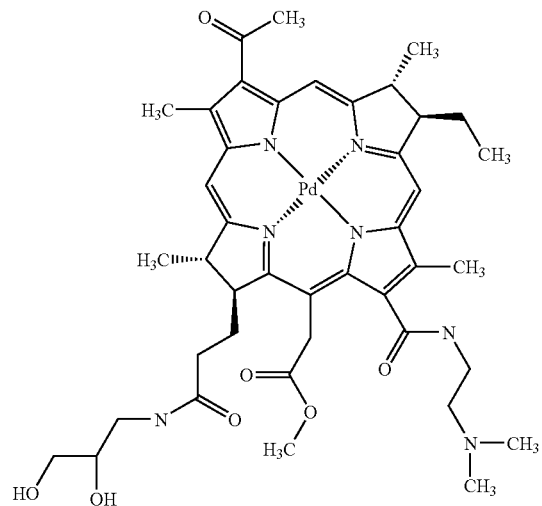 |
| 51 | Palladium $3^1$-oxo-15-methoxycarbonylmethyl-Rhodobacteriochlorin-$13^1$-(2,3-dihydroxypropyl)amide-$17^3$-(2-[(2-aminoethyl)amino]ethyl)amide | 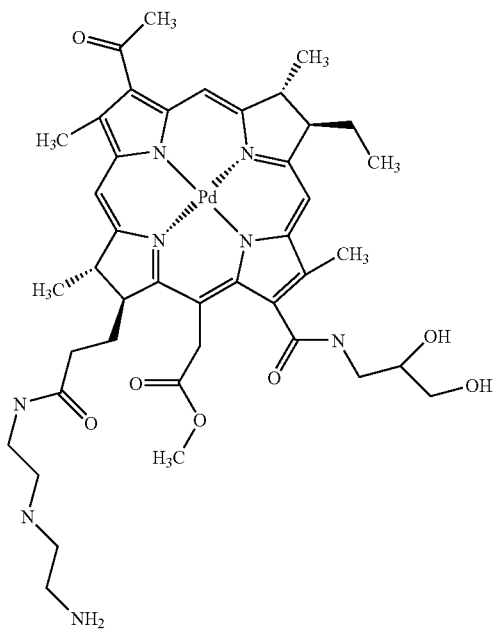 |

-continued
| Compound No. | Compound Name | Chemical Structure |
|---|---|---|
| 52 | Palladium $3^1$-oxo-15-methoxycarbonylmethyl-Rhodobacteriochlorin-$13^1$-(2,3-dihydroxypropyl)amide-$17^3$-(2-[(2-$N^2$-diethyl aminoethyl)amino]ethyl)amide | 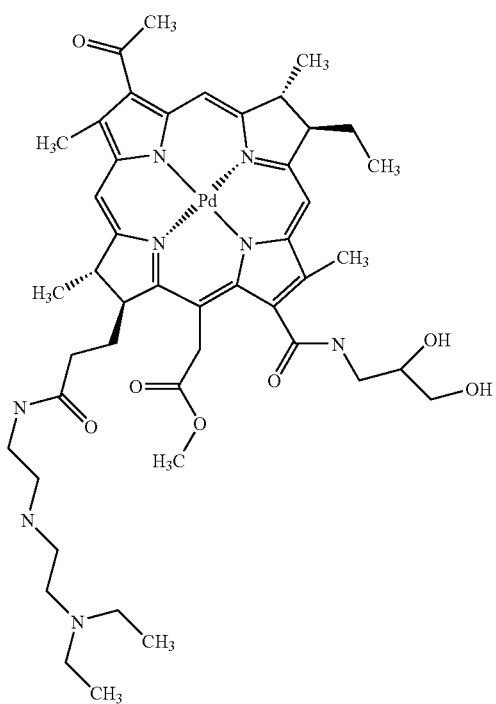 |
| 53 | Palladium $3^1$-oxo-15-methoxycarbonylmethyl-Rhodobacteriochlorin-$13^1$-(2,3-dihydroxypropyl)amide-$17^3$-(2-morpholino-N-ethyl)amide | 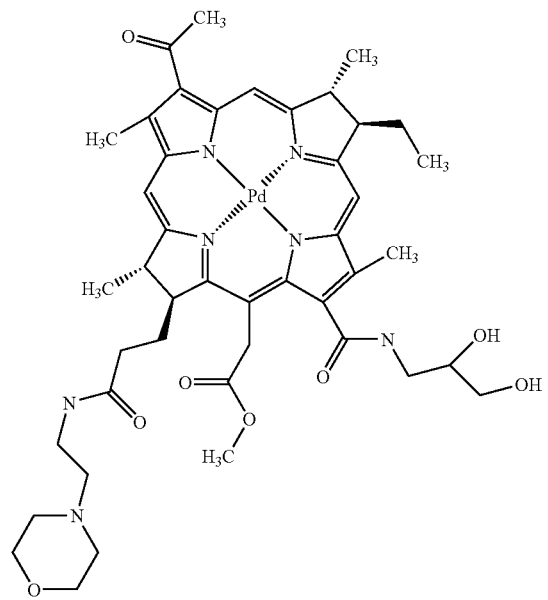 |

-continued
| Compound No. | Compound Name | Chemical Structure |
|---|---|---|
| 54 | Palladium $3^1$-oxo-15-methoxycarbonylmethyl-Rhodobacteriochlorin-$13^1$-(2,3-dihydroxypropyl)amide-$17^3$-(2-piperazino-N-ethyl)amide | 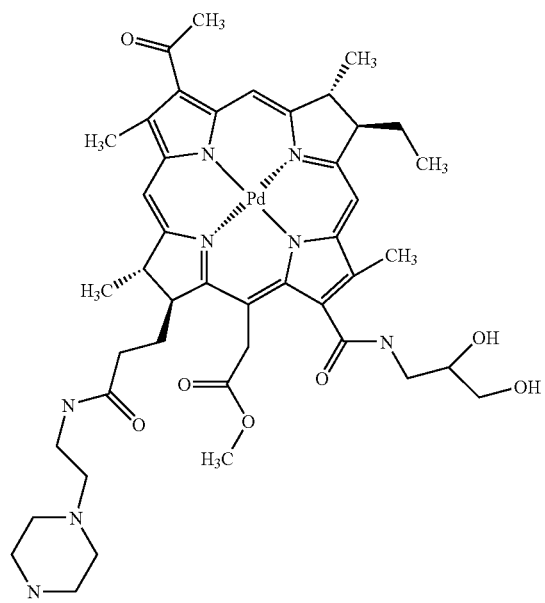 |
| 55 | Palladium $3^1$-oxo-15-methoxycarbonylmethyl-Rhodobacteriochlorin-$13^1$-(2-[(2-aminoethyl)amino]ethyl)amide-$17^3$-(2,3-dihydroxypropyl)amide | 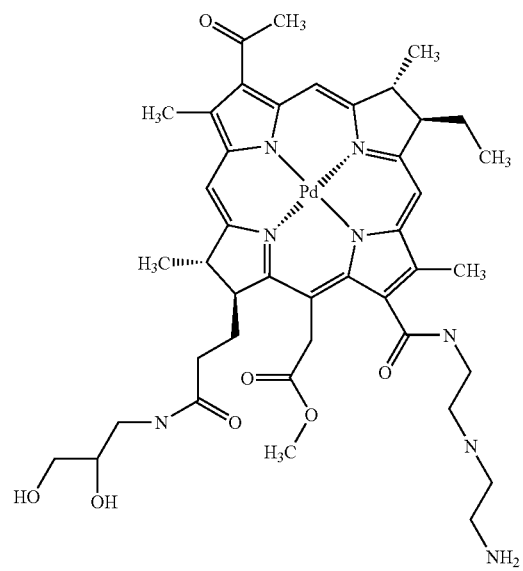 |

| Compound No. | Compound Name | Chemical Structure |
|---|---|---|
| 56 | Palladium $3^1$-oxo-15-methoxycarbonylmethyl-Rhodobacteriochlorin-$13^1$-(2,3-dihydroxypropyl)amide-$17^3$-(2-N-(2'-pyridyl)aminoethyl)amide | 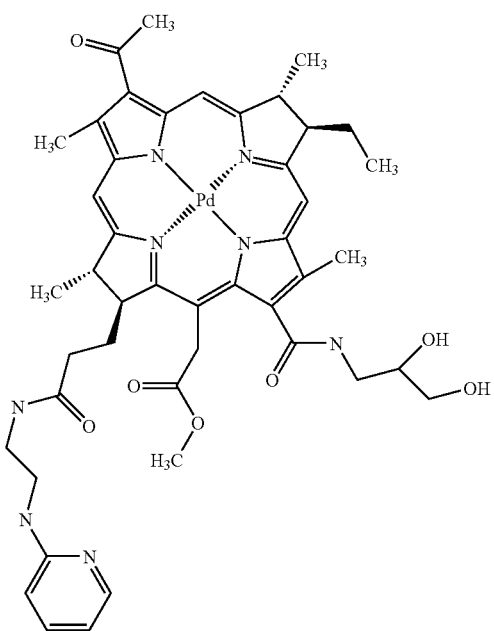 |
| 57 | Palladium $3^1$-oxo-15-methoxycarbonylmethyl-Rhodobacteriochlorin-$13^1$-(2-N-(2'-pyridyl)aminoethyl)amide-$17^3$-(2,3-dihydroxypropyl)amide | 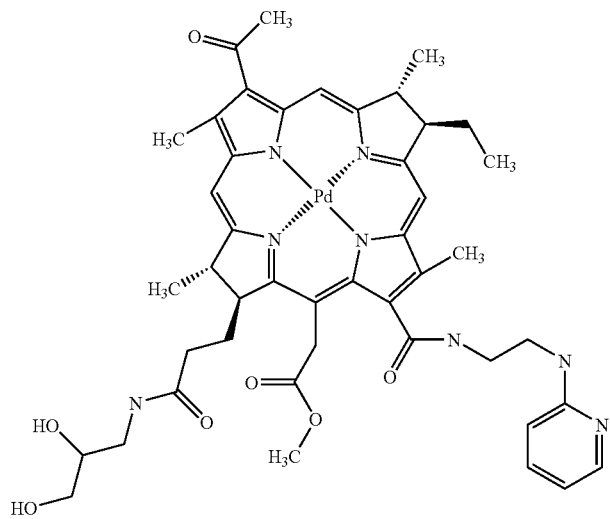 |

| Compound No. | Compound Name | Chemical Structure |
|---|---|---|
| 58 | Palladium $3^1$-oxo-15-methoxycarbonylmethyl-Rhodobacteriochlorin-$13^1$-(2,3-dihydroxypropyl)amide-$17^3$-([2-bis(2-aminoethyl)amino]ethyl)amide | 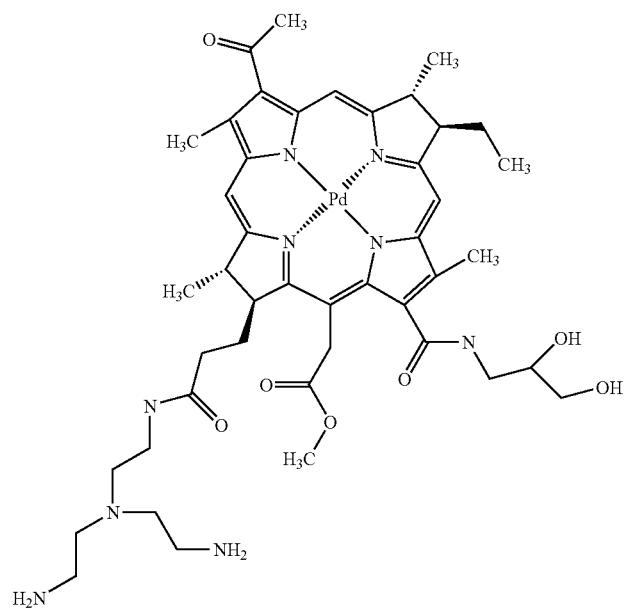 |
| 59 | Palladium $3^1$-oxo-15-methoxycarbonylmethyl-Rhodobacteriochlorin-$13^1$-([2-bis(2-aminoethyl)amine]ethyl)amide-$17^3$-(2,3-dihydroxypropyl)amide | 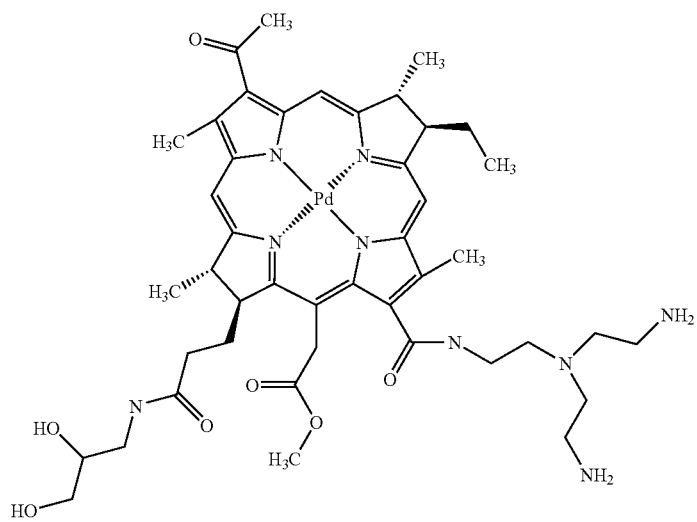 |

-continued

| Compound No. | Compound Name | Chemical Structure |
|---|---|---|
| 60 | Palladium $3^1$-oxo-15-methoxycarbonylmethyl-Rhodobacteriochlorin-$13^1$-(3-aminopropyl)amide-$17^3$-(2,3-dihydroxypropyl)amide | 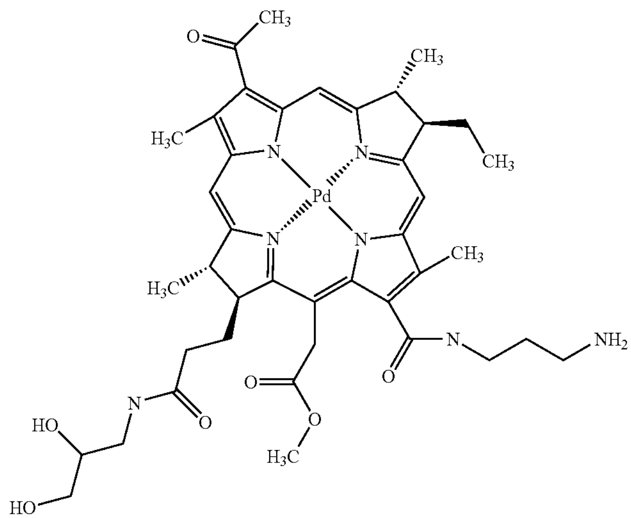 |
| 61 | Palladium $3^1$-oxo-15-methoxycarbonylmethyl-Rhodobacteriochlorin-$13^1$-(4-aminobutyl)amide-$17^3$-(2,3-dihydroxypropyl)amide | 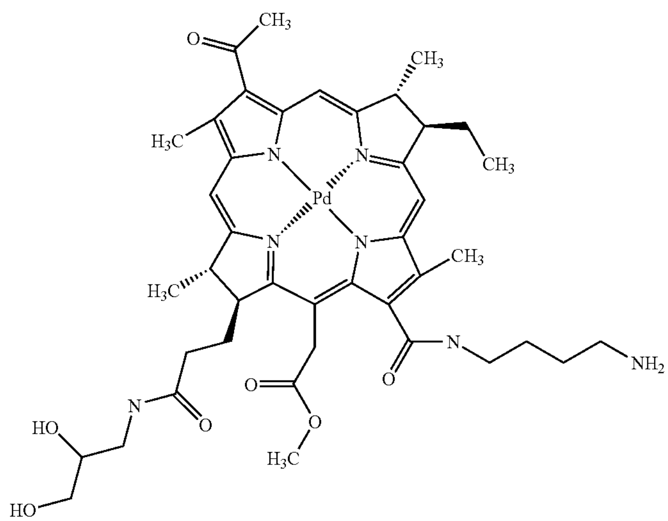 |
| 62 | Palladium $3^1$-oxo-15-methoxycarbonylmethyl-Rhodobacteriochlorin-$13^1$-(2-$N^2$-diethylaminoethyl)amide-$17^3$-(2,3-dihydroxy propyl)amide | 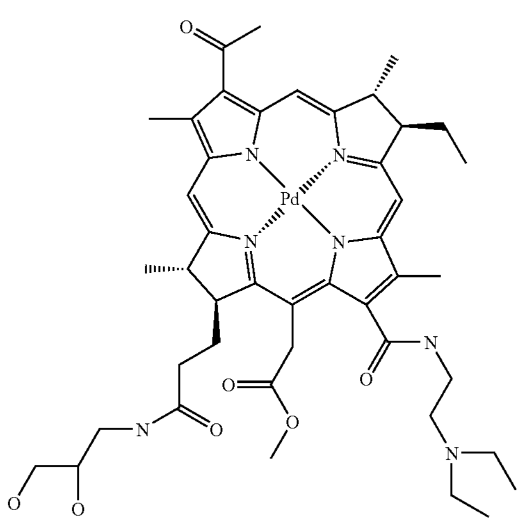 |

| Compound No. | Compound Name | Chemical Structure |
|---|---|---|
| 63 | Palladium $3^1$-oxo-15-methoxycarbonylmethyl-Rhodobacteriochlorin-$13^1$-(2-N-ethylaminoethyl)amide-$17^3$-(2,3-dihydroxy propyl)amide | 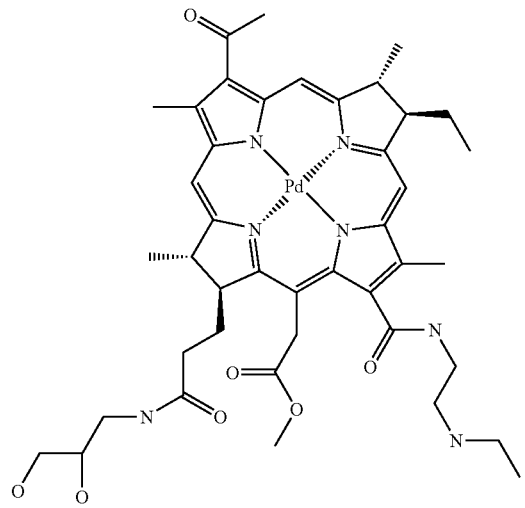 |
| 64 | Palladium $3^1$-oxo-15-methoxycarbonylmethyl-Rhodobacteriochlorin-$13^1$-(3-N-methylaminopropyl)amide-$17^3$-(2,3-dihydroxypropyl)amide | 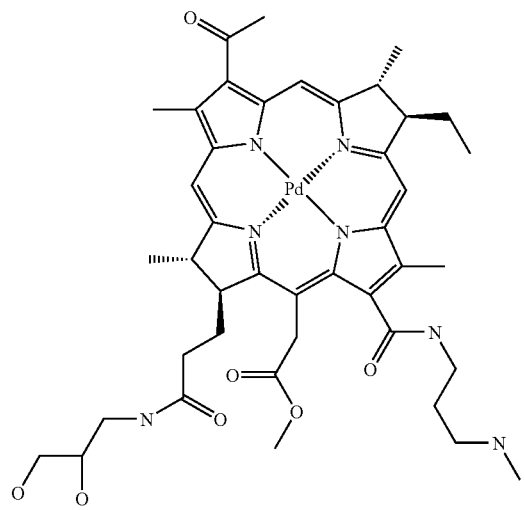 |
| 65 | Palladium $3^1$-oxo-15-methoxycarbonylmethyl-Rhodobacteriochlorin-$13^1$-(2-$N^2$-dimethylaminoethyl)amide-$17^3$-(2-hydroxy ethyl)amide | 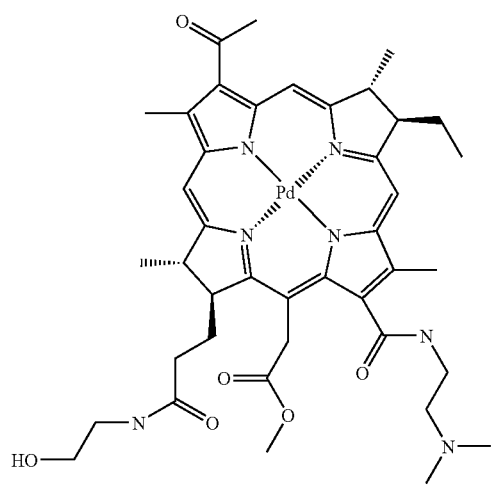 |

| Compound No. | Compound Name | Chemical Structure |
|---|---|---|
| 66 | Palladium $3^1$-oxo-15-methoxycarbonylmethyl-Rhodobacteriochlorin-$13^1$-(2-$N^2$-dimethylaminoethyl)amide-$17^3$-(3-hydroxy propyl)amide | 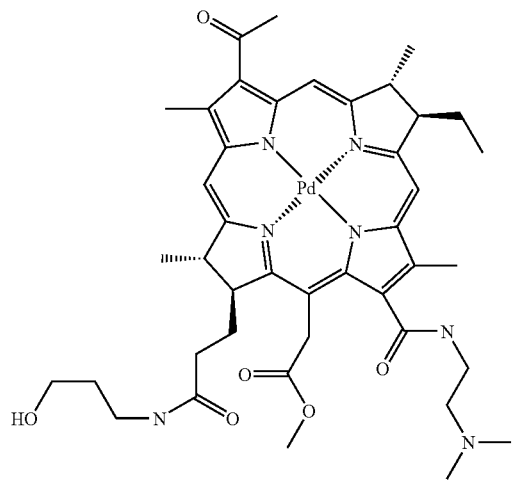 |
| 67 | Palladium $3^1$-oxo-15-methoxycarbonylmethyl-Rhodobacteriochlorin-$13^1$-(2-$N^2$-dimethylaminoethyl)amide-$17^3$-(2-hydroxy propyl)amide | 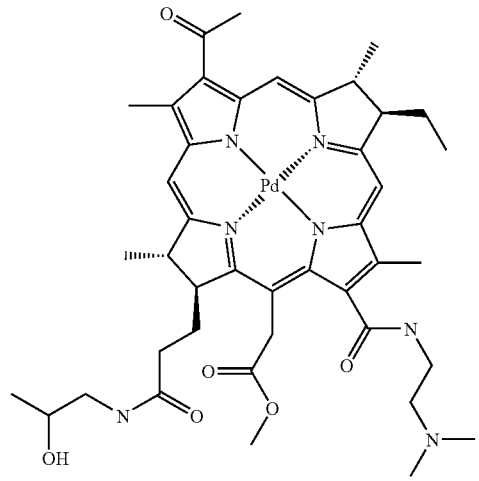 |
| 68 | Palladium $3^1$-oxo-15-methoxycarbonylmethyl-Rhodobacteriochlorin-$13^1$-(2-$N^2$-dimethylaminoethyl)amide-$17^3$-((R)-2-hydroxypropyl)amide | 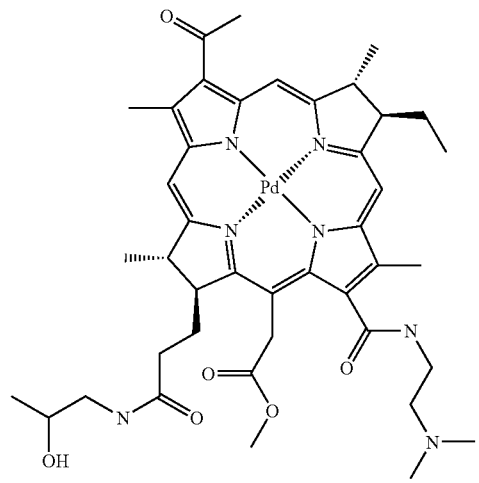 |

-continued

| Compound No. | Compound Name | Chemical Structure |
|---|---|---|
| 69 | Palladium $3^1$-oxo-15-methoxycarbonylmethyl-Rhodobacteriochlorin-$13^1$-(2-$N^2$-dimethylaminoethyl)amide-$17^3$-((S)-2-hydroxypropyl)amide | 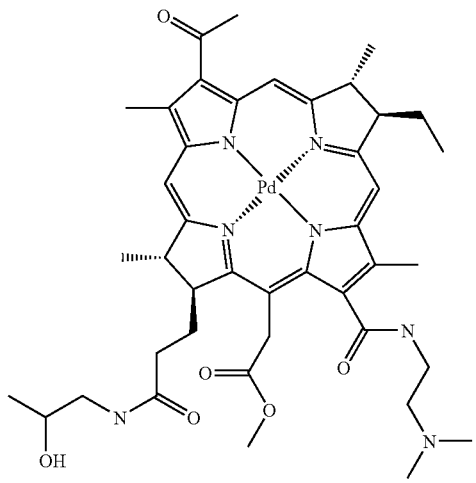 |
| 70 | Palladium $3^1$-oxo-15-methoxycarbonylmethyl-Rhodobacteriochlorin-$13^1$-(2-$N^2$-dimethylaminoethyl)amide-$17^3$-(2-(2-hydroxyethylamino)ethyl)amide | 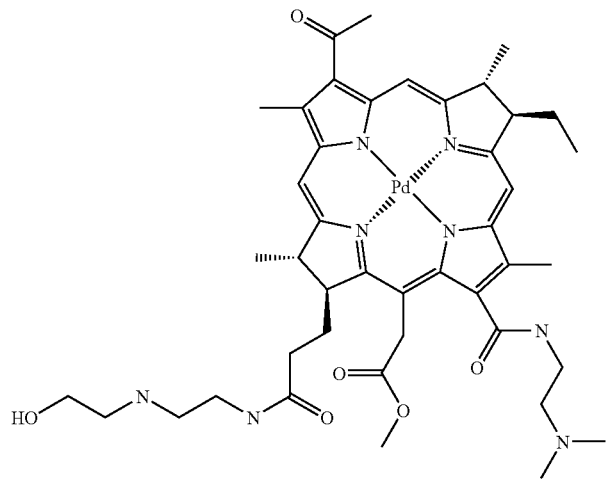 |
| 71 | Palladium $3^1$-oxo-15-methoxycarbonylmethyl-Rhodobacteriochlorin-$13^1$-(3-N-(2'-pyridyl)aminopropyl)amide-$17^3$-(2,3-dihydroxypropyl)amide | 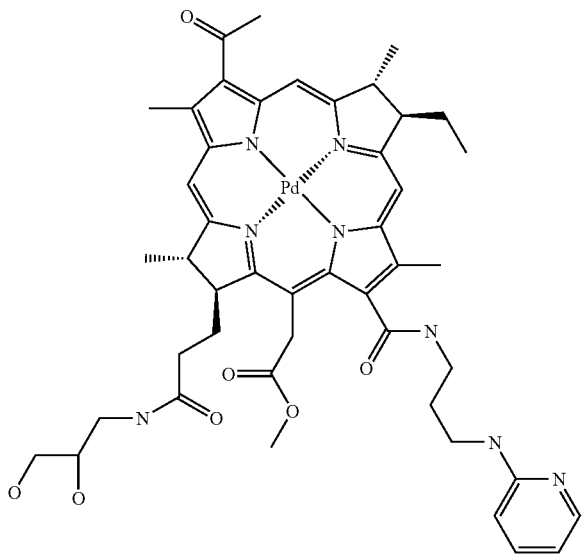 |

| Compound No. | Compound Name | Chemical Structure |
|---|---|---|
| 72 | Palladium $3^1$-oxo-15-methoxycarbonylmethyl-Rhodobacteriochlorin-$13^1$-(4-N-(2'-pyridyl)aminobutyl)amide-$17^3$-(2,3-dihydroxypropyl)amide | 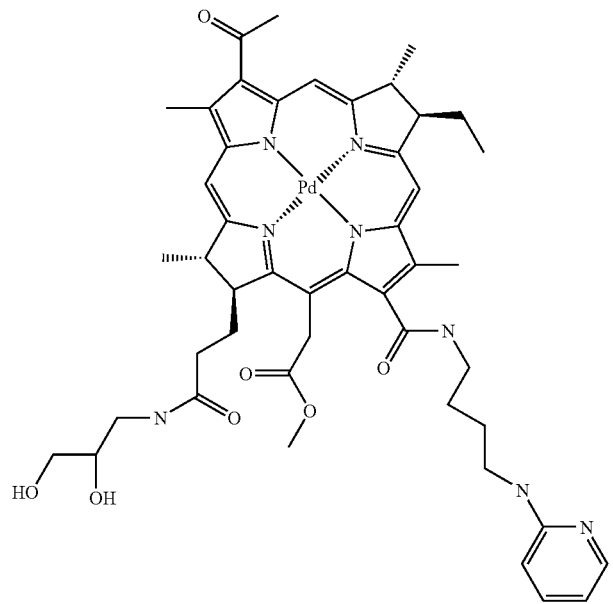 |
| 73 | Palladium $3^1$-oxo-15-methoxycarbonylmethyl-Rhodobacteriochlorin-$13^1$-(2,3-dihydroxypropyl)amide-$17^3$-(3-N-(2'-pyridyl)aminopropyl)amide | 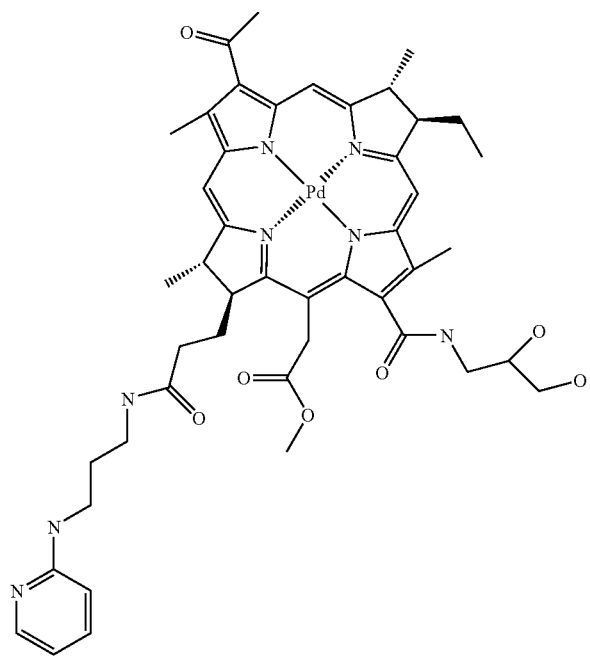 |

| Compound No. | Compound Name | Chemical Structure |
|---|---|---|
| 74 | Palladium $3^1$-oxo-15-methoxycarbonylmethyl-Rhodobacteriochlorin-$13^1$-(2,3-dihydroxypropyl)amide-$17^3$-(4-N-(2'-pyridyl)aminobutyl)amide | 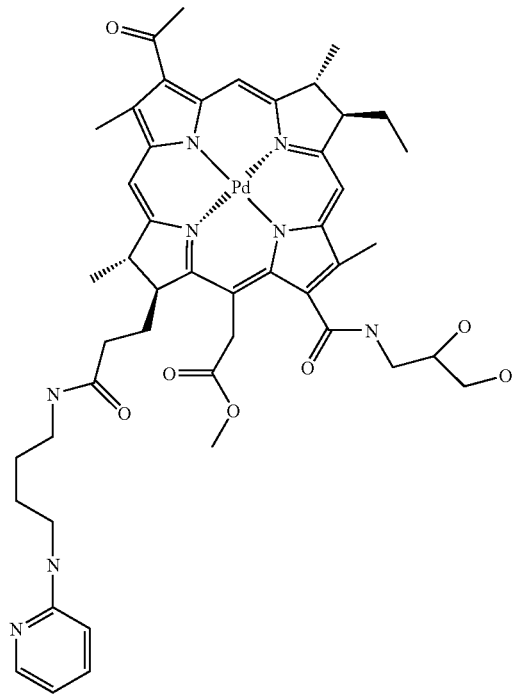 |
| 75 | Palladium $3^1$-oxo-15-methoxycarbonylmethyl-Rhodobacteriochlorin-$13^1$-(2-$N^2$-dimethylaminoethyl)amide-$17^3$-(glycosyl) amide | 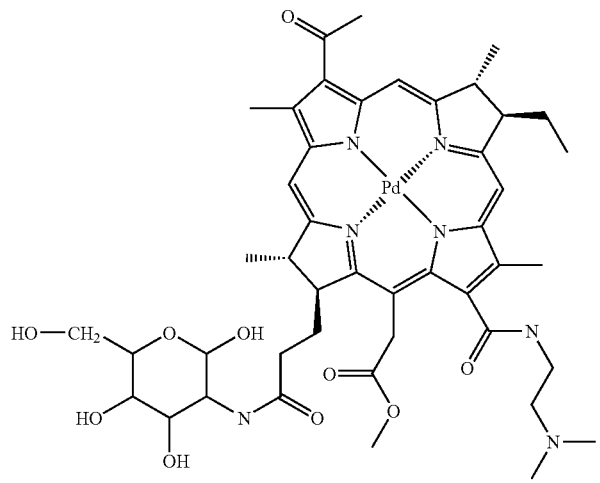 |

REFERENCES

Borle, F, Radu A, Monnier P, van den Bergh H, Wagnieres, G. (2003). Evaluation of the photosensitizer tookad for photodynamic therapy on the syrian golden hamster cheek pouch model: Light dose, drug dose and drug-light interval effects. *Photochem Photobiol*, 78(4): 377-383.

Campbell R B, Fukumura D, Brown E B, Mazzola L M, Izumi Y, Jain R K, Torchilin V P, Munn L L. (2002). Cationic charge determines the distribution of liposomes between the vascular and extravascular compartments of tumors. *Cancer Res* 62(23): 6831-6836.

Chen, Q, Huang, Z, Luck, D, Beckers, J, Brun, P H, Wilson, B C, Scherz, A, Salomon, Y, and Hetzel, F W. (2002) Preclinical studies in normal canine prostate of a novel palladium-bacteriopheophorbide (WST09) photosensitizer for photodynamic therapy of prostate cancers. *Photochem Photobiol*, 76: 438-445.

Dellian M, Yuan F, Trubetskoy V S, Torchilin V P, Jain R K. (2000). Vascular permeability in a human tumor xenografts; molecular charge dependence. *Br J Cancer* 82:1513-1518.

Dougherty, T. J. and J. G. Levy (2003). Photodynamic therapy (PDT) and clinical applications. *Biomedical Photonics Handbook*. V. Tuan. Boca Raton, CRC Press LLC. 38: 1-38.

Elhilali, M. (2004). Results of a phase I/II trial of WST09-mediated photodynamic therapy (WST09-PDT) for recurrent localized prostate cancer following failed external beam radiation therapy (EBRT). XIXth EAU CONGRESS, Workshop 1 "Vascular targeted photodynamic therapy for the treatment of prostate cancer: first clinical results with palladium bacteriopheophorbide (WST09)", VIENNA.

Ghinea, N. and N. Simionescu (1985). Anionized and cationized hemeundecapeptides as probes for cell-surface charge and permeability studies differentiated labeling of endothelial plasmalemmal vesicles. *J Cell Biol* 100(2): 606-612.

Gleave M E, Hsieh J T, Wu H C, von Eschenbach A C, Chung L W. (1992). Serum prostate specific antigen levels in mice bearing human prostate LNCaP tumors are determined by tumor volume and endocrine and growth factors. *Cancer Res.* 52:1598-1605.

Gross, S., Gilead, A., Scherz, A., Neeman, M., and Salomon, Y. (2003) Monitoring photodynamic therapy of solid tumors online by BOLD-contrast MRI. *Nat Med,* 9:1327-1331.

Hamblin M R, Rajadhyaksha M, Momma T, Soukos N S, Hasan T. (1999). In vivo fluorescence imaging of the transport of charged chlorin e6 conjugates in a rat orthotopic prostate tumour. *BP J Cancer* 81(2): 261-268.

Hashizime H, Baluk P, Morikawa S, McLean J W, Thurston G, Roberge S, Jain R K, McDonald D M. (2000). Openings between defective endothelial cells explain tumor vessel leakiness. *Am J Pathol* 156(4): 1363-1380.

Kelleher, D K, Thews, O, Scherz, A, Salomon, Y, and Vaupel, P. (2003) Combined hyperthermia and chlorophyll-based photodynamic therapy: tumour growth and metabolic microenvironment. *Br J Cancer,* 89: 2333-2339.

Kinoshita, I, Kashiwabara, K, Fujita, J, Matsumoto, K, and Ooi, S. (1981). Preparation, resolution, and adsorption and circular dichroism spectra of $[Co(en)_n\{NH_2CH_2CH_2P(CH_3)_2\}_{3-n}]^{3+}$ and the related complexes, and the absolute configuration of $(+)_{589}$-fac-$[Co\{NH_2CH_2CH_2P(CH_3)_2\}_3]^{3+}$ determined by X-Ray analysis." *Bull. Chem. Soc. Jpn.* 54:2683-2690.

Koudinova, N. V., Pinthus, J. H., Brandis, A., Brermer, O., Bendel, P., Ramon, J., Eshhar, Z., Scherz, A., and Salomon, Y. (2003) Photodynamic therapy with Pd-bacteriopheophorbide (TOOKAD): Successful in vivo treatment of human prostatic small cell carcinoma xenografts. *Int J Cancer,* 104: 782-789.

Krammer B. (2001) Vascular effects of photodynamic therapy *Anticancer Res.* 21(6B):4271-7

Mazor, O, Kostenich, G, Brandis, A, Orenstein, A, Salomon, Y, and Scherz, A. (2003) Selective tumor vascular destruction of colon carcinoma xenografts by the hydrophilic Pd-bacteriochlorophyll derivative, WST11 *9th International Photodynamic Association, May* 20-23*, Miyazaki, Japan,* Book of Abstracts, p. 19.

Plaks, V, Koudinova, N, Nevo, U, Pinthus, J H, Kanety, H, Eshhar, Z, Ramon, J, Scherz, A, Neeman, M, and Salomon, Y. (2004) Photodynamic Therapy of Established Prostatic Adenocarcinoma with TOOKAD: A Biphasic Apparent Diffusion Coefficient Change as Potential Early MRI Response Marker. *Neoplasia, In press.*

Preise D, Mazor O, Koudinova N, Liscovitch M, Scherz A, Salomon Y. (2003). Bypass of tumor drug resistance by antivascular therapy. *Neoplasia* 5(6): 475-480.

Ran S, Downes A, Thorpe P E. (2002). Increased exposure of anionic phospholipids on the surface of tumor blood vessels. *Cancer Res* 62:6132-6140.

Rosenbach-Belkin V, Chen L, Fiedor L, Tregub I, Paviotsky F, Brumfeld V, Salomon Y, Scherz A. (1996). Serine conjugates of chlorophyll and bacteriochlorophyll: photocytotoxicity in vitro and tissue distribution in mice bearing melanoma tumors. *Photochem Photobiol* 64:174-181.

Schreiber, S., Gross, S., Brandis, A., Harmelin, A., Rosenbach-Belkin, V., Scherz, A., and Salomon, Y. (2002) Local photodynamic therapy (PDT) of rat C6 glioma xenografts with Pd-bacteriopheophorbide leads to decreased metastases and increase of animal cure compared with surgery. *Int J Cancer,* 99: 279-285.

Segev A, Aviezer D, Safran M, Gross Z, Yayon A. (2002). Inhibition of vascular smooth muscle cell proliferation by a novel fibroblast growth factor receptor antagonist. *Cardiovasc Res* 53(1): 232-241.

Simionescu, N, Simionescu M, Palade G E. (1981). Differentiated microdomains on the luminal surface of the capillary endothelium. I. Preferential distribution of anionic sites. *J Cell Biol* 90(3): 605-613.

Suzuki, T., Rude, M., Simonsen, K. P., Morooka, M., Tanaka, H., Ohba, S., Galsbol, F., and Fujita, J. (1994). Preparation and characterization of Iridium(III) complexes containing (2-aminoethyl)dimethylphosphine (edmp). Structures of fac-$[Ir(edmp)_3]Cl_3.5H_2O$ and trans(Cl, Cl), cis(P,P)-$[IrCl_2(edpp)_2]BF_4$ and comparisons of their properties with those of the Cobalt(III) and Rhodium(III) analogs." *Bull. Chem. Soc. Jpn.* 67:1013-1023.

Thurston G, McLean J W, Rizen M, Baluk P, Haskell A, Murphy T J, Hanahan D, McDonald D M. (1998). Cationic liposomes target angiogenic endothelial cells in tumors and chronic inflammation in mice. *J Clin Invest* 101: 1401-1413.

Trachtenberg, J. (2003). Initial Phase I/II Trial of WST09-PDT Photodynamic Therapy Following Failed External Beam for Prostate Cancer. CapCure Retreat, Washington D.C.

Tuan, V. et al. (2002). Pharmaceutical strategies utilizing recombinant human serum albumin. *Pharm Res* 19: 569-577.

Wasielewski M. R. and Svec, W. A. (1980). "Synthesis of Covalently Linked Dimeric Derivatives of Chlorophyll a, Pyrochlorophyll a, Chlorophyll b, and Bacteriochlorophyll a." *J. Org. Chem.* 45: 1969-1974.

Zilberstein J, Bromberg A, Frantz A, Rosenbach-Belkin V, Kritzmann A, Pfefermann R, Salomon Y, Scherz A. (1997). Light-dependent oxygen consumption in bacteriochlorophyll-serine-treated melanoma tumors: on-line determination using a tissue inserted oxygen microsensor. *Photochem Photobiol* 65(6). 1012-1019.

Zilberstein J, Schreiber S, Bloemers M C, Bendel P, Neeman M, Schechtman E, Kohen F, Scherz A, Salomon Y. (2001). Antivascular treatment of solid melanoma tumors with bacteriochlorophyll-serine-based photodynamic therapy. *Photochem Photobiol* 73(3): 257-266.

The invention claimed is:

1. A bacteriochlorophyll compound containing at least one of the following groups: (i) a positively charged group; or (ii) a basic group that is converted to a positively charged group under physiological conditions, or both, wherein said bacteriochlorophyll compound is of the formula II:

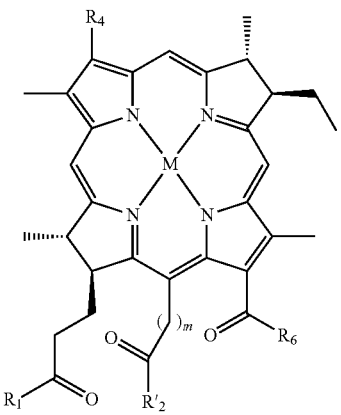

(II)

wherein

M represents 2H, a divalent metal atom selected from the group consisting of Pd, Pt, Co, Sn, Ni, Cu, Zn and Mn, or a trivalent metal atom selected from the group consisting of Fe, Mn, Co, Au, Al, Gd, Er, Yb and Cr;

$R_1$, $R'_2$ and $R_6$ each independently is Y—$R_8$, —$NR_9R'_9$, or —$N^+R_9R'_9R''_9A^-$;

Y is O or S;

$R_4$ is —CH=$CR_9R'_9$, —CH=$CR_9$Hal, —CH=CH—$CH_2$—$NR_9R'_9$, —CH=CH—$CH_2$—$N^+R_9R'_9R''_9A^-$, —CHO, —CH=$NR_9$, —CH=$N^+R_9R'_9A^-$, —$CH_2$—$R_9$, —$CH_2$—$SR_9$, —$CH_2$—Hal, —$CH_2$—$R_9$, —$CH_2$—$NR_9R'_9$, —$CH_2$—$N^+R_9R'_9R''_9A^-$, —$CH_2$—$CH_2R_9$, —$CH_2$—$CH_2$Hal, —$CH_2$—$CH_2OR_9$, —$CH_2$—$CH_2SR_9$, —$CH_2$—$CH_2$—$NR_9R'_9$, —$CH_2$—$CH_2$—$N^+R_9R'_9R''_9A^-$, —$COCH_3$, $C(CH_3)$=$CR_9R'_9$, —$C(CH_3)$=$CR_9$Hal, —$C(CH_3)$=$NR_9$, —$CH(CH_3)$=$N^+R_9R'_9A^-$, —$CH(CH_3)$—Hal, —$CH(CH_3)$—$OR_9$, —$CH(CH_3)$—$SR_9$, —$CH(CH_3)$—$NR_9R'_9$, —$CH(CH_3)$—$N^+R_9R'_9R''_9A^-$, or —C≡$CR_9$;

$R_8$, $R_9$, $R'_9$ and $R''_9$ each independently is:

(a) H;
(b) hydrocarbyl;
(c) hydrocarbyl substituted by one or more groups selected from the group consisting of halogen, nitro, oxo, OR, SR, epoxy, epithio, aziridine, —CONRR', —COR, COOR, COSR, —$OSO_3R$, —$SO_3R$, —$SO_2R$, —$NHSO_2R$, —$SO_2NRR'$, —NRR', =N—OR, =N—NRR', —C(=NR)—NR'R", —(R)N—C(=NR)—NR'R", —NR—NR'R", O←NR—, >C=NR, —$(CH_2)_n$—NR—COR', —$(CH_2)_n$—CO—NRR', —O—$(CH_2)_n$—OR, —O—$(CH_2)_n$—O—$(CH_2)_n$—R, —$OPO_3RR'$, —$PO_2HR$, and —$PO_3RR'$, wherein n is an integer from 1 to 6, R and R' each independently is H, hydrocarbyl or heterocyclyl and R" is hydrocarbyl or heterocyclyl or two of R, R' and R" together with the N atom to which they are attached form a 3-7 membered saturated ring, optionally containing one or more heteroatoms selected from the group consisting of O, S and N and optionally further substituted at the additional N atom by alkyl optionally substituted by halogen, hydroxyl or amino;
(d) $C_1$-$C_{25}$ hydrocarbyl substituted by one or more groups selected from the group consisting of positively charged groups selected from: (i) an onium group; (ii) a cation derived from a N-containing group; or (iii) a cation derived from a heteroaromatic compound containing one or more N atoms and optionally O or S atoms; negatively charged groups selected from the group consisting of $COO^-$, $COS^-$, —$OSO_3^-$, —$SO_3^-$, —$OPO_3R^-$, —$PO_2H^-$, -$PO_3H_2$— and —$PO_3R^-$; basic groups that are converted to positively charged groups under physiological conditions, selected from the group consisting of —NRR', —C(=NR)—NR'R", —PRR', —NR—NR'R", —(R)N—C(=NR)—NR'R", O←NR—, >C=NR and a N-containing heteroaromatic radical, wherein R, R' and R" are as defined in (c) above; and acidic groups that are converted to negatively charged groups under physiological conditions selected from the group consisting of —COOH, —COSH, —$SO_3H$ and —$PO_3H_2$;
(e) $C_1$-$C_{25}$ hydrocarbyl containing one or more heteroatoms and/or one or more carbocyclic or heterocyclic moieties;
(f) $C_1$-$C_{25}$ hydrocarbyl containing one or more heteroatoms and/or one or more carbocyclic or heterocyclic moieties and substituted by one or more groups as defined in (c) and (d) above;
(g) $C_1$-$C_{25}$ hydrocarbyl substituted by a residue of an amino acid, a peptide, a protein, a monosaccharide, an oligosaccharide, or a polysaccharide; or
(h) a residue of an amino acid, a peptide, a protein, a monosaccharide, an oligosaccharide, or a polysaccharide;

$R_8$ may further be $H^+$ or a cation $R^+_{10}$, when $R_1$, $R'_2$ and $R_6$ each independently is Y—$R_8$;

$R^+_{10}$ is a metal, ammonium or an organic cation;

$A^-$ is a physiologically acceptable anion;

m is 0 or 1; and pharmaceutically acceptable salts and optical isomers thereof.

2. The bacteriochlorophyll compound according to claim 1, wherein M is 2H.

3. The bacteriochlorophyll compound according to claim 1, wherein M is Pd.

4. The bacteriochlorophyll compound according to claim 1, containing at least one positively charged group.

5. The bacteriochlorophyll compound according to claim 4, wherein said at least one positively charged group is a cation derived from a N-containing group.

6. The bacteriochlorophyll compound according to claim 5, wherein said cation derived from a N-containing group is selected from the group consisting of —$N^+(RR'R")$, —(R)N—$N^+(RR'R")$, O←$N^+(RR')$—, >C=$N^+(RR')$, —C(=RN)—$N^+RR'R"$ and —(R)N—C(=NR)—$N^+RR'R"$ group, wherein R, R' and R" each independently is H, hydrocarbyl, or heterocyclyl, or two of R, R' and R" together with the N atom to which they are attached form a 3-7 membered saturated ring, optionally containing one or more heteroatoms selected from the group consisting of O, S and N, and optionally further substituted at the additional N atom.

7. The bacteriochlorophyll compound according to claim 6, wherein said cation is an end group or a group located within a hydrocarbyl chain of the bacteriochlorophyll molecule.

8. The bacteriochlorophyll compound according to claim 6, wherein said cation is an ammonium group of the formula —$N^+(RR'R")$, wherein each of R, R' and R" independently is H, hydrocarbyl, or heterocyclyl, or two of R, R' and R" together with the N atom form a 3-7 membered saturated ring, optionally containing an O, S or N atom and optionally further substituted at the additional N atom.

9. The bacteriochlorophyll compound according to claim 8, wherein said 3-7 membered saturated ring is selected from the group consisting of aziridine, pyrrolidine, piperidine, morpholine, thiomorpholine, azepine and piperazine optionally substituted at the additional N atom by $C_1$-$C_6$ alkyl optionally substituted by halo, hydroxyl or amino.

10. The bacteriochlorophyll compound according to claim 4, wherein said at least one positively charged group is a cation derived from a heteroaromatic compound containing one or more N atoms and optionally O or S atoms.

11. The bacteriochlorophyll compound according to claim 10, wherein said cation is selected from the group consisting of pyrazolium, imidazolium, oxazolium, thiazolium, pyridinium, quinolinium, isoquinolinium, pyrimidinium, 1,2,4-triazinium, 1,3,5-triazinium and purinium.

12. The bacteriochlorophyll compound according to claim 4, wherein said at least one positively charged group is an onium group selected from the group consisting of —O(RR'), —S$^+$(RR'), —Se$^+$(RR'), —Te$^+$(RR'), —P$^+$(RR'R"), —As$^+$(RR'R"), —Sb$^+$(RR'R"), and —Bi$^+$(RR'R"), wherein R, R' and R" each independently is H, hydrocarbyl, or heterocyclyl.

13. The bacteriochlorophyll compound according to claim 1, containing at least one basic group that is converted to a positively charged group under physiological conditions.

14. The bacteriochlorophyll compound according to claim 1, wherein said N-containing heteroaromatic radical is pyrazolyl, imidazolyl, oxazolyl, thiazolyl, pyridyl, quinolinyl, isoquinolinyl, pyrimidyl, 1,2,4-triazinyl, 1,3,5-triazinyl or purinyl.

15. The bacteriochlorophyll compound according to claim 1, wherein:
M is 2H or Pd;
$R'_2$ is —$OR_8$ wherein $R_8$ is $C_1$-$C_6$ alkyl;
$R_4$ is —$COCH_3$;
$R_2$ is OH, —$NR_9R'_9$, or —$NR_9$—$CH_2$—$CH(OH)$—$CH_2OH$;
$R_6$ is —$NR_9R'_9$ or —$NR_9$—$CH_2$—$CH(OH)$—$CH_2OH$;
$R_9$ is H or $C_2$-$C_6$ alkyl; and
$R'_9$ is $C_1$-$C_{25}$ hydrocarbyl substituted by at least one positively charged group or at least one basic group that is converted to a positively charged group under physiological conditions, or both.

16. The bacteriochlorophyll compound according to claim 15, wherein $R_9$ is H and $R'_9$ is $C_1$-$C_{25}$ alkyl substituted by at least one positively charged group —N$^+$RR'R" or by at least one basic group —NRR' and optionally interrupted by a —N(R")— group, wherein R and R' each independently is H, $C_1$-$C_6$ alkyl optionally substituted by NR"R", or heterocyclyl such as pyridyl, or R and R' together with the N atom form a 6-membered ring further containing an O, S or N atom, and R" is H or $C_2$-$C_6$ alkyl.

17. The bacteriochlorophyll compound according to claim 15, wherein $R_1$ is OH and $R_6$ is a —$NHR'_9$ group selected from the group consisting of:

(i)

—NH—$(CH_2)_n$—NRR'  or  —NH—$(CH_2)_n$—N$^+$RR'R";

(ii)

—NH—$(CH_2)_n$—N(R")—$(CH_2)_n$—NRR';

(iii)

—NH—$(CH_2)_n$—N$\begin{smallmatrix}(CH_2)_n—NH_2 \\ (CH_2)_n—NH_2\end{smallmatrix}$;

-continued (iv)

—NH—$(CH_2)_n$—N⌒X; and (v)

—NH—$(CH_2)_m$—NH—pyridyl, wherein
X is O, S or NR;
R, R' and R" each independently is H or $C_1$-$C_6$ alkyl;
n is an integer from 1 to 10; and
m is an integer from 1 to 6.

18. The bacteriochlorophyll compound according to claim 17, selected from the group consisting of the compounds:

Palladium 3$^1$-oxo-15-methoxycarbonylmethyl-Rhodobacteriochlorin-13$^1$-(2-N$^3$-trimethylammoniumethyl) amide chloride salt, Palladium 3$^1$-oxo-15-methoxycarbonylmethyl-Rhodobacteriochlorin-13$^1$-(2-N$^3$-(trimethylammoniumethyl) amide acetate salt, Palladium 3$^1$-oxo-15-methoxycarbonylmethyl-Rhodobacteriochlorin-13$^1$-(2-N$^2$-dimethylaminoethyl)amide, Palladium 3$^1$-oxo-15-methoxycarbonylmethyl-Rhodobacteriochlorin-13$^1$-(3-N$^2$-dimethylaminopropyl) amide, Palladium 3$^1$-oxo-15-methoxycarbonylmethyl-Rhodobacteriochlorin-13$^1$-(2-[(2-aminoethyl)amino]ethyl) amide, Palladium 3$^1$-oxo-15-methoxycarbonylmethyl-Rhodobacteriochlorin-13$^1$-([2-bis(2-aminoethyl)amino]ethyl) amide, Palladium 3$^1$-oxo-15-methoxycarbonylmethyl-Rhodobacteriochlorin-13$^1$-(2-morpholino-N-ethyl)amide, Palladium 3$^1$-oxo-15-methoxycarbonylmethyl-Rhodobacteriochlorin-13$^1$-(2-piperazino-N-ethyl)amide, Palladium 3$^1$-oxo-15-methoxycarbonylmethyl-Rhodobacteriochlorin-13$^1$-(2-[(2-N$^2$-diethylaminoethyl) amino]ethyl)amide, and Palladium 3$^1$-oxo-15-methoxycarbonylmethyl-Rhodobacteriochlorin-13$^1$-(3-[(3-aminopropyl)amino]propyl) amide.

19. The bacteriochlorophyll compound according to claim 15, wherein $R_1$ and $R_6$ are both the same —$NHR'_9$ group selected from the group consisting of:

(i)

—NH—$(CH_2)_n$—NRR'  or  —NH—$(CH_2)_n$—N$^+$RR'R";

(ii)

—NH—$(CH_2)_n$—N(R")—$(CH_2)_n$—NRR';

(iii)

—NH—$(CH_2)_n$—N$\begin{smallmatrix}(CH_2)_n—NH_2 \\ (CH_2)_n—NH_2\end{smallmatrix}$ (iv)

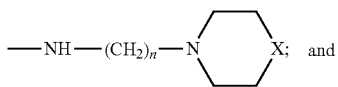 and (v)

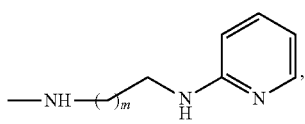

wherein
X is O, S or NR;
R, R' and R" each independently is H or $C_1$-$C_6$ alkyl;
n is an integer from 1 to 10; and
m is an integer from 1 to 6.

20. The bacteriochlorophyll compound according to claim 19, selected from the group consisting of the compounds:

$3^1$-oxo-15-methoxycarbonylmethyl-Rhodobacteriochlorin-$13^1$,$17^3$-di(2-aminoethyl)amide, $3^1$-oxo-15-methoxycarbonylmethyl-Rhodobacteriochlorin-$13^1$,$17^3$-di(2-N-trimethylammoniumethyl)amide dicitrate salt, $3^1$-oxo-15-methoxycarbonylmethyl-Rhodobacteriochlorin-$13^1$,$17^3$-di(3-aminopropyl)amide, $3^1$-oxo-15-methoxycarbonylmethyl-Rhodobacteriochlorin-$13^1$,$17^3$-di(3-N-trimethylammoniumpropyl)amide dicitrate salt, $3^1$-oxo-15-methoxycarbonylmethyl-Rhodobacteriochlorin-$13^1$,$17^3$-di(6-aminohexyl)amide, $3^1$-oxo-15-methoxycarbonylmethyl-Rhodobacteriochlorin-$13^1$,$17^3$-di(6-N-trimethylammoniumhexyl)amide dicitrate salt, Palladium $3^1$-oxo-15-methoxycarbonylmethyl-Rhodobacteriochlorin $13^1$,$17^3$-di(2-aminoethyl)amide, Palladium $3^1$-oxo-15-methoxycarbonylmethyl-Rhodobacteriochlorin $13^1$,$17^3$-di(2-$N^3$-trimethylammoniumethyl)amide diphosphate salt, Palladium $3^1$-oxo-15-methoxycarbonylmethyl-Rhodobacteriochlorin-$13^1$,$17^3$-di(2-$N^3$-trimethylammoniumethyl)amide diacetate salt, Palladium $3^1$-oxo-15-methoxycarbonylmethyl-Rhodobacteriochlorin-$13^1$,$17^3$-di(3-aminopropyl)amide, Palladium $3^1$-oxo-15-methoxycarbonylmethyl-Rhodobacteriochlorin-$13^1$,$17^3$-di(4-aminobutyl)amide, Palladium $3^1$-oxo-15-methoxycarbonylmethyl-Rhodobacteriochlorin-$13^1$,$17^3$-di(2-$N^2$-dimethylaminoethyl)amide, Palladium $3^1$-oxo-15-methoxycarbonylmethyl-Rhodobacteriochlorin-$13^1$,$17^3$-di(3-$N^2$-dimethylaminopropyl)amide, Palladium $3^1$-oxo-15-methoxycarbonylmethyl-Rhodobacteriochlorin-$13^1$,$17^3$-di-(2-[(2-aminoethyl)amino]ethyl)amide, Palladium $3^1$-oxo-15-methoxycarbonylmethyl-Rhodobacteriochlorin-$13^1$,$17^3$-di-(2-[(2-$N^2$-diethylaminoethyl)amino]ethyl)amide, Palladium $3^1$-oxo-15-methoxycarbonylmethyl-Rhodobacteriochlorin-$13^1$,$17^3$-di(2-morpholino-N-ethyl)amide, Palladium $3^1$-oxo-15-methoxycarbonylmethyl-Rhodobacteriochlorin-$13^1$,$17^3$-di(2-piperazino-N-ethyl)amide, Palladium $3^1$-oxo-15-methoxycarbonylmethyl-Rhodobacteriochlorin-$13^1$,$17^3$-di-(3-[(3-aminopropyl)amino]propyl)amide, Palladium $3^1$-oxo-15-methoxycarbonylmethyl-Rhodobacteriochlorin-$13^1$,$17^3$-di([2-bis(2-aminoethyl)amino]ethyl)amide, Palladium $3^1$-oxo-15-methoxycarbonylmethyl-Rhodobacteriochlorin-$13^1$,$17^3$-di(2-N-(2'-pyridyl)aminoethyl)amide, and Palladium $3^1$-oxo-15-methoxycarbonylmethyl-Rhodobacteriochlorin-$13^1$,$17^3$-di(2-$N^2$-diethylaminoethyl)amide.

21. The bacteriochlorophyll compound according to claim 15, wherein $R_1$ is —NH—$CH_2$—CH(OH)—$CH_2$OH and $R_6$ is a —$NHR'_9$ group selected from the group consisting of:

(i)

—NH—$(CH_2)_n$—NRR'  or  —NH—$(CH_2)_n$—$N^+$RR'R";

(ii)

—NH—$(CH_2)_n$—N(R")—$(CH_2)_n$—NRR';

(ii)

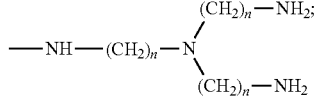

(iv)

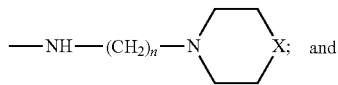 and (v)

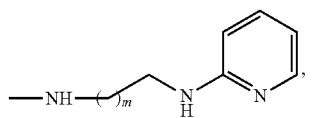

wherein
X is O, S or NR;
R, R' and R" each independently is H or $C_1$-$C_6$ alkyl;
n is an integer from 1 to 10; and
m is an integer from 1 to 6.

22. The bacteriochlorophyll compound according to claim 21, selected from the group consisting of the compounds:

Palladium $3^1$-oxo-15-methoxycarbonylmethyl-Rhodobacteriochlorin-$13^1$-(2-aminoethyl)amide-$17^3$-(2,3-dihydroxypropyl)amide, Palladium $3^1$-oxo-15-methoxycarbonylmethyl-Rhodobacteriochlorin-$13^1$-(2-$N^2$-dimethylaminoethyl)amide-$17^3$-(2,3-dihydroxypropyl)amide, Palladium $3^1$-oxo-15-methoxycarbonylmethyl-Rhodobacteriochlorin-$13^1$-(2-[(2-aminoethyl)amino]ethyl)amide-$17^3$-(2,3-dihydroxypropyl)amide, Palladium $3^1$-oxo-15-methoxycarbonylmethyl-Rhodobacteriochlorin-$13^1$-(2-N-(2'-pyridyl)aminoethyl)amide-$17^3$-(2,3-dihydroxypropyl)amide, Palladium $3^1$-oxo-15-methoxycarbonylmethyl-Rhodobacteriochlorin-$13^1$-([2-bis(2-aminoethyl)amine]ethyl)amide-$17^3$-(2,3-dihydroxypropyl)amide, Palladium $3^1$-oxo-15-methoxycarbonylmethyl-Rhodobacteriochlorin-$13^1$-(3-aminopropyl)amide-$17^3$-(2,3-dihydroxypropyl)amide, Palladium $3^1$-oxo-15-methoxycarbonylmethyl-Rhodobacteriochlorin-$13^1$-(4-aminobutyl)amide-$17^3$-(2,3-dihydroxypropyl)amide, Palladium 3¹-oxo-15-methoxycarbonylmethyl-Rhodobacteriochlorin-13¹-(2-N²-diethylaminoethyl)amide-17³-(2,3-dihydroxy propyl)amide,
Palladium 3¹-oxo-15-methoxycarbonylmethyl-Rhodobacteriochlorin-13¹-(2-N-ethylaminoethyl)amide-17³-(2,3-dihydroxy propyl)amide,
Palladium 3¹-oxo-15-methoxycarbonylmethyl-Rhodobacteriochlorin-13¹-(3-N-methylaminopropyl)amide-17³-(2,3-dihydroxypropyl)amide,
Palladium 3¹-oxo-15-methoxycarbonylmethyl-Rhodobacteriochlorin-13¹-(3-N-(2'-pyridyl)aminopropyl)amide-17³-(2,3-dihydroxypropyl)amide, and
Palladium 3¹-oxo-15-methoxycarbonylmethyl-Rhodobacteriochlorin-13¹-(4-N-(2'-pyridyl)aminobutyl)amide-17³-(2,3-dihydroxypropyl)amide.

23. The bacteriochlorophyll compound according to claim 15, wherein $R_6$ is —NH—$CH_2$—CH(OH)—$CH_2$OH and $R_1$ is a —NHR'$_9$ group selected from the group consisting of:

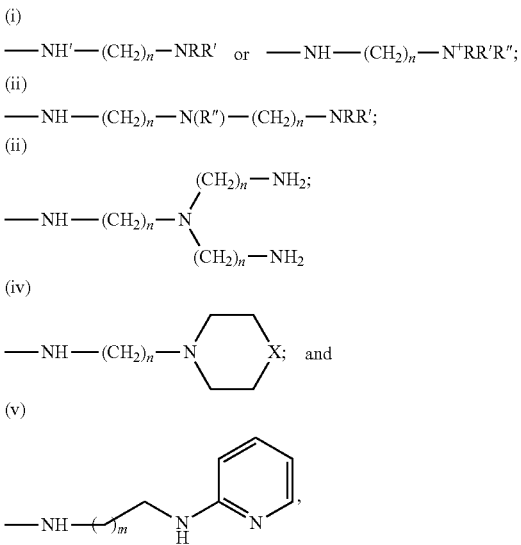

wherein
X is O, S or NR;
R, R' and R" each independently is H or $C_1$-$C_6$ alkyl;
n is an integer from 1 to 10; and
m is an integer from 1 to 6.

24. The bacteriochlorophyll compound according to claim 23, selected from the group consisting of the compounds:
Palladium 3¹-oxo-15-methoxycarbonylmethyl-Rhodobacteriochlorin-13¹-(2,3-dihydroxypropyl)amide-17³-(2-trimethylammoniumethyl)amide,
Palladium 3¹-oxo-15-methoxycarbonylmethyl-Rhodobacteriochlorin-13¹-(2,3-dihydroxypropyl)amide-17³-(2-aminoethyl)amide,
Palladium 3¹-oxo-15-methoxycarbonylmethyl-Rhodobacteriochlorin-13¹-(2,3-dihydroxypropyl)amide-17³-(2-N²-dimethyl aminoethyl)amide,
Palladium 3¹-oxo-15-methoxycarbonylmethyl-Rhodobacteriochlorin-13¹-(2,3-dihydroxypropyl)amide-17³-(2-[(2-aminoethyl)amino]ethyl)amide,
Palladium 3¹-oxo-15-methoxycarbonylmethyl-Rhodobacteriochlorin-13¹-(2,3-dihydroxypropyl)amide-17³-(2-[(2-N²-diethyl aminoethyl)amino]ethyl)amide,
Palladium 3¹-oxo-15-methoxycarbonylmethyl-Rhodobacteriochlorin-13¹-(2,3-dihydroxypropyl)amide-17³-(2-morpholino-N-ethyl)amide,
Palladium 3¹-oxo-15-methoxycarbonylmethyl-Rhodobacteriochlorin-13¹-(2,3-dihydroxypropyl)amide-17³-(2-piperazino-N-ethyl)amide,
Palladium 3¹-oxo-15-methoxycarbonylmethyl-Rhodobacteriochlorin-13¹-(2,3-dihydroxypropyl)amide-17³-(2-N-(2'-pyridyl)aminoethyl)amide,
Palladium 3¹-oxo-15-methoxycarbonylmethyl-Rhodobacteriochlorin-13¹-(2,3-dihydroxypropyl)amide-17³-([2-bis(2-aminoethyl)amino]ethyl)amide,
Palladium 3¹-oxo-15-methoxycarbonylmethyl-Rhodobacteriochlorin-13¹-(2,3-dihydroxypropyl)amide-17³-(3-N-(2'-pyridyl)aminopropyl)amide, and
Palladium 3¹-oxo-15-methoxycarbonylmethyl-Rhodobacteriochlorin-13¹-(2,3-dihydroxypropyl)amide-17³-(4-N-(2'-pyridyl)aminobutyl)amide.

25. The bacteriochlorophyll compound according to claim 1, wherein:
M is 2H or Pd;
$R'_2$ is —$OR_8$ wherein $R_8$ is $C_1$-$C_6$ alkyl;
$R_4$ is —$COCH_3$;
$R_6$ is —NH—$CH_2$—$CH_2$—NRR'; and
$R_2$ is selected from the group consisting of
—NH—$(CH_2)_n$—OH;
—NH—CH(OH)—$CH_3$;
—NH—$(CH_2)_n$—NR—$(CH_2)_n$—OH; and
glycosylamino;
wherein R and R' each independently is H, methyl or ethyl; and n is 2 or 3.

26. The bacteriochlorophyll compound according to claim 25, selected from the group consisting of the compounds:
Palladium 3¹-oxo-15-methoxycarbonylmethyl-Rhodobacteriochlorin-13¹-(2-N²-dimethylaminoethyl)amide-17³-(2-hydroxy ethyl)amide,
Palladium 3¹-oxo-15-methoxycarbonylmethyl-Rhodobacteriochlorin-13¹-(2-N²-dimethylaminoethyl)amide-17³-(3-hydroxy propyl)amide,
Palladium 3¹-oxo-15-methoxycarbonylmethyl-Rhodobacteriochlorin-13¹-(2-N²-dimethylaminoethyl)amide-17³-(2-hydroxy propyl)amide,
Palladium 3¹-oxo-15-methoxycarbonylmethyl-Rhodobacteriochlorin-13¹-(2-N²-dimethylaminoethyl)amide-17³-((R)-2-hydroxypropyl)amide,
Palladium 3¹-oxo-15-methoxycarbonylmethyl-Rhodobacteriochlorin-13¹-(2-N²-dimethylaminoethyl)amide-17³—((S)-2-hydroxypropyl)amide,
Palladium 3¹-oxo-15-methoxycarbonylmethyl-Rhodobacteriochlorin-13¹-(2-N²-dimethylaminoethyl)amide-17³-(2-(2-hydroxyethylamino)ethyl)amide, and
Palladium 3¹-oxo-15-methoxycarbonylmethyl-Rhodobacteriochlorin-13¹-(2-N²-dimethylaminoethyl)amide-17³-(glycosyl)amide.

27. The bacteriochlorophyll compound of formula II according to claim 1, wherein M is Pd, $R'_2$ is —$OR_8$ wherein $R_8$ is $C_1$-$C_6$ alkyl, $R_4$ is —$COCH_2$, and $R_1$ and/or $R_6$ are —$NR_9R'_9$, wherein $R_9$ is H and $R'_9$ is $C_1$-$C_{25}$ hydrocarbyl substituted by a guanidino or guanidinium group.

28. The bacteriochlorophyll compound according to claim 27, wherein $R_1$ and $R_6$ are a group of the formula —NH—$(CH_2)_n$—C(=NH)—$NH_2$ or —NH—$(CH_2)$, —C(=NH)—$N^+(R)_3A^-$, wherein R is $C_2$-$C_6$ alkyl, n is an integer from 1 to 10, and $A^-$ is a physiologically acceptable anion.

29. The bacteriochlorophyll compound according to claim 28, selected from the group consisting of the compounds:
Palladium 3¹-oxo-15-methoxycarbonylmethyl-Rhodobacteriochlorin 13¹,17³-di(2-guanidinoethyl)amide and Palladium 3¹-oxo-15-methoxycarbonylmethyl-Rhodobacteriochlorin 13¹,17³-di(2-trimethylguanidiniumethyl) amide.

30. The bacteriochlorophyll compound of formula II according to claim 1, wherein M is H or Pd, $R'_2$ is $-OR_8$ wherein $R_8$ is $C_1$-$C_6$ alkyl, $R_4$ is $-COCH_3$, and $R_1$ and/or $R_6$ are $-NR_9R'_9$, wherein $R_9$ is H and $R'_8$ is $C_1$-$C_{25}$ hydrocarbyl substituted by a sulfonium group.

31. The bacteriochlorophyll compound according to claim 30, wherein $R_1$ and $R_6$ are a group of the formula $-NH-(CH_2)_n-S^+(R)_2$ $A^-$, wherein R is $C_1$-$C_6$ alkyl, n is an integer from 1 to 10, and $A^-$ is a physiologically acceptable anion.

32. The bacteriochlorophyll compound according to claim 31, which is the compound:
Palladium 3¹-oxo-15-methoxycarbonylmethyl-Rhodobacteriochlorin-13¹-(2-S²-dimethylsulfoniumethyl) amide citrate salt.

33. The bacteriochlorophyll compound of formula II according to claim 1, wherein M is H or Pd, $R'_2$ is $-OR_8$ wherein $R_8$ is $C_1$-$C_6$ alkyl, $R_4$ is $-COCH_3$, and $R_1$ and/or $R_6$ are $-NR_9R'_9$, wherein $R_9$ is H and $R'_9$ is $C_1$-$C_{25}$ hydrocarbyl substituted by a phosphino or phosphonium group.

34. The bacteriochlorophyll compound according to claim 33, wherein $R_1$ and $R_6$ are a group of the formula $-NH-(CH_2)_n-P(R)_2$ or $NH-(CH_2)_n-P^+(R)_3$ $A^-$, wherein R is $C_1$-$C_6$ alkyl, n is an integer from 1 to 10, and $A^-$ is a physiologically acceptable anion.

35. The bacteriochlorophyll compound according to claim 34, selected from the group consisting of the compounds:
3¹-oxo-15-methoxycarbonylmethyl-Rhodobacteriochlorin-13¹,17³-di(2-P³-trimethylphosphoniumethyl)amide dicitrate salt and
3¹-oxo-15-methoxycarbonylmethyl-Rhodobacteriochlorin-13¹,17³-di(2-dimethylphosphinoethyl)amide.

36. The bacteriochlorophyll compound of formula II according to claim 1, wherein M is H or Pd, $R'_2$ is $-OR_8$ wherein $R_8$ is $C_1$-$C_6$ alkyl, $R_4$ is $-COCH_3$, and $R_1$ and/or $R_6$ are $-NR_9R'_9$, wherein $R_9$ is H and $R'_9$ is $C_1$-$C_{25}$ hydrocarbyl substituted by an arsino or arsonium group.

37. The bacteriochlorophyll compound according to claim 36, wherein $R_1$ and $R_6$ are a group of the formula $-NH-(CH_2)_n-As(R)_2$ or $NH-(CH_2)_n-As^+(R)_3$ $A^-$, wherein R is $C_1$-$C_6$ alkyl, n is an integer from 1 to 10, and $A^-$ is a physiologically acceptable anion.

38. The bacteriochlorophyll compound according to claim 37, which is the compound:
31-Oxo-15-methoxycarbonylmethyl-Rhodobacteriochlorin-131,173-di(2-As3-trimethylarsoniumethyl)amide dicitrate salt.

39. A bacteriochlorophyll compound of formula II according to claim 1, wherein M is 2H or Pd, R'2 is $-OR8$ wherein R8 is C1-C6 alkyl, R4 is $-C(CH3)=NR9$, and R1 and/or R6 are
$-NR'9R''9$, wherein R'9 is H and R9 and R''9 are C1-C25 hydrocarbyl substituted by at least one amino end group.

40. The bacteriochlorophyll compound according to claim 39, wherein R4 is $-C(CH3)=N-(CH2)n-NH2$, R1 and R6 are both $-NH-(CH2)n-NH2$, and n is an integer from 1 to 10.

41. The bacteriochlorophyll compound according to claim 40, selected from the group consisting of the compounds:
3¹-(aminoethylimino)-15-methoxycarbonylmethyl-Rhodobacteriochlorin-13¹,17³-di(2-aminoethyl)amide and
Palladium 3¹-(aminoethylimino)-15-methoxycarbonylmethyl-Rhodobacterio-chlorin 13¹,17³-di(2-aminoethyl)amide.

42. The bacteriochlorophyll compound of formula II according to claim 1, wherein M is 2H or Pd, R'2 is $-OR8$ wherein R8 is C1-C6 alkyl, R4 is $-C(CH3)=NR9$, R1 and/or R6 are
$-NR'9R''_9$, wherein $R'_9$ is H and $R_9$ and $R''_9$ are $C_1$-$C_{25}$ hydrocarbyl substituted by at least one positively charged group.

43. The bacteriochlorophyll compound according to claim 42, wherein said positively charged group is an ammonium end group of the formula $-N^+(RR'R'')A^-$, wherein R, R' and R'' are the same or different $C_1$-$C_6$ alkyl, and $A^-$ is a physiologically acceptable anion.

44. The bacteriochlorophyll compound according to claim 43, wherein R4 is $-C(CH_3)=N-(CH_2)_n-N(R)_3^+A^-$, $R_1$ and $R_6$ are $-NH-(CH_2)_n-N(R)_3^+A^-$, wherein R is $C_1$-$C_6$ alkyl, n is an integer from 1 to 10, and $A^-$ is a physiologically acceptable anion.

45. The bacteriochlorophyll compound according to claim 44, selected from the group consisting of the compounds:
3¹-(trimethylammoniumethylimino)-15-methoxycarbonylmethyl-Rhodo-bacteriochlorin 13¹,17³-di(2-trimethylammoniumethyl)amide and
Palladium 3¹-(trimethylammoniumethylimino)-15-methoxycarbonylmethyl-Rhodobacteriochlorin 13¹,17³-di (2-trimethylammoniumethyl)amide.

46. A pharmaceutical composition comprising a bacteriochlorophyll compound of the formula II according to claim 1, and a pharmaceutically acceptable carrier.

47. A method for photodynamic therapy for treating tumors, said method comprising:
(a) administering to an individual in need a bacteriochlorophyll compound of the formula II according to claim 1; and
(b) irradiating the locale of the tumor.

48. The method according to claim 47, wherein said tumor is selected from the group consisting of melanoma, prostate, brain, head, neck, colon, ovarian, breast, a chest wall tumors arising from breast cancer, skin, lung, esophagus, bladder tumor and an hormone-sensitive tumor.

49. A method for photodynamic therapy of age-related macular degeneration which comprises:
(a) administering to an individual in need a bacteriochlorophyll compound of the formula II according to claim 1; and
(b) irradiating the locale of the macular degeneration.

50. A method for preventing or reducing in-stent restenosis comprising administering to an individual suffering from a cardiovascular disease that underwent coronary angiography an effective amount of a bacteriochlorophyll compound of the formula II according to claim 1, followed by local irradiation.

51. A method for treatment of atherosclerosis comprising administering to an individual in need an effective amount of a bacteriochlorophyll compound of the formula II according to claim 1, followed by local irradiation.

52. A method for diagnosing a tumor, comprising:
(a) administering to a subject suspected of having a tumor, a compound of the formula II according to claim 1;
(b) irradiating the subject by standard procedures; and
(c) measuring the fluorescence of the suspected area, wherein a higher fluorescence indicates tumor sites.

53. The bacteriochlorophyll compound according to claim 1, wherein said $C_1$-$C_{25}$ hydrocarbyl is $C_1$-$C_6$ alkyl.

54. The bacteriochlorophyll compound according to claim 6, wherein said R, R' and R'' is each independently a $C_1$-$C_6$ alkyl.

* * * * *